US011026596B1

(12) United States Patent
Lynn et al.

(10) Patent No.: US 11,026,596 B1
(45) Date of Patent: Jun. 8, 2021

(54) DETECTION AND MEASUREMENT OF TARGET SUBSTANCE IN EXHALED BREATH

(71) Applicant: Hound Labs, Inc., Oakland, CA (US)

(72) Inventors: Michael Scott Lynn, Piedmont, CA (US); Hamilton Roger Tang, Los Altos, CA (US); Kevin Bradford Dunk, Castro Valley, CA (US); Kevin M. Limtao, Milpitas, CA (US); Hayuta Jain, Alamo, CA (US)

(73) Assignee: HOUND LABS, INC., Oakland, CA (US)

( * ) Notice: Subject to any disclaimer, the term of this patent is extended or adjusted under 35 U.S.C. 154(b) by 375 days.

(21) Appl. No.: 15/981,797

(22) Filed: May 16, 2018

Related U.S. Application Data

(60) Provisional application No. 62/508,864, filed on May 19, 2017, provisional application No. 62/514,618, filed on Jun. 2, 2017.

(51) Int. Cl.
*A61B 5/08* (2006.01)
*G01N 33/58* (2006.01)
*A61B 5/097* (2006.01)
*A61B 5/087* (2006.01)
*G01N 33/94* (2006.01)

(52) U.S. Cl.
CPC .............. *A61B 5/082* (2013.01); *A61B 5/087* (2013.01); *A61B 5/097* (2013.01); *G01N 33/582* (2013.01); *G01N 33/948* (2013.01)

(58) Field of Classification Search
CPC ......... A61B 5/082; A61B 5/097; A61B 5/087; G01N 33/948; G01N 33/582
See application file for complete search history.

(56) References Cited

U.S. PATENT DOCUMENTS

| 3,086,833 | A  | 4/1963  | Streck |
| 3,676,072 | A  | 7/1972  | Krivis |
| 4,133,202 | A  | 1/1979  | Marple |
| 4,232,667 | A  | 11/1980 | Chalon et al. |
| 4,288,344 | A  | 9/1981  | Reiss |
| 4,771,005 | A  | 9/1988  | Spiro |
| 5,361,771 | A  | 11/1994 | Craine et al. |
| 5,922,610 | A  | 7/1999  | Alving et al. |
| 6,326,159 | B1 | 12/2001 | Ullman et al. |
| 6,537,823 | B1 | 3/2003  | Smith |
| 6,605,444 | B1 | 8/2003  | Klein et al. |
| 8,237,118 | B2 | 8/2012  | Prox et al. |

(Continued)

FOREIGN PATENT DOCUMENTS

| EP | 132313  | 9/1991 |
| EP | 2781917 | 9/2014 |

(Continued)

OTHER PUBLICATIONS

U.S. Appl. No. 15/650,537, Office Action dated Mar. 29, 2019.

(Continued)

*Primary Examiner* — Herbert K Roberts
*Assistant Examiner* — John M Royston
(74) *Attorney, Agent, or Firm* — Weaver Austin Villeneuve & Sampson LLP

(57) ABSTRACT

Systems, techniques and compositions can detect and measure a target substance, such as THC, in a constituent sample from exhaled human breath.

3 Claims, 45 Drawing Sheets

(56) References Cited

U.S. PATENT DOCUMENTS

| | | |
|---|---|---|
| 8,586,932 B2 | 11/2013 | Rousso et al. |
| 8,705,029 B2 | 4/2014 | Palmskog et al. |
| 8,707,758 B2 | 4/2014 | Keays |
| 9,429,564 B2 | 8/2016 | Beck |
| 9,709,581 B1 | 7/2017 | Gordon et al. |
| 9,709,582 B1 | 7/2017 | Gordon et al. |
| 9,726,684 B1 | 8/2017 | Gordon et al. |
| 9,921,234 B1 | 3/2018 | Lynn et al. |
| 9,933,445 B1 | 4/2018 | Lynn et al. |
| 9,945,878 B1 | 4/2018 | Gordon et al. |
| 9,970,950 B1 | 5/2018 | Lynn et al. |
| 9,976,944 B2 | 5/2018 | Olin et al. |
| 10,247,742 B1 | 4/2019 | Lynn et al. |
| 10,408,850 B1 | 9/2019 | Gordon et al. |
| 10,641,783 B2 | 5/2020 | Lynn et al. |
| 2002/0177232 A1 | 11/2002 | Melker et al. |
| 2003/0153844 A1 | 8/2003 | Smith |
| 2004/0043479 A1 | 3/2004 | Briscoe et al. |
| 2005/0105077 A1 | 5/2005 | Padmanabhan et al. |
| 2005/0137491 A1 | 6/2005 | Paz et al. |
| 2006/0094123 A1 | 5/2006 | Day et al. |
| 2006/0257941 A1 | 11/2006 | McDevitt et al. |
| 2007/0031283 A1 | 2/2007 | Davis et al. |
| 2007/0077660 A1 | 4/2007 | Glas |
| 2008/0004542 A1 | 1/2008 | Allen et al. |
| 2009/0017555 A1 | 1/2009 | Jehanli et al. |
| 2010/0297635 A1 | 11/2010 | Olin et al. |
| 2011/0086364 A1 | 4/2011 | Takkinen et al. |
| 2012/0302907 A1 | 11/2012 | Palmskog et al. |
| 2013/0006068 A1 | 1/2013 | Gemer et al. |
| 2013/0021153 A1 | 1/2013 | Keays |
| 2013/0102018 A1 | 4/2013 | Schentag et al. |
| 2013/0165806 A1 | 6/2013 | Wondka et al. |
| 2014/0094391 A1 | 4/2014 | McDevitt et al. |
| 2014/0288454 A1 | 9/2014 | Paz et al. |
| 2014/0366609 A1 | 12/2014 | Beck et al. |
| 2015/0033824 A1 | 2/2015 | Hammarlund et al. |
| 2015/0305651 A1 | 10/2015 | Attariwala et al. |
| 2015/0369830 A1* | 12/2015 | Crichlow ......... G01N 33/54386 436/501 |
| 2016/0000358 A1 | 1/2016 | Lundin et al. |
| 2017/0128692 A1 | 5/2017 | Christopher et al. |
| 2017/0184609 A1 | 6/2017 | Milton et al. |
| 2017/0303822 A1 | 10/2017 | Allsworth et al. |
| 2017/0303823 A1 | 10/2017 | Allsworth et al. |
| 2018/0120278 A1 | 5/2018 | Hoorfar et al. |
| 2018/0224471 A1 | 8/2018 | Lynn et al. |
| 2018/0238916 A1 | 8/2018 | Lynn et al. |
| 2018/0306775 A1 | 10/2018 | Beck et al. |
| 2020/0147333 A1 | 5/2020 | Stoll et al. |
| 2020/0182892 A1 | 6/2020 | Lynn et al. |
| 2020/0245898 A1 | 8/2020 | Heanue et al. |
| 2020/0245899 A1 | 8/2020 | Heanue et al. |
| 2020/0300876 A1 | 9/2020 | Lynn et al. |

FOREIGN PATENT DOCUMENTS

| | | |
|---|---|---|
| WO | 90/14043 | 11/1990 |
| WO | 2006/083269 | 8/2006 |
| WO | 2011/029889 | 3/2011 |
| WO | 2018/185164 | 10/2018 |
| WO | 2018/211280 | 11/2018 |
| WO | 2019/011750 | 1/2019 |
| WO | 2020/097382 | 5/2020 |
| WO | 2020/159698 | 8/2020 |

OTHER PUBLICATIONS

U.S. Appl. No. 15/650,537, Notice of Allowance dated Apr. 24, 2019.

U.S. Appl. No. 15/650,537, Notice of Allowance dated Jun. 14, 2019.

U.S. Appl. No. 15/875,195, Notice of Allowance dated Jan. 11, 2019.

U.S. Appl. No. 15/943,123, Office Action dated Mar. 6, 2020.

U.S. Appl. No. 15/943,123, Office Action dated Jun. 29, 2020.

International Search Report, dated Jan. 23, 2020, for Intnernational Patent Application No. PCT/US2019/060342, 2 pages.

Written Opinion of the Searching Authority, dated Jan. 23, 2020, for International Patent Application No. PCT/US2019/060342, 9 pages.

International Search Report, dated Apr. 6, 2020, for Intnernational Patent Application No. PCT/US2020/13553, 2 pages.

Written Opinion of the Searching Authority, dated Apr. 6, 2020, for International Patent Application No. PCT/US2020/13553, 7 pages.

Andrews, Travis M., "Breathalyzers of the Future Today," The Atlantic, Jun. 27, 2013. Downloaded from the Internet on Feb. 4, 2019, http://www.theatlantic.com/health/archive/2013/06/breathalyzers-of-the-future-today/277249/.

Dunk, et al., "Development of a Portable Marijuana Breathalyzer", (Mar. 2018), URL=http://https://houndlabs.com/wp-content/uploads/2018/03/Hound-TRT-Pittcon-Poster.pdf.

"N.S. woman who tested positive for pot when she wasn't high to challenge roadside testing laws," CBC Radio, posted Apr. 3, 2019. 6 pages.

Sarafian, Theodor et al., "Inhaled marijuana smoke disrupts mitochondrial energetics in pulmonary epithelial cells in vivo," Am J Physiol Lung Cell Mol Physiol, 2006, 290. L1202-L1209. (Year:2006).

Aliberti, S, et al., "Serum and exhaled breath condensate inflammatory cytokines in community-acquired pneumonia: a prospective cohort study", Pneumonia (Nathan), (Jun. 23, 2016), 8:8. doi: 10.1186/s41479-016-0009-7. eCollection 2016.

Bajaj, P., and F.T. Ishmael, "Exhaled breath condensates as a source for biomarkers for characterization of inflammatory lung diseases", Journal of Analytical Sciences, Methods and Instrumentation, (Mar. 20, 2013), 3(01):17.

Beck, O., et al., "Detection of drugs of abuse in exhaled breath using a device for rapid collection: comparison with plasma, urine and self-reporting in 47 drug users" Journal of breath research, (Apr. 25, 2013), 7(2):026006.

Carpenter, C.T., Price PV, Christman BW. Exhaled breath condensate isoprostanes are elevated in patients with acute lung injury or ARDS. Chest. Dec. 1, 1998;114(6):1653-9.

Emelyanov, A., et al., "Elevated concentrations of exhaled hydrogen peroxide in asthmatic patients", Chest, (Oct. 1, 2001), 120(4):1136-9.

Grob, N.M., et al., "Biomarkers in exhaled breath condensate: a review of collection, processing and analysis", Journal of breath research, (Sep. 8, 2008), 2(3):037004.

Hasan, R.A., et al., "$A_4$ and 8-isoprostane in the exhaled breath condensate of children hospitalized for status asthmaticus", Pediatric critical care medicine: a journal of the Society of Critical Care Medicine and the World Federation of Pediatric Intensive and Critical Care Societies, (Mar. 2012), 13(2):141.

Kodavanti, U.P. "Respiratory toxicity biomarkers", In *Biomarkers in Toxicology*, (Jan. 1, 2014) (pp. 217-239). Academic Press.

Krenke, K. et al., "Inflammatory cytokines in exhaled breath condensate in children with inflammatory bowel diseases", Pediatric pulmonology, (Dec. 2014), 49(12):1190-5.

Oguma, T., et al., "Clinical contributions of exhaled volatile organic compounds in the diagnosis of lung cancer", PloS one, (Apr. 6, 2017), 12(4):e0174802.

Saalberg, Yannick and Marcus Wolff, "VOC breath biomarkers in lung cancer", Clinica Chimica Acta, (Aug. 1, 2016), 459:5-9.

Samitas, K., et al., "Exhaled cysteinyl-leukotrienes and 8-isoprostane in patients with asthma and their relation to clinical severity", Respiratory medicine, (May 1, 2009), 103(5):750-6.

Wan, G.H., et al., "Cysteinyl leukotriene levels correlate with 8-isoprostane levels in exhaled breath condensates of atopic and healthy children", Pediatric research (Nov. 2013), 74(5):584.

Zanconato, S., et al., "Leukotrienes and 8-isoprostane in exhaled breath condensate of children with stable and unstable asthma", Journal of Allergy and Clinical Immunology, (Feb. 1, 2004), 113(2):257-63.

Zhou, J., "Review of recent developments in determining volatile organic compounds in exhaled breath as biomarkers for lung cancer diagnosis", Analytica chimica acta, (Dec. 15, 2017), 996:1-9.

(56) References Cited

OTHER PUBLICATIONS

"Drug detection, health monitoring etc.", SensAbues AB—Innovation, downloaded on Mar. 25, 2019 from http://sensabues.com/innovation.
"Exhaled breath biological sample matrix. EB", SensAbues AB—Product, downloaded on Mar. 25, 2019 from http://sensabues.com/product.
"Exhaled breath sampling company", SensAbues AB—About, downloaded on Mar. 25, 2019 from http://sensabues.com/about.
"FAIMS Breathalyzer Device", downloaded on Mar. 25, 2019 from https://algernonpharmaceuticals.com/faims-breathalyzer-device/.
"Low cost, non-invasive and non-intrusi", SensAbues AB—Benefits, downloaded on Mar. 25, 2019 from http://sensabues.com/benefits.
"Owlstone—About", downloaded on Mar. 25, 2019 from https://www.owlstonemedical.com/about/.
"Owlstone—EVOC Probes", downloaded on Mar. 25, 2019 from https://www.owlstonemedical.com/science-technology/evoc-probes/.
"Owlstone—FAIMS technology", downloaded on Mar. 25, 2019 from https://www.owlstonemedical.com/science-technology/faims-technology/.
"Owlstone—Research case studies", downloaded on Mar. 25, 2019 from https://www.owlstonemedical.com/science-technology/research-case-studies/.
"Owlstone Medical—Active Clinical Pipeline", downloaded on Mar. 25, 2019 from https://www.owlstonemedical.com/clinical-pipeline/.
"Owlstone Medical—The Home of Breath Biopsy: A Breathalyzer for Disease", downloaded on Mar. 25, 2019 from https://www.owlstonemedical.com/#.
"Owlstone Medical—The Home of Breath Biopsy: Breath Biopsy—VOC Biomarkers", downloaded on Mar. 25, 2019 from https://www.owlstonemedical.com/#.
"Owlstone Medical—Products", downloaded on Mar. 25, 2019 from https://www.owlstonemedical.com/products/.
"Pexa—About PExA", downloaded on Mar. 25, 2019 from http://pexa.se/en/about-pexa/.
"Pexa—Analysis", downloaded on Mar. 25, 2019 from http://pexa.se/en/product-services/analysis/.
"Pexa—Business Concept & Vision", downloaded on Mar. 25, 2019 from http://pexa.se/en/about-pexa/business-concept-vision/.
"Pexa—History", downloaded on Mar. 25, 2019 from http://pexa.se/en/about-pexa/history/.
"Pexa—How PExA works", downloaded on Mar. 25, 2019 from http://pexa.se/en/product-services/how-pexa-works/.
"Pexa—The importance of early diagnosis", downloaded on Mar. 25, 2019 from http://pexa.se/en/respiratory-research/the-importance-of-early-diagnosis/.
"Pexa—Particles in Exhaled Air", downloaded on Mar. 25, 2019 from http://pexa.se/en/.
"Pexa—PExA 2.0", downloaded on Mar. 25, 2019 from http://pexa.se/en/product-services/pexa-2-0/.
"Pexa—Product & Services", downloaded on Mar. 25, 2019 from http://pexa.se/en/product-services/.
"Pexa—Product-Sheet", Sep. 2016.
"Pexa—R&D and publications", downloaded on Mar. 25, 2019 from http://pexa.se/en/product-services/research-development/.
"Pexa—Research areas", downloaded on Mar. 25, 2019 from http://pexa.se/en/respiratory-research/research-areas/.
"Pexa—Respiratory Research Needs", downloaded on Mar. 25, 2019 from http://pexa.se/en/respiratory-research/.
"Pexa—The search for new biomarkers", downloaded on Mar. 25, 2019 from http://pexa.se/en/respiratory-research/the-search-for-new-biomarkers/.
"SensAbues AB—Next generation drug detection and health monitoring", SensAbues AB—Home, downloaded on Mar. 25, 2019 from http://sensabues.com/home.
"Volatile Organic Compounds (VOC) as non-invasive biomarkers for a range of diseases", downloaded on Mar. 25, 2019 from https://www.owlstonemedical.com/science-technology/voc-biomarkers/.
U.S. Appl. No. 16/248,656, filed Sep. 7, 2019, Michael Scott Lynn et al.
U.S. Appl. No. 16/790,457, filed Feb. 13, 2020, Michael Scott Lynn et al.
U.S. Appl. No. 15/943,123, filed Apr. 2, 2018, Michael Scott Lynn et al.
U.S. Appl. No. 16/823,113, filed Mar. 18, 2020, Michael Scott Lynn et al.
U.S. Appl. No. 14/997,405, Notice of Allowance dated May 10, 2017.
U.S. Appl. No. 14/997,405, Office Action dated Jan. 9, 2017.
U.S. Appl. No. 14/997,405, Corrected Notice of Allowability dated Jun. 15, 2017.
U.S. Appl. No. 15/143,379, Office Action dated Oct. 25, 2016.
U.S. Appl. No. 15/143,379, Notice of Allowance dated Mar. 21, 2017.
U.S. Appl. No. 15/143,379, Notice of Allowability dated Jun. 13, 2017.
U.S. Appl. No. 15/143,328, Office Action daed Sep. 1, 2016.
U.S. Appl. No. 15/143,328, Notice of Allowance dated Feb. 10, 2017.
U.S. Appl. No. 15/143,328, Notice of Allowability dated May 18, 2017.
U.S. Appl. No. 15/143,328, Notice of Allowance dated Jun. 14, 2017.
U.S. Appl. No. 15/650,518, Office Action dated Oct. 4, 2017.
U.S. Appl. No. 15/650,518, Notice of Allowance dated Feb. 1, 2018.
U.S. Appl. No. 14/641,412, Office Action dated May 19, 2016.
U.S. Appl. No. 14/641,412, Final Office Action dated Dec. 5, 2016.
U.S. Appl. No. 14/641,412, Office Action dated Jun. 26, 2017.
U.S. Appl. No. 14/641,412, Notice of Allowance dated Jan. 9, 2018.
U.S. Appl. No. 14/641,412, Corrected Notice of Allowability dated Apr. 18, 2018.
U.S. Appl. No. 15/217,151, Office Action dated Jan. 9, 2017.
U.S. Appl. No. 15/217,151, Office Action dated May 16, 2017.
U.S. Appl. No. 15/217,151, Final Office Action dated Oct. 30, 2017.
U.S. Appl. No. 15/217,151, Notice of Allowance dated Dec. 22, 2017.
U.S. Appl. No. 15/217,264, Office Action dated Oct. 24, 2016.
U.S. Appl. No. 15/217,264, Office Action dated Mar. 20, 2017.
U.S. Appl. No. 15/217,264, Final Office Action dated Aug. 16, 2017.
U.S. Appl. No. 15/217,264, Notice of Allowance dated Nov. 16, 2017.
Adams, I.B. et al., "Cannabis: pharmacology and toxicology in animals and humans," Addiction, Nov. 1996;91 (11):1585-614, PubMed abstract 8972919.
Al-Asmari, Ahmed et al., "Method for the quantification of diamorphine and its metabolites in pediatric plasma samples by liquid chromatography-tandem mass spectrometry," Journal of Analytical Toxicology, vol. 34, May 2010.
Atkinson, H.C. et al., "Drugs in human milk. Clinical pharmacokinetic considerations." Clin Pharmacokinet. Apr. 1988;14(4):217-40, PubMed abstract 3292101.
Azorlosa, J.L. et al., "Marijuana smoking: effect of varying delta 9-tetrahydrocannabinol content and number of puffs," J. Pharmacol. Exper. Ther 1992;261:114, abstract.
Bailey, J.R. et al., "Fetal disposition of delta 9-tetrahydrocannabinol (THC) during late pegnancy in the rhesus monkey," Toxicol Appl Pharmacol. Sep. 15, 1987;90(2):315-21, abstract.
Baker, D. et al., "Cannabinoids control spasticity and tremor in a multiple sclerosis model," Nature, Mar. 2, 2000;404(6773):84-7, abstract.
Balabanova, S. et al., "Detection of drugs in sweat," Belt Gerichtl Med. 1990;48:45-9, abstract.
Bashir, W. et al., "Spectrophotometric Determination of Acetone in Acetic Acid", Microchemical Journal, 1983, 28, pp. 77-81.
Beck, Olof et al., "Detection of Delta9-tetrahydrocannabinol in exhaled breath collected from cannabis users," Journal of Analytical Toxicology, vol. 35, Oct. 2011.

(56) References Cited

OTHER PUBLICATIONS

Benowitz, Neal L. et al., "Metabolic and psychophysiologic studies of cannabidiol-hexobarbital interaction," Clinical Pharmacology and Therapeutics (1980) 28, 115-120, abstract.

Blanc, Jennifer A. et al., "Adsorption losses from urine-based cannabinoid calibrators during routine use," Clin. Chem. 39/8, 1705-1712 (1993).

Bloom, A.S., Effect of delta9-tetrahydrocannabinol on the synthesis of dopamine and norepinephrine in mouse brain synaptosomes, J Pharmocol Exp Ther. Apr. 1982;221(1):97-103.

Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.

Bornheim, L.M. et al., "Human hepatic microsomal metabolism of delta 1-tetrahydrocannabinol," Drug Metab Dispos. Mar.-Apr. 1992;20(2):241-6, PubMed abstract 1352216.

Brenneisen, R. et al., "The effect of orally and rectally administered delta 9-tetrahydrocannabinol on spaticity: a pilot study with 2 patients," Int J Clin Pharmocol Ther. Oct. 1996;34(10):446-52.

Brunet, B. et al., "Validation of large white pig as an animal model for the study of cannabinoids metabolism: application to the study of THC distribution in issues," Forensic Sci Int. Sep. 12, 2006;161(2-3):169-74, PubMed abstract 16859848.

Burstein, S. et al., "Isolation and characterization of two major urinary metabolites of 1-tetrahydrocannabinol," Science, Apr. 28, 1972;176(4033):422-3, PubMed abstract 5026162.

Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.

Challapalli, P.V. et al., "In vitro experiment optimization for measuring tetrahydrocannabinol skin permeation," Int J Pharm. Jul. 25, 2002;241(2):329-39, PubMed abstract 12100860.

Chaturvedi, Arvind K., "Postmortem aviation forensic toxicology: an overview," Journal of Analytical Toxicology, vol. 34, May 2010.

"The Chemistry of Phenols," Zvi Rappoport, editor, © 2003 John Wiley & Sons, Ltd. ISBN: 0-471-49737-1.

Chiang, C. Nora et al., "Prenatal drug exposure: kinetics and dynamics," NIDA Research Monograph 60, 1985.

Christophersen, Asbjorg Solberg et al., "Tetrahydrocannabinol stability in whole blood: plastic versus glass containers," Journal of Analytical Toxicology, vol. 10, Jul./Aug. 1986.

Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.

Cone, Edward J. et al., "In vivo adulteration: excess fluid ingestion causes false-negative marijuana and cocaine urine test results," Journal of Analytical Toxicology, vol. 22, Oct. 1998.

Cone, Edward J. et al., "Marijuana-laced brownies: behavioral effects, physiologic effects, and urinalysis in humans following ingestion," Journal of Analytical Toxicology, vol. 12, Jul./Aug. 1988.

Cone, Edward J. et al., "Passive inhalation of marijuana smoke: urinalysis and room air levels of delta-9-tetrahydrocannabinol," Juornal of Analytical Toxicology, vol. 11, May/Jun. 1987.

Crouch, Dennis J. et al., "An evaluation of selected oral fluid point-of-collection drug-testing devices," Journal of Analytical Toxicology, vol. 29, May/Jun. 2005.

Crouch, D.J., "Oral fluid collection: the neglected variable in oral fluid testing," Forensic Sci Int. Jun. 10, 2005;150(2-3):165-73, PubMed abstract 15899565.

Day, David et al., "Detection of THCA in oral fluid by GC-MS-MS," Journal of Analytical Toxicology, vol. 30, Nov./Dec. 2006.

D'Sourza, Deepak Cyril et al., "The psychotomimetic effects of intravenous delta-9-tetrahydrocannabinol in healthy individuals: implications for psychosis," Neuropsychopharmacology (2004) 29, 1558-1572.

Ellis, G.M. Jr. et al., "Excretion patterns of cannabiniod metabolites after last use in a group of chronic users," Clin Pharmacol Ther. Nov. 1985;38(5):572-8, PubMed abstract 3902318.

Ellis, George M. Jr. et al. "Excretion patterns of cannabinoid metabilites after last use," 420 Magazine, Oct. 4, 2011, downloaded from https://www.420magazine.com/forums/drug-testing-urine/153724.

ElSohly, M. et al., "Potency trends of Delta9-THC and other cannabinoids in confiscated marijuana from 1980-1997," Journal of Forensic Sciences, vol. 45, No. 1, 2000, pp. 24-30.

Feng, Shixia et al., "Simultaneous analysis of Delta9-THC and its major metabolites in urine, plasma, and meconium by GC-MS using an immunoaffinity extraction procedure," Journal of Analytical Toxicology, vol. 24, Sep. 2000.

Fraser, A.D. et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.

Fraser, A.D. et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004;143(2-3):147-52, PubMed abstract 15240035.

Fraser, A.D. et al., "Urinary excretion profiles of 11-nor-9-carboxy-Delta9-tetrahydrocannabinol. Study III. A Delta9-THC-COOH to creatinine ratio study," Forensic Sci Int. Nov. 26, 2003;137(2-3):196-202, PubMed abstract 14609657.

Garrett, E.R. et al., "Pharmacokinetics of delta9-tetrahydrocannabinol in dogs," J Pharm Sci. Mar. 1977;66(3):395-407, PubMed abstract 845807.

Garrett, Edward R. et al., "Physicochemical properties, solubility, and protein binding of Delta9-tetrahydrocannabinol," J Pharm Sci. Jul. 1974;63(7):1056-64, abstract.

Gjerde, Hallvard et al., "Comparison of drug concentrations in blood and oral fluid collected with the Intercept® sampling device," Journal of Analytical Toxicology, vol. 34, May 2010.

Gjerde, H. et al., "Incidence of alcohol and drugs in fatally injured car drivers in Norway," Accid Anal Prev. Aug. 1993;25(4):479-83, PubMed abstract 8357462.

Goodwin, R.S. et al., "Delta(9)-tetrahydrocannabinol, 11-hydroxy-delta(9)-tetrahydrocannabinol and 11-nor-9-carboxy-delta(9)-tetrahydrocannabinol in human plasma after controlled oral administration of cannabinoids," Ther Drug Monit. Aug. 2006;28(4):545-51, PubMed abstract 16885723.

Green, Mitchell D. et al., "Glucuronidation of opioids, carboxylic acid-containing drugs, and hydroxylated xenobiotics catalyzed by expressed monkey UDP-glucuronosyltransferase 2B9 protein," Drug Metabolism and Disposition, vol. 25, No. 12, (1997).

Gross, Stanley J. et al., "Detection of recent cannabis use by saliva Delta9-THC radioimmunoassay," Journal of Analytical Toxicology, vol. 9, Jan./Feb. 1985.

Grotenhermen, F., "Pharmacokinetics and pharmacodynamics of cannabinids," Clin Pharmacokinet. 2003;42(4):327-60, PubMed abstract 12648025.

Gustafson, Richard A. et al., "Urinary cannabinoid detection times after controlled oral administration of Delta9-tetrahydrocannabinol to humans," Clinical Chemistry 49:7, 1114-1124 (2003).

Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.

Gustafson, R.A. et al., "Validated method for the simultaneous determination of Delta 9-tetrahydrocannabinol (THC), 11-hydroxy-THC and 11-nor-9-carboxy-THC in human plasma using solid phase extraction and gas chromatography-mass spectrometry with positive chemical ionization," J. Chromatogr B Analyt Technol Biomed Life Sci, Dec. 5, 2003;798(1):145-54, PubMed abstract 14630369.

Guy, G.W. et al., "A phase I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.

(56) References Cited

OTHER PUBLICATIONS

Hall, B.J. et al., "Determination of cannabinoids in water and human saliva by solid-phase microextraction and quadrupole ion trap gas chromatography/mass spectrometry," Anal chem. May 1, 1998;70(9):1788-96, PubMed abstract 9599579.

Halldin, M.M. et al., "Identification of in vitro metabolites of delta 1-tetrahydrocannabinol formed by human livers," Drug Metab Dispos. Jul.-Aug. 1982;10(4):297-301, PubMed abstract 6126323.

Hampson, A.J. et al., "Cannabidiol and (-)delta9-tetrahydrocannabinol are neuroprotective antioxidants," Proc Natl Acad Sci U.S.A. Jul. 7, 1998; 95(14): 8268-8273.

Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.

Harder, S. et al., "Concentration-effect relationship of delta-9-tetrahydrocannabiol and prediction of psychotropic effects after smoking marijuana," Int J Clin Pharmacol Ther. Apr. 1997;35(4):155-9, PubMed abstract 9112136.

Harvey, D.J. et al., "Metabolites of cannabidiol identified in human urine," Xenobiotic, Mar. 1990;20(3):303-20, PubMed abstract 2336840.

Hawks, Richard L., "The Analysis of Cannabinoids in Biological Fluids," NIDA Research Monograph 42, 1982.

Hazekamp, Arno et al., "Cannabis; extracting the medicine," thesis/dissertation 2007.

"Information for health care professionals: cannabis (marihuana, marijuana) and the cannabinoids," Health Canada, Feb. 2013.

Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.

Himes, Sarah K. et al., "Cannabinoids in exhaled breath following controlled administration of smoked cannabis," Clinical chemistry 59:12 1780-1789 (2013).

Huang, Wei et al., "Simultaneous determination of delta9-tetrahydrocannabinol and 11-nor-9-carboxy-delta9-tetrahydrocannabinol in human plasma by solid-phase extraction and gas chromatography-negative ion chemical ionization-mass spectrometry," Journal of Analytical Toxicology, vol. 25, Oct. 2001.

Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.

Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.

Huestis, Marilyn A. et al., "Cannabinoid concentrations in hair from documented cannabis users," Forensic Sci Int. Jul. 4, 2007; 169(2-3): 129-136.

Huestis, Marilyn A. et al., "Alternative testing matrices," chapter 11 of the Drug Abuse Handbook, 1998 CRC Press LLC, ISBN 0/8493-2637-0.

Huestis, M.A. et al., "Characterization of the absorption phase of marijuana smoking," Clin Pharmacol Ther. Jul. 1992;52(1):31-41, PubMed abstract 1320536.

Huestis, Marilyn A. et al., "Detection times of marijuana metabolites in urine by immunoassay and GC-MS," Journal of Analytical Toxicology, vol. 19, Oct. 1995.

Huestis, Marilyn A. et al., "Differentiating new marijuana use from residual drug excretion in occasional marijuana users," Journal of Analytical Toxicology, vol. 22, Oct. 1998.

Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).

Huestis, Marilyn A., "Human cannabinoid pharmacokinetics," Chem Biodivers. Aug. 2007; 4(8): 1770-1804.

Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.

Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.

Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.

Hunt, C.A. et al., "Tolerance and disposition of tetrahydrocannabinol in man," J Pharmacol Exp Ther. Oct. 1980;215(1):35-44, PubMed abstract 6256518.

Iribarne, C. et al., "Involvement of cytochrome P450 3A4 enzyme in the N-demethylation of methadone in human liver microsomes," Chem Res Toxicol. Mar. 1996;9(2):365-73, PubMed abstract 8839037.

Jehanli, A. et al., "Blind trials of an onsite saliva drug test for marijuana and opiates," J Forensic Sci. Sep. 2001;46(5):1214-20, PubMed 11569567.

Joern, William A., "Surface adsorption of the urinary marijuana carboxy metabolite: the problem and a partial solution," Letter to the Editor, Journal of Analytical Toxicology, vol. 16, Nov./Dec. 1992.

Johansson, E. et al., "Determination of delta 1-tetrahydrocannabinol in human fat biopsies from marihuana users by gas chromatography-mass spectrometry," Biomed Chromatogr. Jan. 1989;3(1):35-8, PubMed abstract 2539872.

Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.

Johannson, E. et al., "Terminal elimination plasma half-life of delta 1-tetrahydrocannabinol (delta 1-THC) in heavy users of marijuana," Eur J Clin Pharmacol. 1989;37(3):273-7, PubMed abstract 2558889.

Johansson, Eva et al., "Urinary excretion half-life of delta1-tetrahydrocannabinol-7-oic acid in heavy marijuana users after smoking," Journal of Analytical Toxicology, vol. 13, Jul./Aug. 1989.

Kadehijian, Leo, "Syva has been a leading developer and manufacturer of drugs-of-abuse tests for more than 30 years," Cannabinoid Issues: Passive inhalation, excretion patterns, and retention times, test result interpretation, Siemens Healthcare Diagnostics Inc., 2009.

Karst, Matthias et al., "Analgesic effect of the synthetic cannabinoid CT-3 on chronic neuropathic pain," JAMA. 2003;290(13):1757-1762.

Kelly, Peggy et al., "Metabolism of tetrahydrocannabinol in frequent and infrequent marijuana users," Journal of Analytical Toxicology, vol. 16, Jul./Aug. 1992.

Kemp, Philip M. et al., "Cannabinoids in Humans. II. The influence of three methods of hydrolysis on the concentration of THC and two metabolites in urine," Journal of Analytical Toxicology, vol. 19, Sep. 1995.

Kemp, Philip M. et al., "Cannabinoids in Humans. I. Analysis of delta9-tetrahydrocannabinol and six metabolites in plasma and urine using GC-MS," Journal of Analytical Toxicology, vol. 19, Sep. 1995.

Kidwell, David A. et al., "Testing for drugs of abuse in saliva and sweat," Journal of Chromatography B: Biomedical Sciences and Applications, vol. 713, Issue 1, Aug. 21, 1998, pp. 111-135, abstract.

Kintz, Pascal et al., "Detection of cannabis in oral fluid (saliva) and forehead wipes (sweat) from impaired drivers," Journal of Analytical Toxicology, vol. 24, Oct. 2000.

Kintz, Pascal et al., "Sweat testing for heroin and metabolites in a heroin maintenance program," Clinical Chemistry 43:5, 736-739 (1997).

Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.

Kovatsi, Leda et al., "Development and validation of a high-performance liquid chromatography method for the evaluation of

(56) References Cited

OTHER PUBLICATIONS niflumic acid cross-reactivity of two commercial immunoassays for cannabinoids in urine," Journal of Analytical Toxicology, vol. 34, May 2010.
Kreuz, D.S. et al., "Delta-9-tetrahydrocannabinol: localization in body fat," Science, Jan. 26, 1973;179(4071):391-3, PubMed abstract 4682965.
Krishna, D.R. et al., "Extrahepatic metabolism of drugs in humans," Clin Pharmacokinet. Feb. 1994;26(2):144-60, PubMed abstract 8162658.
Lafolie, P. et al., "Importance of creatinine analyses of urine when screening for abused drugs," Clin. Chem. 37/11, 1927-1931 (1991).
Laloup, M. et al., "Correlation of delta9-tetrahydrocannabinol concentrations determined by LC-MS-MS in oral fluid and plasma from impaired drivers and evaluation of the on-site Drager Drug Test," Forensic Sci Int. Sep. 12, 2006;161(2-3): 175-9, PubMed abstract 16842950.
Law, B. et al., "Forensic aspects of the metabolism and excretion of cannabinoids following oral ingestion of cannabis resin," J Pharm Pharmacol. May 1984;36(5):289-94, PubMed abstract 6145762.
Lee, Sooyeun et al., "Estimation of the measurement uncertainty by the bottom-up approach for the determination of methamphetamine and amphetamine in urine," Journal of Analytical Toxicology, vol. 34, May 2010.
Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.
Lemberger, L. et al., "Delta-9-tetrahydrocannabinol: metabolism and disposition in long-term marihuana smokers," Science. Jul. 2, 1971;173(3991):72-4, PubMed abstract 5087483.
Lemberger, L. et al., "Marihuana: studies on the disposition and metabolism of delta-9-tetrahydrocannabinol in man," Science. Dec. 18, 1970;170(3964):1320-2, PubMed abstract 5479011.
Lindgren, J.E. et al., "Clinical effects and plasma levels of delta 9-tetrahydrocannabinol (delta 9-THC) in heavy and light users of cannabis," Psychopharmacology (Berl). 1981;74(3):208-12, PubMed 6267648.
Malfait, A.M. "The nonpsychoactive cannabis constituent cannabidiol is an oral anti-arthritic therapeutic in murine collagen-induced arthritis," Proc Natl Acad Sci USA Aug. 15, 2000;97(17):9561-9566.
Manno, Joseph E. et al., "Temporal indication of marijuana use can be estimated from plasma and urine concentrations of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.
Manolis, Antony et al., "The detection of delta9-tetrahydrocannabinol in the breath of human subjects," Clinical Biochem. 16,229 (1983).
"Marihuana '84," Proceedings of the Oxford Symposium on Cannabis, D.J. Harvy, editor, IRL Press, Oxford 1984.
Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.
Mason, A.P. et al., "Cannabis: pharmacology and interpretation of effects," J Forensic Sci. Jul. 1985;30(3):615-31, PubMed abstract 2993473.
Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.
Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.
Mattes, R.D. et al., "Bypassing the first-pass effect for the therapeutic use of cannabinoids," Pharmacol Biochem Behav. Mar. 1993;44(3):745-7, PubMed abstract 8383856.
Mattes, R.D. et al., "Cannabinoids and appetite stimulation," Pharmacol Biochem Behav. Sep. 1994;49(1):187-95, PubMed abstract 7816872.
McBurney, L.J. et al., "GC/MS and EMIT analyses for delta9-tetrahydrocannabinol metabolites in plasma and urine of human subjects," Journal of Analytical Toxicology, vol. 10, Mar./Apr. 1986.
Mechoulam, Raphael et al., "Cannabidiol: an overview of some chemical and pharmacological aspects. Part I: chemical aspects," Chemistry and Physics of Lipids 121 (2002) 35-43.
Mechoulam, Raphael, "Plant cannabinoids: a neglected pharmacological treasure trove," Br J Pharmacol. Dec. 2005; 146(7): 913-915.
Meier, H. et al., "Cannabis poisoning after eating salad," Schweiz Med Wochenschr. Feb. 8, 1997;127(6):214-8, PubMed abstract 9157527.
Menkes, D.B. et al., "Salivary THC following cannabis smoking correlates with subjective intoxication and heart rate," Psychopharmacology (Berl). 1991;103(2):277-9, PubMed abstract 1851311.
Mijuriya, Tod H., "Cannabis as a substitute for alcohol: a harm-reduction approach," Journal of Cannabis Therapeutics, vol. 4(1) 2004.
Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.
Moeller, M.R. et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.
Moldoveanu, Serban C. et al., "Differences in the chemical composition of the particulate phase of inhaled and exhaled cigarette mainstream smoke," Contributions to Tobacco Research 22(4), 290 (2007).
Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.
Moore, Christine et al., "Application of two-dimensional gas chromatography with electron capture chemical ionization mass spectrometry to the detection of 11-nor-delta9-tetrahydrocannabinol-9-carboxylic acid (THC-COOH) in hair," Journal of Analytical Toxicology, vol. 30, Apr. 2006.
Moore, Christine et al., "Detection of the marijuana metabolite 11-nor-delta9-tetrahydrocannabinol-9-carboxylic acid in oral fluid specimens and its contribution to positive results in screening assays," Journal of Analytical Toxicology, vol. 30, Sep. 2006.
Moore, Christine et al., "The determination of 11-nor-delta9-tetrahydrocannabinol-9-carboxylic acid (THC-COOH) in hair using negative ion gas chromatography—mass spectrometry and high-volume injection," Journal of Analytical Toxicology, vol. 25, Oct. 2001.
Morland, J. et al., "Cannabinoids in blood and urine after passive inhalation of cannabis smoke," J Forensic Sci. Oct. 1985;30(4):997-1002, PubMed abstract 2999292.
Mule, S.J. et al., "Active and realistic passive marijuana exposure tested by three immunoassays and GC/MS in urine," Journal of Analytical Toxicology, vol. 12, May/Jun. 1988.
Mura, P. et al., "Evaluation of six rapid tests for screening of cannabis in sweat, saliva and tears," Acta Clin Belg. 1999;53 Suppl 1:35-8, PubMed abstract 10216980.
Mura, P. et al., "THC can be detected in brain while absent in blood," Letter to the Editor, Journal of Analytical Toxicology, vol. 29, Nov./Dec. 2005.
Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.
Nadulski T. et al., "Simultaneous and sensitive analysis of THC, 11-OH-THC, THC-COOH, CBD, and CBN by GC-MS in plasma

(56) References Cited

OTHER PUBLICATIONS after oral application of small doses of THC and cannabis extract," Journal of Analytical Toxicology, vol. 29, Nov./Dec. 2005.
Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.
Niedbala, R. Sam et al., "Detection of marijuana use by oral fluid and urine analysis following single-dose administration of smoked and oral marijuana," Journal of Analytical Toxicology, vol. 25, Jul./Aug. 2001.
Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.
Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.
Ohlsson, Agneta et al., "Single dose kinetics of deuterium labelled delta1-tetrahydrocnnabinol in heavy and light cannabis users," Biological Mass Spectrometry, vol. 9, Issue 1, pp. 6-10, Jan. 1982, abstract.
Owens, S. Michael et al., I Radioimmunoassay of delta-9-tetrahydrocannabinol in blood and plasma with a solid-phase second-antibody separation method, Clin. Chem. 27/4, 619-624 (1981).
Peel, H.W. et al., "Detection of drugs in saliva of impaired drivers," J Forensic Sci. Jan. 1984;29(1):185-9, PubMed abstract 6366113.
Perez-Reyes, M. et al., "The clinical pharmacology and dynamics of marihuana cigarette smoking," J Clin Pharmacol. Aug.-Sep. 1981;21(8-9 Suppl):201S-207S, PubMed abstract 6271825.
Perez-Reyes, M. et al., "Comparison of effects of marihuana cigarettes to three different potencies," Clin Pharmacol Ther. May 1982;31(5):617-24, PubMed abstract 6280918.
Perez-Reyes, M. et al., "Intravenous injection in man of 9-tetrahydrocannabinol and 11-OH-9-tetrahydrocannabinol," Science. Aug. 18, 1972;177(4049):633-5, PubMed abstract 4558903.
Perez-Reyes, Mario, "Marijuana smoking: factors that influence the bioavailability of tetrahydrocannabinol," NIDA Monograph 1990;99:42.
Piao, Wen et al., "Development of azo-based fluorescent probes to detect different levels of hypoxia," Angew. Chem. Int. Ed. 2013, 52, 13028-13032.
Quintela, Oscar et al., "Recovery of drugs of abuse from the immunalysis quantisal™ oral fluid collection device," Journal of Analytical Toxicology, vol. 30, Oct. 2006.
Rahim S.A. et al., "Colorimetric determination of ethanol in the presence of methanol and other species in aqueous solution," Talanta. Nov. 1992;39(11):1489-91, PubMed abstract 18965558.
Rohrich, J. et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.
Russo, E. et al., "A tale of two cannabinoids: the therapeutic rational for combining tetrahydrocannabinol and cannabidiol," Med Hypotheses. 2006;66(2):234-46, PubMed abstract 16209908.
Samyn N. et al., "On-site testing of saliva and sweat with Drugwipe and determination of concentrations of drugs of abuse in saliva, plasma and urine of suspected users," Int J Legal Med. 2000;113(3):150-4, PubMed abstract 10876986.
Scheuplein, Robert J., "Mechanism of percutaneous absorption. II. Transient diffusion and the relative importance of various routes of skin penetration," J. Invest. Dermatol 1967;48:79.
Schwartz, Richard H. et al., "Laboratory detection of marijuana use, Experience with a photometric immunoassay to measure urinary cannabinoids," Aj J Dis Child. 1985;139(11):1093-1096, abstract.
Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).
Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).
Skopp, G. et al., "Partition coefficient, blood to plasma ratio, protein binding and short-term stability of 11-nor-Delta(9)-carboxy tetrahydrocannabinol glucuronide," Forensic Sci Int. Mar. 28, 2002;126(1):17-23, PubMed abstract 11955826.
Soares, J.R. et al., "Significant developments in radioimmune methods applied to delta9-THC and its 9-substituted metabolites," Analysis of Cannabinoids Research Monograph 42, NIDA 1982.
Stinchcomb, A.L. et al., "Human skin permeation of Delta8-tetrahydrocannabinol, cannabidiol and cannbinol," J Pharm Pharmacol. Mar. 2004;56(3):291-7, PubMed abstract 15025853.
Strano-Rossi, Sabina et al., "Analysis of stimulants in oral fluid and urine by gas chromatography-mass spectrometry II: Pseudophedrine," Journal of Analytical Toxicology, vol. 34, May 2010.
Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.
Teshima, N. et al, "Determination of acetone in breath", Analytica Chimica Acta, 2005, 535, pp. 189-199.
Toennes, Stefan W. et al., "Pharmacokinetic properties of delta9-tetrahydrocannabinol in oral fluid of occasional and chronic users," Journal of Analytical Toxicology, vol. 34, May 2010.
Turner, Carton E. et al., "Constituents of *Cannabis sativa* 1. XVII. A review of the natural constituents," J. Nat. Prod. 1980;43:169.
Valiveti, S. et al., "In vitro/in vivo correlation studies for transdermal delta 8-THC development," J Pharm Sci. May 2004;93(5):1154-64, PubMed abstract 15067692.
Van der Kooy, F. et al., "Cannabis smoke condensate I: The effect of different preparation methods on tetrahydrocannabinol levels," Inhalation Toxicology, 20:801-804, 2008.
Vinciguerra, V. et al., "Inhalation marijuana as an antiemetic for cancer chemotherapy," NY State J Med. Oct. 1988;88(10):525-7.
Wall, M.E. et al., "The metabolism of delta 9-tetrahydrocannabinol and related cannabinoids in man," J Clin Pharmacol. Aug.-Sep. 1981;21 (8-9 Suppl):178S-189S, PubMed abstract 6271823.
Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.
Walsh, J. Michael et al., "An evaluation of rapid point-of-collection oral fluid drug-testing devices," Journal of Analytical Toxicology, vol. 27, Oct. 2003.
Watanabe, K. et al., "Brain microsomal oxidation of delta 8- and delta 9-tetrahydrocannabinol," Biochem Biophys Res Commun. Nov. 30, 1988;157(1):75-80, PubMed abstract 2848522.
Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.
Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.
Wingert, William E., "Lowering cutoffs for initial and confirmation testing for cocaine and marijuana: large-scale study of effects on the rates of drug-positive results," Clinical Chemistry 43:1 100-103 (1997).
Zajicek, J. et al., "Cannabinoids for treatment of spasticity and other symptoms related to multiple sclerosis (CAMS study): multicentre randomised placebo-controlled trial," Lancet. Nov. 8, 2003;362(9395):1517-26, abstract.
Zias, Joe et al., "Early medical use of cannabis," Nature; May 20, 1993; 363,6426; Research Library Core p. 215.
Zuardi, A.W. et al., "Action of cannabidiol on the anxiety and other effects produced by delta 9-THC in normal subjects," Psychopharmacology (Berl). 1982;76(3):245-50, PubMed abstract 6285406.
U.S. Appl. No. 15/650,537, filed Jul. 14, 2017, Gordon et al.
U.S. Appl. No. 15/958,616, filed Apr. 20, 2018, Lynn et al.
U.S. Appl. No. 15/875,195, filed Jan. 19, 2018, Lynn et al.
U.S. Appl. No. 15/943,123, filed Apr. 2, 2018, Lynn et al.
U.S. Appl. No. 15/958,616, Notice of Allowance dated Jan. 2, 2020.

(56) References Cited

OTHER PUBLICATIONS

U.S. Appl. No. 15/875,195, Office Action dated Apr. 19, 2018.
U.S. Appl. No. 15/943,123, Notice of Allowance dated Nov. 12, 2020.
U.S. Appl. No. 15/943,123, Notice of Allowance dated Dec. 22, 2020.
Alexander, Brentan R., "Design of a microbreather for two-phase microchannel devices", Dissertation submitted to Massachusetts Institute of Technology. Dept. of Mechanical Engineering, (Jun. 2008), 59 pages.
U.S. Appl. No. 16/563,839, filed Sep. 7, 2019, Michael Scott Lynn et al.
U.S. Appl. No. 16/248,656, filed Jan. 15, 2019, Michael Scott Lynn et al.
U.S. Appl. No. 15/981,797, filed May 16, 2018, Michael Scott Lynn et al.
U.S. Appl. No. 16/124,181, filed Sep. 6, 2018, Michael Scott Lynn et al.
U.S. Appl. No. 16/729,116, filed Dec. 27, 2019, Michael Scott Lynn et al.
U.S. Appl. No. 16/776,501, filed Jan. 29, 2020, Michael Scott Lynn et al.
U.S. Appl. No. 16/655,182, filed Oct. 16, 2019, Michael Scott Lynn et al.
U.S. Appl. No. 17/247,926, filed Dec. 30, 2020, Michael Scott Lynn et al.
U.S. Appl. No. 16/949,065, filed Oct. 12, 2020, Gordon et al.
U.S. Appl. No. 16/949,066, filed Oct. 12, 2020, Michael Scott Lynn et al.
U.S. Appl. No. 16/563,839, Office Action dated Apr. 15, 2020.
U.S. Appl. No. 16/248,656, Office Action dated Mar. 5, 2020.
U.S. Appl. No. 16/248,656, Office Action dated Jul. 13, 2020.
U.S. Appl. No. 16/124,181, Office Action dated Jan. 1, 2021.

* cited by examiner

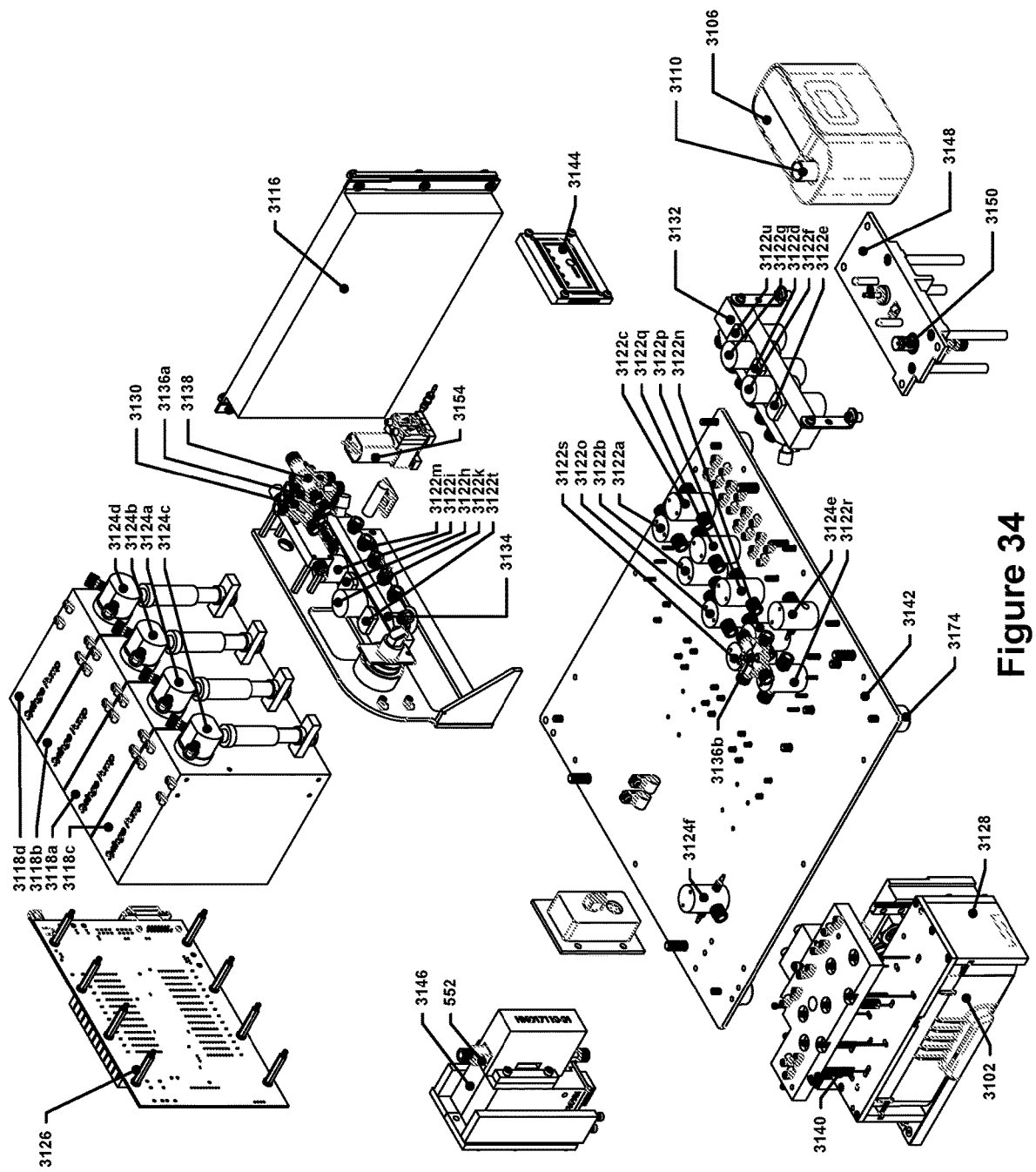

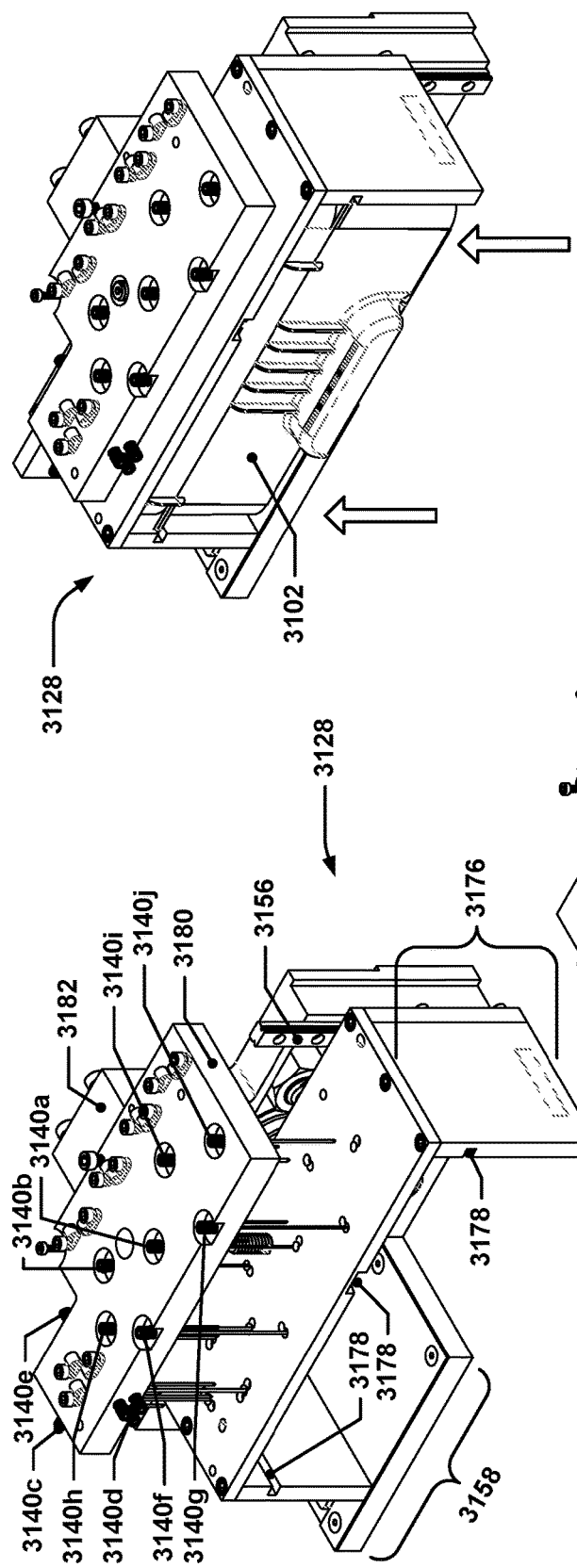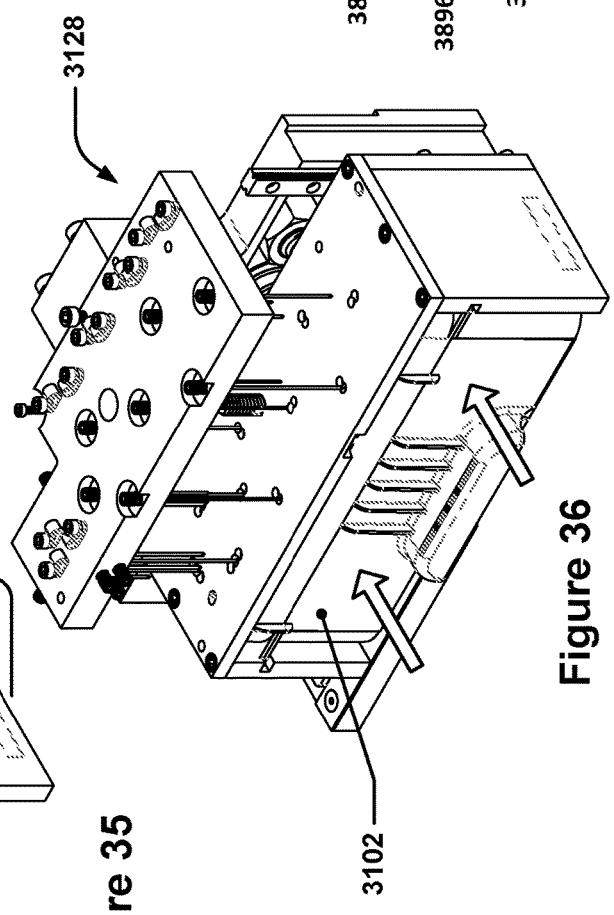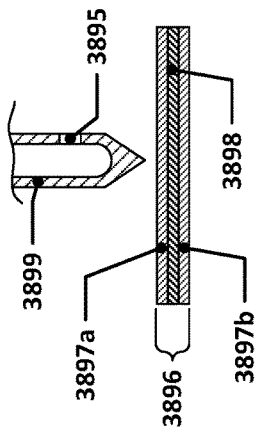

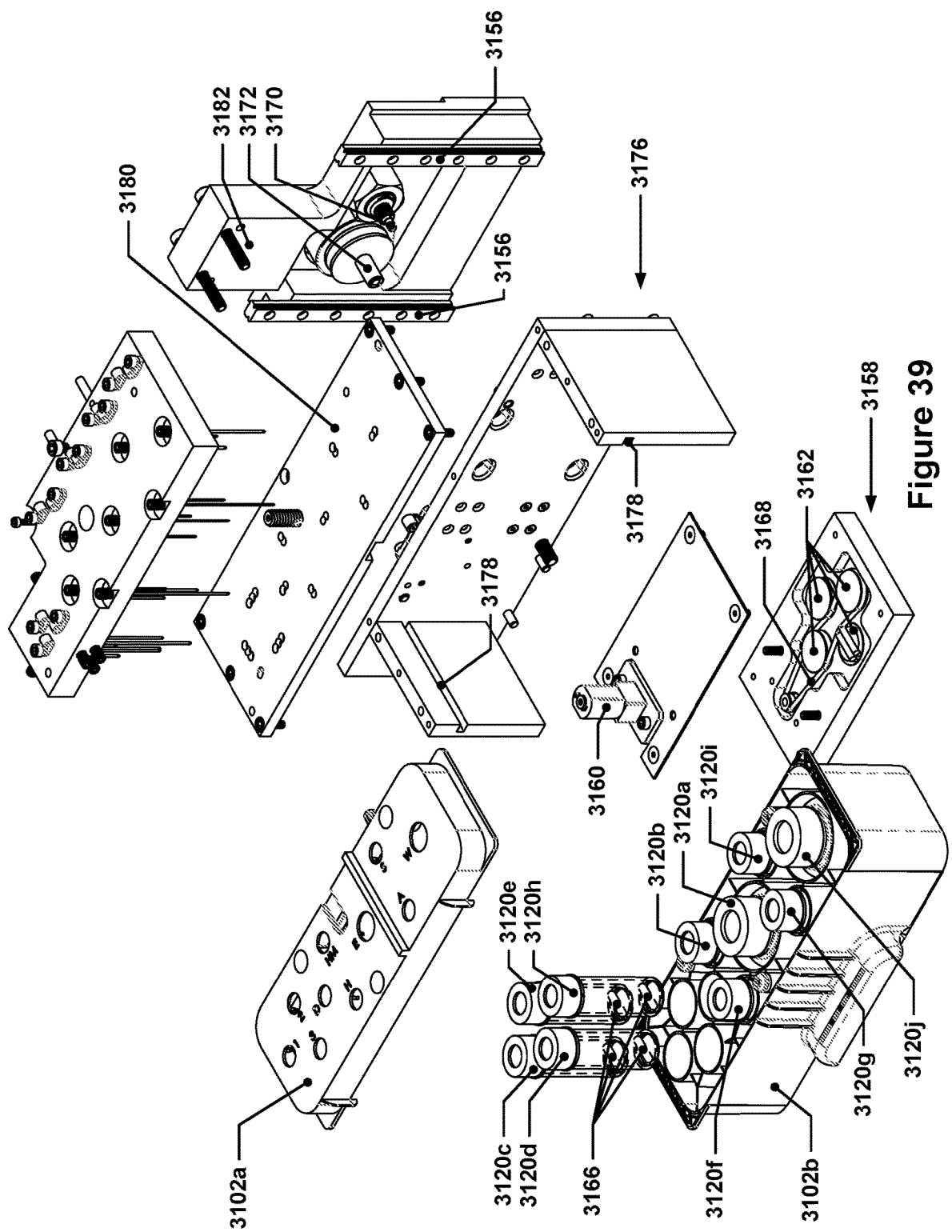

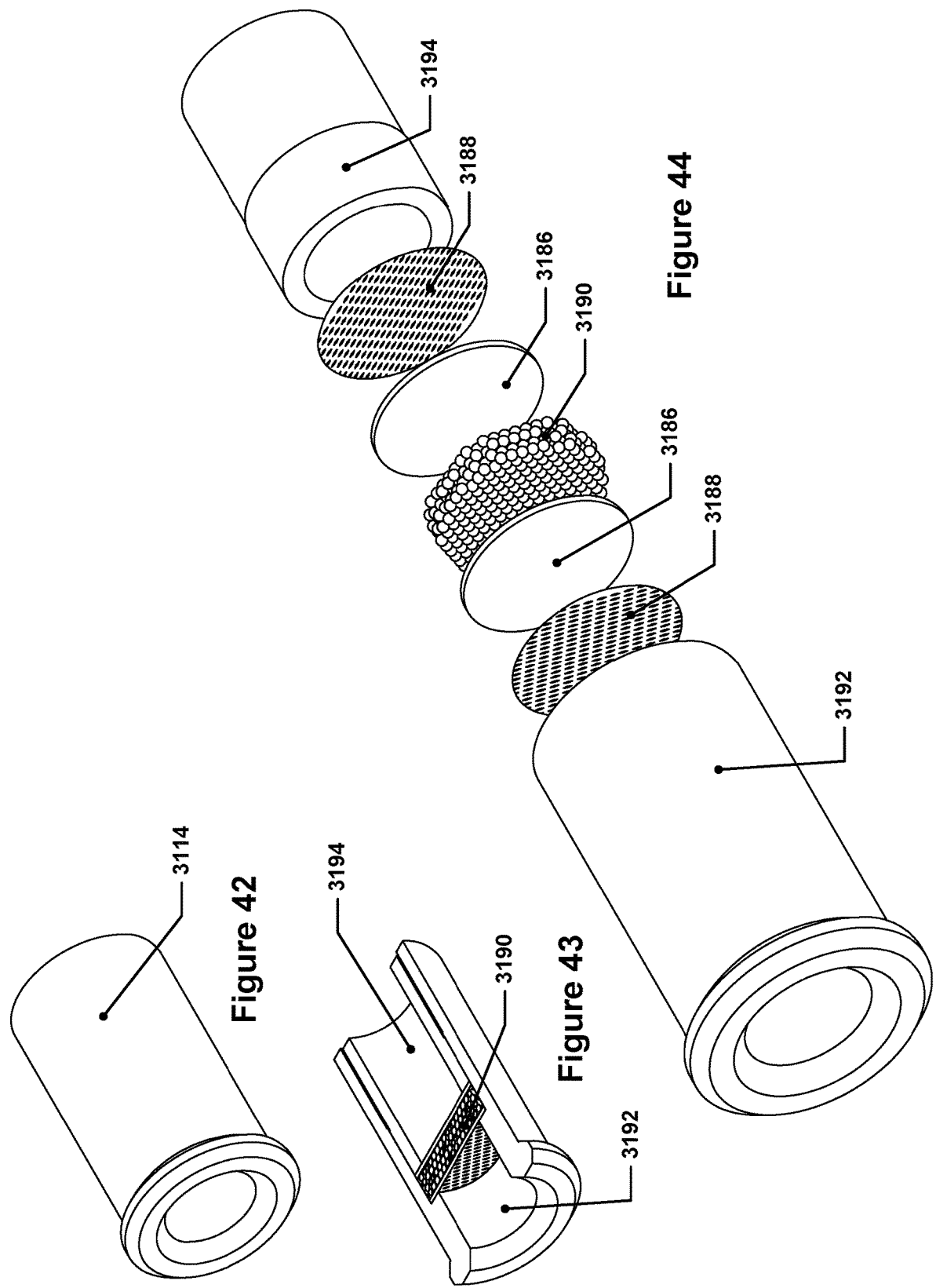

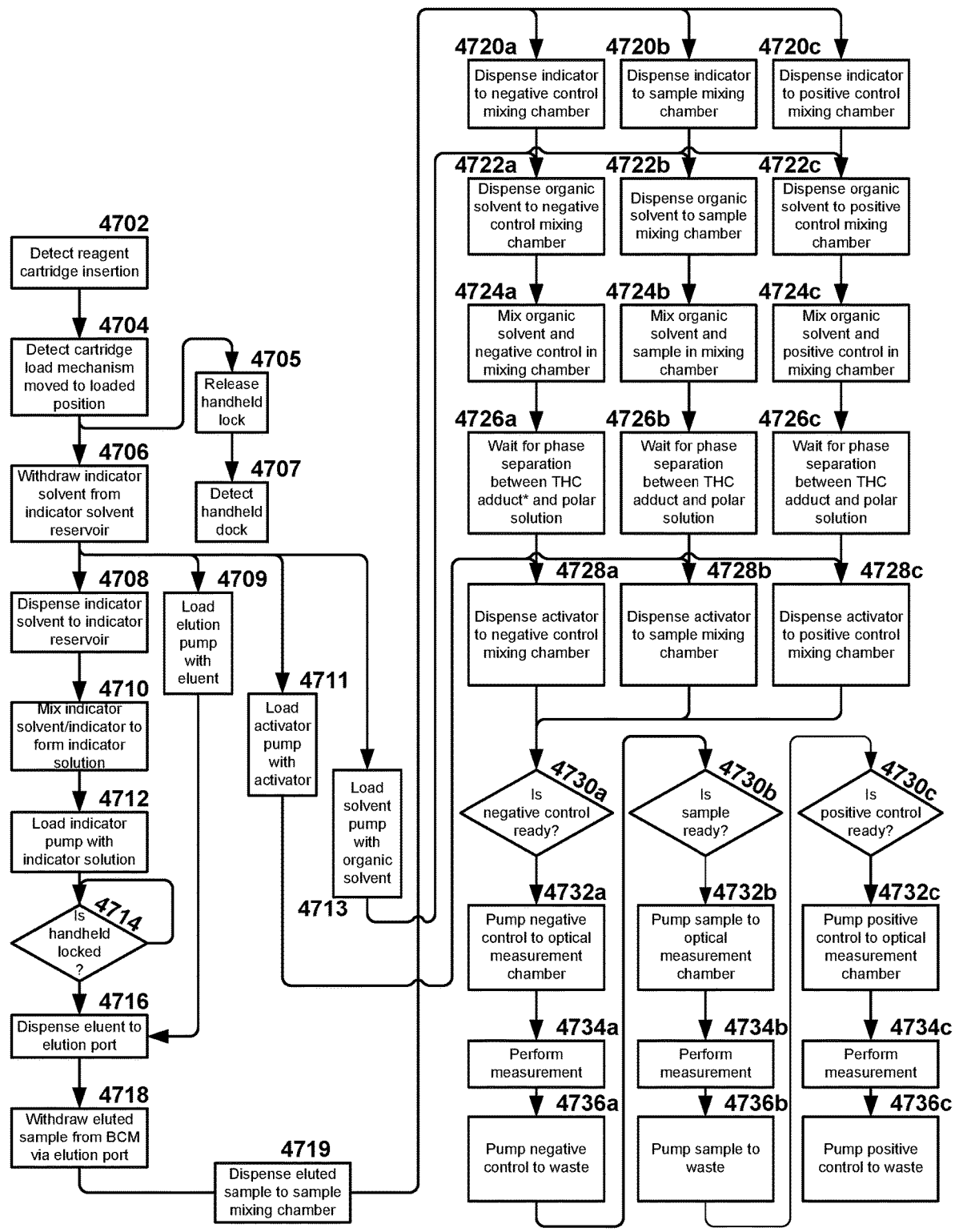
Figure 47                *If negative control has no THC, adduct may not be present.

DETECTION AND MEASUREMENT OF TARGET SUBSTANCE IN EXHALED BREATH

CROSS REFERENCE TO RELATED APPLICATIONS

This application claims benefit of priority under 35 U.S.C. § 119(e), and hereby incorporates by reference herein, to the following applications: U.S. Patent Application No. 62/514,618, filed Jun. 2, 2017, and titled "SYSTEM AND METHOD FOR TARGET SUBSTANCE IDENTIFICATION," U.S. Patent Application No. 62/508,864, filed May 19, 2017, and titled "SYSTEM AND METHOD FOR TARGET SUBSTANCE IDENTIFICATION." This application also incorporates herein by reference U.S. Provisional Patent Application No. 62/337,286, filed May 16, 2016, and titled "BREATH COLLECTOR MODULE," U.S. Provisional Patent Application No. 62/351,858, filed Jun. 17, 2016, and titled "COMPOSITIONS AND METHODS FOR DETECTION OF TARGET CONSTITUENT IN EXHALED BREATH," U.S. Provisional Patent Application No. 62/351,821, filed Jun. 17, 2016, and titled "SYSTEM AND METHOD FOR TARGET SUBSTANCE IDENTIFICATION," U.S. patent application Ser. No. 15/217,151, filed Jul. 22, 2016, and titled "COMPOSITIONS AND METHODS FOR DETECTION OF TARGET CONSTITUENT IN EXHALED BREATH," U.S. patent application Ser. No. 14/997,405, titled "METHOD, DEVICE AND SYSTEM FOR TARGET SUBSTANCE DETECTION" and filed Jan. 15, 2016, U.S. Provisional Application Nos. 62/104,813, filed Jan. 18, 2015, and 62/107,331, filed Jan. 23, 2015, both of which are titled "METHOD, DEVICE AND SYSTEM FOR TARGET SUBSTANCE DETECTION," and U.S. Provisional Application No. 62/277,854, filed Jan. 12, 2016, and titled "PORTABLE, HANDHELD INSTRUMENT FOR DETECTION AND QUANTIFICATION OF CANNABINOIDS AND ALCOHOL IN EXHALED HUMAN BREATH."

FIELD OF THE INVENTION

The present disclosure relates generally to analytical measurement, and more specifically to devices, systems, methods and compositions for detecting and measuring substances in exhaled human breath.

BACKGROUND

With legalization of marijuana expanding and the risk of marijuana-associated impaired driving increasing, it is anticipated by the present inventors that there will be an increased need for portable and accurate measurement devices for quantifying levels of cannabinoid compounds, such as tetrahydrocannabinol (THC), that are present in a person's breath, e.g., such as during a traffic stop for suspected driving-under-the-influence. THC detection poses significant challenges since the amounts of THC that may be present in an exhaled breath are quite minute—much more so than is the case with alcohol. Furthermore, THC detection in human breath is generally the only reliable way to determine if a suspected marijuana user is under the influence. Unlike with alcohol, which the body can purge in relatively short order, e.g., less than a day, THC compounds may be present in a person's body long after they are no longer under the influence of the THC. Thus, detection of THC via blood or urine sample may result in false positives in terms of being under the influence of marijuana. Testing for THC in breath at the roadside would be convenient, non-invasive, and leverages the wide acceptance of administering a breath test at the roadside, as is commonly employed for alcohol.

SUMMARY

Details of one or more implementations of the subject matter described in this specification are set forth in the accompanying drawings and the description below. Other features, aspects, and advantages will become apparent from the description, the drawings, and the claims.

In some implementations, a tetrahydrocannabinol (THC) detection system may be provided that includes an indicator reservoir containing a functionalized fluorophore that, when combined with a sample containing THC, produces an adduct with the THC that is present in the sample. The THC detection system may also include an activator reservoir containing an activator comprising poly(2-ethyl hexyl acrylate), a mechanism configured to cause the activator to be combined with the adduct, an optical measurement device configured to obtain measurements of light emitted from at least some of the combined adduct and activator and to produce one or more signals indicative of the measurement, and a controller configured to cause: the functionalized fluorophore to be combined with the sample, the activator to be introduced into the adduct to activate the adduct, and one or more measurements of light to be obtained from the activated adduct.

In some implementations, a tetrahydrocannabinol (THC) detection system may be provided that includes an analysis unit. The analysis unit may include one or more pumps (each pump of the one or more pumps configured to pump liquid), an elution port, an optical measurement chamber, an optical measurement device (the optical measurement device configured to obtain intensity measurements, during analysis of a sample, for light emitted from a fluid pumped into the optical measurement chamber), one or more reagent cartridge receptacles configured to receive a corresponding one or more reagent cartridges, and a plurality of fluidic interfaces (each fluidic interface configured to interface with a different internal volume of the one or more reagent cartridges when the one or more reagent cartridges are loaded into the corresponding one or more reagent cartridge receptacles, and each of the internal volumes being a reservoir or a mixing chamber). The plurality of fluidic interfaces may include an indicator fluidic interface configured to interface with an indicator reservoir of the one or more reagent cartridges, an indicator solvent fluidic interface configured to interface with an indicator mixing chamber of the one or more reagent cartridges, a sample fluidic interface configured to interface with a sample mixing chamber of the one or more reagent cartridges, a positive control fluidic interface configured to interface with a positive control mixing chamber of the one or more reagent cartridges, a negative control fluidic interface configured to interface with a negative control mixing chamber of the one or more reagent cartridges, and an eluent fluidic interface configured to interface with an eluent reservoir of the one or more reagent cartridges. The analysis unit may also include a plurality of valves that are configured to, in conjunction with the operation of the one or more pumps, control fluid flow from or to: the elution port, the indicator fluidic interface, the indicator solvent fluidic interface, the solvent fluidic interface, the eluent fluidic interface, the optical measurement chamber, and the one or more pumps. The plurality of valves may be arranged such that fluid flow between such components is controllable to permit, when the one or more reagent cartridges are installed in the analysis unit: an eluent to be conveyed to the elution port from the eluent reservoir of the one or more cartridges via the eluent fluidic interface, a mixture of an eluted breath constituent sample and the eluent to be conveyed from the elution port to the sample mixing chamber of the one or more cartridges via the sample fluidic interface, an indicator solvent to be conveyed to the indicator mixing chamber of the one or more cartridges from the indicator solvent reservoir of the one or more cartridges via the indicator solvent fluidic interface, a solution of indicator solvent and indicator to be conveyed to the sample mixing chamber, the negative control mixing chamber, and the positive control mixing chamber of the one or more cartridges from the indicator mixing chamber of the one or more cartridges via the indicator fluidic interface, a portion of a negative control mixture including the indicator and any adduct that is formed through mixing of the indicator with any THC in a negative control located in the negative control mixing chamber of the one or more cartridges to be conveyed from the negative control mixing chamber of the one or more cartridges to the optical measurement chamber via the sample fluidic interface, a portion of a sample mixture including the breath constituent sample, the indicator, and any adduct that is formed through mixing of the indicator with any THC that is present in the breath constituent sample to be conveyed from the sample mixing chamber of the one or more cartridges to the optical measurement chamber via the sample fluidic interface, and a portion of a positive control mixture including the indicator and any adduct that is formed through mixing of the indicator with THC in a positive control located in the positive control mixing chamber of the one or more cartridges to be conveyed from the positive control mixing chamber of the one or more cartridges to the optical measurement chamber via the sample fluidic interface.

In some implementations, a tetrahydrocannabinol (THC) detection system may be provided that includes an indicator reservoir containing a functionalized fluorophore that, when combined with a sample containing THC, produces an adduct with the THC that is present in the sample. The detection system may further include an activator reservoir containing an activator that includes poly(2-ethyl hexyl acrylate) as a constituent, a mechanism configured to cause the activator to be combined with the adduct, an optical measurement device configured to obtain measurements of light emitted from at least some of the combined adduct and activator and to produce one or more signals indicative of the measurement, and a controller configured to cause: the functionalized fluorophore to be combined with the sample, the activator to be introduced into the adduct to activate the adduct, and one or more measurements of light to be obtained from the activated adduct.

In some implementations, a THC detection system including an analysis unit that includes one or more pumps, each of which may be configured to pump liquid. The analysis unit may further include an elution port, an optical measurement chamber, an optical measurement device, one or more reagent cartridge receptacles configured to receive a corresponding one or more reagent cartridges, and a plurality of fluidic interfaces. Each fluidic interface may be configured to interface with a different internal volume of the one or more reagent cartridges when the one or more reagent cartridges are loaded into the corresponding one or more reagent cartridge receptacles, and the optical measurement device may be configured to obtain intensity measurements, during analysis of a sample, for light emitted from a fluid pumped into the optical measurement chamber. Each of the internal volumes may be a reservoir or a mixing chamber, and the plurality of fluidic interfaces may include: an indicator fluidic interface configured to interface with an indicator reservoir of the one or more reagent cartridges, an indicator solvent fluidic interface configured to interface with an indicator mixing chamber of the one or more reagent cartridges, a sample fluidic interface configured to interface with a sample mixing chamber of the one or more reagent cartridges, a positive control fluidic interface configured to interface with a positive control mixing chamber of the one or more reagent cartridges, a negative control fluidic interface configured to interface with a negative control mixing chamber of the one or more reagent cartridges, and an eluent fluidic interface configured to interface with an eluent reservoir of the one or more reagent cartridges. The analysis unit may additionally include a plurality of valves that are configured to, in conjunction with the operation of the one or more pumps, control fluid flow from or to: the elution port, the indicator fluidic interface, the indicator solvent fluidic interface, the solvent fluidic interface, the eluent fluidic interface, the optical measurement chamber, and the one or more pumps. The plurality of valves may be arranged such that fluid flow between such components is controllable to permit, when the one or more reagent cartridges are installed in the analysis unit: an eluent to be conveyed to the elution port from the eluent reservoir of the one or more cartridges via the eluent fluidic interface, a mixture of an eluted breath constituent sample and the eluent to be conveyed from the elution port to the sample mixing chamber of the one or more cartridges via the sample fluidic interface, an indicator solvent to be conveyed to the indicator mixing chamber of the one or more cartridges from the indicator solvent reservoir of the one or more cartridges via the indicator solvent fluidic interface, a solution of indicator solvent and indicator to be conveyed to the sample mixing chamber, the negative control mixing chamber, and the positive control mixing chamber of the one or more cartridges from the indicator mixing chamber of the one or more cartridges via the indicator fluidic interface, a portion of a negative control mixture including the indicator and any adduct that is formed through mixing of the indicator with any THC in a negative control located in the negative control mixing chamber of the one or more cartridges to be conveyed from the negative control mixing chamber of the one or more cartridges to the optical measurement chamber via the sample fluidic interface, a portion of a sample mixture including the breath constituent sample, the indicator, and any adduct that is formed through mixing of the indicator with any THC that is present in the breath constituent sample to be conveyed from the sample mixing chamber of the one or more cartridges to the optical measurement chamber via the sample fluidic interface, and a portion of a positive control mixture including the indicator and any adduct that is formed through mixing of the indicator with THC in a positive control located in the positive control mixing chamber of the one or more cartridges to be conveyed from the positive control mixing chamber of the one or more cartridges to the optical measurement chamber via the sample fluidic interface. In some further implementations, the system may include the one or more reagent cartridges.

In some implementations, at least the indicator reservoir, the indicator mixing chamber, the sample mixing chamber, the positive control mixing chamber, and the negative control mixing chamber may be internal volumes in the same reagent cartridge of the one or more reagent cartridges. In such implementations, the indicator mixing chamber may contain an indicator that forms an adduct when combined with tetrahydrocannabinol (THC), the indicator solvent reservoir may contain an indicator solvent in which the indicator is soluble, the sample mixing chamber may contain a buffer with no THC present, the positive control mixing chamber may contain a positive control solution of a basic buffer and a first predetermined amount of THC, and the negative control mixing chamber may contain a negative control solution such as a) the basic buffer without any THC or b) a solution of the basic buffer and a second predetermined amount of THC. In such implementations, the second predetermined amount of THC may be lower than the first predetermined amount of THC.

In some implementations of the system, the analysis unit may further include a handheld dock configured to receive a handheld sample collection unit such that a breath collector module of the handheld sample collection unit may be fluidically interfaced with the elution port. In some such implementations of the system, the system may include the handheld sample collection unit and the handheld sample collection unit may further include the breath collector module.

In some implementations of the system, the handheld sample collection unit may further include a blood alcohol concentration sensor that is fluidically connected with the breath collector module such that a portion of exhaled breath provided to the handheld sample collection unit passes into the blood alcohol concentration sensor.

In some implementations of the system the plurality of fluidic interfaces may further include an activator fluidic interface configured to interface with an activator reservoir of the one or more reagent cartridges, and the plurality of valves may be further configured to also control fluid flow from or to the activator fluidic interface and are further arranged such that fluid flow in the apparatus is controllable to permit, when the one or more reagent cartridges are installed in the analysis unit, an activator to be conveyed from the activator reservoir of the one or more cartridges to the sample mixing chamber, the negative control mixing chamber, and the positive control mixing chamber of the one or more cartridges via the activator fluidic interface.

In some implementations of the system, the one or more reagent cartridges may be a single cartridge and the one or more reagent cartridge receptacles may be a single reagent cartridge receptacle.

In some implementations of the system the reagent cartridge receptacle may include one or more rotatable sets of one or more magnets that are positioned such that each set of one or more magnets is located beneath a mixing chamber of the reagent cartridge when the reagent cartridge is fully installed in the analysis unit and each set of one or more magnets, when rotated, generates a rotating magnetic field that causes a magnetic stir bar located in the corresponding mixing chamber to rotate when the reagent cartridge is fully installed in the analysis unit, and the analysis unit may further include one or more drive motors configured to cause the one or more rotatable sets of one or more magnets to rotate in response to a signal.

In some implementations of the system, the reagent cartridge receptacle may include an elevator that includes a horizontally extending platform that supports the one or more rotatable sets of one or more magnets, and the elevator, and the horizontally extending platform, may be configured to be movable along a vertical axis relative to the plurality of fluidic interfaces such that the reagent cartridge, when loaded into the elevator, is movable between a loaded configuration in which the plurality of fluidic interfaces are each interfaced with the internal volumes of the reagent cartridge and an unloaded configuration in which the plurality of fluidic interfaces are not interfaced with the internal volumes of the reagent cartridge.

In some implementations, the plurality of fluidic interfaces may further include an organic solvent interface configured to interface with an organic solvent reservoir of the one or more reagent cartridges, and the plurality of valves may be further configured to also control fluid flow from or to the organic solvent fluidic interface and are further arranged such that fluid flow in the apparatus is controllable to permit, when the one or more reagent cartridges are installed in the analysis unit, an organic solvent to be conveyed from the organic solvent reservoir of the one or more cartridges to the sample mixing chamber, the negative control mixing chamber, and the positive control mixing chamber of the one or more cartridges via the organic solvent fluidic interface.

In some implementations of the system, the system may include a mixing mechanism operable to agitate fluids in the mixing chambers of the one or more reagent cartridges when the one or more reagent cartridges are installed in the analysis unit and the mixing mechanism is activated, and a controller that includes: one or more processors and a memory. The one or more processors, the memory, the valves, the one or more pumps, and the optical measurement device may be operatively connected, and the memory may store computer-executable instructions for controlling the one or more processors to determine that the one or more reagent cartridges are loaded into the corresponding one or more reagent cartridge receptacles, and then, after determining that the one or more reagent cartridges are loaded into the corresponding one or more reagent cartridge receptacles: a) cause the indicator solvent to be conveyed from the indicator solvent reservoir to the indicator mixing chamber to form the solution of indicator and indicator solvent, b) cause the eluent to be conveyed from the eluent reservoir to the elution port, c) cause, after (b), the eluent and eluted breath constituent sample to be conveyed to the sample mixing chamber, d) cause, after (a), the solution of indicator and indicator solvent to be conveyed to the sample mixing chamber, the negative control mixing chamber, and the positive control mixing chamber, e) cause, after (d), the mixing mechanism to agitate the contents of the sample mixing chamber, the negative control mixing chamber, and the positive control mixing chamber, f) cause, after the contents of the negative control mixing chamber are mixed in (e), the portion of the negative control mixture to be conveyed to the optical measurement chamber and then analyzed by the optical measurement device to obtain a negative control measurement, g) cause, after the contents of the sample mixing chamber are mixed in (e), the portion of the sample mixture to be conveyed to the optical measurement chamber and then analyzed by the optical measurement device to obtain a sample measurement, and h) cause, after the contents of the positive control mixing chamber are mixed in (e), the portion of the positive control mixture to be conveyed to the optical measurement chamber and then analyzed by the optical measurement device to obtain a positive control measurement.

In some implementations of the system, the plurality of fluidic interfaces may further include an organic solvent interface configured to interface with an organic solvent reservoir of the one or more reagent cartridges, the plurality of valves may be further configured to also control fluid flow from or to the organic solvent fluidic interface and are further arranged such that fluid flow in the apparatus is controllable to permit, when the one or more reagent cartridges are installed in the analysis unit, an organic solvent to be conveyed from the organic solvent reservoir of the one or more cartridges to the sample mixing chamber, the negative control mixing chamber, and the positive control mixing chamber of the one or more cartridges via the organic solvent fluidic interface, and the memory may further store computer-executable instructions for controlling the one or more processors to cause the organic solvent to be conveyed to the sample mixing chamber, the negative control mixing chamber, and the positive control mixing chamber before (e).

In some implementations of the system, the memory may further store computer-executable instructions for controlling the one or more processors to cause (a) to be performed before (b) and responsive to receipt of a first signal indicating that a handheld sample collection unit configured to be interfaced with the elution port is being prepared for sample collection.

In some implementations of the system, the memory may further store computer-executable instructions for controlling the one or more processors to cause, after (b) and before (d), the mixing mechanism to agitate the contents of the indicator mixing chamber.

In some implementations of the system, the analysis unit may further include a handheld dock sensor configured to detect when the handheld sample collection unit is removed from a handheld dock located on the analysis unit, wherein the first signal is a signal produced by the handheld dock sensor when the handheld sample collection unit is removed from the handheld dock.

In some implementations of the system, the analysis unit may further include a level sensor configured to provide information indicative of whether the analysis unit is within a predetermined range of angular orientations with respect to the earth's gravitational field, and the memory may further store computer-executable instructions for controlling the one or more processors to provide a notification when the level sensor indicates that the analysis unit is outside of the predetermined range of angular orientations.

In some implementations of the system, the memory may further store computer-executable instructions for controlling the one or more processors to cause (f), (g), and (h) to be performed after (e) and after the level sensor indicates that the analysis unit is within the predetermined range of angular orientations for at least a first predetermined time interval after (e).

In some implementations of the system, the analysis unit may further include a plurality of supports that are independently adjustable and that support the analysis unit with respect to a surface on which the analysis unit is placed, each support having a locking mechanism that is configured to be transitioned between an engaged state and an disengaged state. In such implementations, the locking mechanism for each support, in the engaged state, may prevent that support from moving, and the locking mechanism for each support, in the disengaged state, may allow that support to move.

In some implementations, the locking mechanisms may be configured to be transitioned from their engaged states to their disengaged states as a group and responsive to receipt of a first input, and transitioned from their disengaged states to their engaged states as a group and responsive to receipt of a second input.

In some implementations, a reagent cartridge may be provided that includes a housing, the housing including one or more features configured to cause the reagent cartridge to be oriented and positioned in a predetermined manner relative to an analysis unit when the reagent cartridge is inserted into a reagent cartridge receptacle of the analysis unit. The reagent cartridge may further include a plurality of internal volumes within the housing, each internal volume fluidically isolated from the other internal volumes within the housing. The plurality of internal volumes may include: an indicator mixing chamber containing an indicator that forms an adduct when combined with THC, an indicator solvent reservoir containing an indicator solvent in which the indicator is soluble, a sample mixing chamber containing a buffer with no THC present, a positive control mixing chamber containing a positive control solution of a basic buffer and a first predetermined amount of THC, a negative control mixing chamber containing a negative control solution selected from the group consisting of: a) the basic buffer without any THC and b) a solution of the basic buffer and a second predetermined amount of THC, in which the second predetermined amount of THC is lower than the first predetermined amount of THC, an eluent reservoir containing an eluent, an organic solvent reservoir containing an organic solvent, an activator reservoir containing an activator that, when mixed with the adduct, causes the adduct to emit light at a greater intensity when exposed to a stimulus than the adduct would emit in response to the same stimulus absent mixing of the activator with the adduct, a sample reservoir, and a waste reservoir.

In some such implementations of the reagent cartridge, the indicator may be a powderized diazo-functionalized reactant.

In some implementations of the reagent cartridge, the activator may be poly(2-ethyl hexyl acrylate).

In some implementations, a reagent cartridge kit may be provided that includes one or more removable cartridges, the one or more removable cartridges configured to be insertable into a THC analysis unit. A plurality of reservoirs and mixing chambers may be distributed within the one or more removable cartridges, and the plurality of reservoirs and mixing chambers may include: an indicator mixing chamber containing an indicator that forms an adduct when combined with THC, an indicator solvent reservoir containing an indicator solvent in which the indicator is soluble, a sample mixing chamber containing a buffer with no THC present, a positive control mixing chamber containing a positive control solution of a basic buffer and a first predetermined amount of THC, a negative control mixing chamber containing a negative control solution selected from the group consisting of: a) the basic buffer without any THC and b) a solution of the basic buffer and a second predetermined amount of THC, wherein the second predetermined amount of THC is lower than the first predetermined amount of THC, an eluent reservoir containing an eluent, an organic solvent reservoir containing an organic solvent, an activator reservoir containing an activator that, when mixed with the adduct, causes the adduct to emit light at a greater intensity when exposed to a stimulus than the adduct would emit in response to the same stimulus absent mixing of the activator with the adduct, a sample reservoir, and a waste reservoir.

In one aspect, a method of detecting THC in exhaled breath involves receiving or obtaining, such as from or with a breath capture device or system module, an exhaled breath sample, processing the breath sample such that any THC in the breath sample forms a fluorescent-labeled sample adduct dissolved in a nonpolar phase of an adduct solution, activating the fluorescent-labeled THC sample adduct's fluorophore with a liquid phase chemical activator, such as by adding an acryloyl species to the nonpolar phase, and detecting by determining an amount of THC in the breath sample based on the measured fluorescence of the activated fluorescent-labeled THC sample adduct in the nonpolar phase isolated from aqueous media.

A method of detecting THC in exhaled breath may be characterized as another embodiment. The method involves obtaining or receiving an exhaled breath sample, such as from or with a breath capture device or system module, capturing THC in the exhaled breath sample by adsorption on and then elution from a capture media, forming a fluorescent-labeled sample adduct with captured THC from the breath sample in a basic buffered sample adduct solution, adding to the sample adduct solution a second solvent and mixing to form a mixture, separating the mixture into polar and nonpolar phases, the nonpolar phase containing the fluorescent-labeled THC sample adduct, activating the fluorescent-labeled THC sample adduct's fluorophore by adding an acryloyl species to the nonpolar phase, isolating the fluorescent-labeled THC sample adduct from aqueous media, and detecting by exposing the sample adduct in the nonpolar phase to a light source to produce a fluorescence, measuring the fluorescence, and determining a quantity of THC captured and collected from the breath sample based on the measured fluorescence of the sample adduct in the nonpolar phase. The fluorescent-labeled THC sample adduct's fluorophore may be activated either before or after isolating the fluorescent-labeled THC sample adduct from aqueous media, and the detection by measured fluorescence can be conducted after the fluorescent-labeled THC sample adduct is isolated from aqueous media. In some embodiments, degradation in signal detected from the activated fluorophore is observed the longer the nonpolar phase contacts the polar (aqueous) phase if the activator is added after separation but before isolation. Therefore, in some embodiments, isolation of the fluorescent-labeled THC sample adduct in the nonpolar phase from aqueous media precedes activation.

In accordance with either of these embodiments, THC in a breath sample can be captured by adsorption on a catch medium or catch media. The breath sample may be obtained, for example, with a handheld device, sometimes referred to as a breath capture module, suitable for roadside use. THC in a breath sample obtained with the device can be captured by adsorption on a catch medium or catch media contained within the device. THC adsorbed on the catch medium may be eluted from the capture medium using a first solvent. A basic buffer and an aqueous diazotized fluorophore solution may then be added to the capture solution to form a fluorescent-labeled THC adduct in a sample adduct solution. Methods in accordance with described embodiments avoid the need for complex immunological-based detection techniques.

In various implementations, after formation of the adduct solution, the fluorescent-labeled THC adduct can be separated from the aqueous components of the sample adduct solution. Initially, a second solvent may be added to the sample adduct solution, the resulting mixture vigorously mixed, and the mixture then allowed to separate into polar and nonpolar phase layers. Any fluorescent-labeled THC-adduct will be contained in the nonpolar phase layer, and thereby separated by solvent extraction from molecular species that dissolve in polar, but not nonpolar solvents. The fluorescent-labeled THC adduct is thereby separated from non-target molecular species that dissolve in polar, but not nonpolar solvents.

In various implementations, the first and/or second solvents can be organic solvents, the diazotized fluorophore solution is aqueous, and at least one of the first and second solvents is a nonpolar solvent immiscible with water. For example, in some implementations the first solvent is a polar organic solvent miscible with water, such as an alcohol, e.g., ethanol, and the second solvent is a nonpolar organic solvent immiscible with water, such as an alkane, ether, or combinations thereof. For example, the nonpolar organic solvent may include heptane and methyl tertiary butyl ether (MTBE) in proportions from about 15-50% by volume MTBE with the balance heptane, such as 75 vol % heptane and 25 vol % MTBE. Also in various implementations, the diazotized fluorophore solution is acidic with an acid strength such that the pH of the adduct solution remains basic by the action of the basic buffer.

In various implementations, the fluorescence signal generated by the fluorescent-labeled THC adduct's fluorophore can be strengthened by activation, e.g., chemical activation, and/or by removing the nonpolar phase from contact with the polar phase following solvent extraction of the fluorescent-labeled THC adduct into the nonpolar phase. In various implementations, prior to the phase separation and exposing the sample adduct to the light source, the fluorescent-labeled THC adduct's fluorophore is activated. The fluorophore can be activated by adding a liquid phase chemical activator into the nonpolar phase of the sample adduct mixture, for example following solvent extraction to isolate the sample adduct in the nonpolar phase, or after isolating the solvent-extracted fluorescent-labeled THC sample adduct from aqueous media.

Suitable liquid phase chemical activators that can strengthen the signal generated by the fluorescent-labeled THC adduct's fluorophore include acryloyl species, for example, an acrylate, acrylic acid, acrylic resin or polyacrylate having sufficiently nonpolar side chains to dissolve in nonpolar solvents under the processing conditions. Such species can include acryloyls that are soluble in alkanes, ethers, or combinations thereof at temperatures normally encountered in the field, such as in the range of −40 to 40° C., or any subrange or temperature within that range. For example, the nonpolar organic solvent may include heptane and methyl tertiary butyl ether (MTBE) in proportions from about 15-50% by volume MTBE with the balance heptane, such as 75 vol % heptane and 25 vol % MTBE. And the acryloyl may be a polyacrylate, such as those having 1-10, 1-8, 1-6, 2-10, 2-8 or 2-6 alkyl substituents on the acrylate group, or their corresponding acrylate monomers. Examples include poly(2-ethyl hexyl acrylate) (PEHA) and its corresponding ethylhexyl acrylate (EHA) monomer, and poly (butyl acrylate) (PBA). A specific example is PEHA available from Sigma-Aldrich Co. as P/N 182060 (0.903 g/ml in toluene).

In various implementations, once the fluorophore of the sample adduct, if any, is activated, and the adduct, if any, is isolated from aqueous media in the nonpolar fraction of the solvent extraction, it can then be detected and quantified by optical techniques, for example by exposure to a light source and then measuring the fluorescence of the fluorescent-labeled adduct and determining a quantity of any THC captured from the original breath sample based on the measured fluorescence. In various embodiments, data corresponding to the determined quantity of THC may be wirelessly transmitted to a remote location by any suitable technique.

It should also be understood that breath-testing for THC at the roadside may be combined with breath-testing for alcohol where a portion of the breath sample is tested for blood alcohol content (BAC) according to any suitable BAC analysis, for example by routing through a blood alcohol sensor for ethanol measurement.

In another aspect, a composition having a fluorophore-activated fluorescent-labeled THC-adduct, the adduct dissolved in a nonpolar adduct solution comprising an acryloyl species, is provided. The fluorophore-activated fluorescent-labeled THC-adduct may have the formula: F-N+≡N X⁻·S, wherein F is a functionalized fluorophore, N+≡N is a diazo functional group, X⁻ is a negatively charged ion balancing the charge on the diazo functional group; and S is a diazo functional group stabilizer.

These and other aspects of this disclosure are described and features thereof are illustrated The above implementations are only some of the implementations discussed herein, and do not constitute an exhaustive list of implementations consistent with the scope of this disclosure. Further implementations will be evident from the more detailed discussion provided by the entirety of this disclosure.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIG. 34 depicts an isometric exploded view of the example target substance detection system of FIG. 31 (without the housing).

FIGS. 35 through 37 depicts an isometric view of an example reagent cartridge receptacle assembly for the example target substance detection system of FIG. 31 during various stages of reagent cartridge loading.

FIG. 38 depicts a diagram of a septum and needle configuration.

FIG. 39 depicts an isometric exploded view of the example reagent cartridge receptacle assembly shown in FIGS. 35 through 37.

FIG. 42 depicts an isometric view of an example breath collector module that may be used with the example handheld sample collection unit of FIG. 41.

FIG. 43 depicts an isometric cross-sectional view of the example breath collector module of FIG. 41.

FIG. 44 depicts an isometric exploded view of the example breath collector module of FIG. 41.

FIG. 47 depicts a flow chart showing an example technique for using an example target substance detection system.

DETAILED DESCRIPTION

The analysis/detection systems discussed herein generally employ a luminescence-based approach to measuring the amount of a target substance, e.g., tetrahydrocannabinol (THC), in a person's breath. At a high level, a desired quantity of a person's breath is flowed through some form of catch media, e.g., such as catch media in a small, portable, hand-held device, and then eluted; the resulting elution is then used as the "unknown" sample in the analysis system, and is subjected to one or more mixing, separation, and/or activation operations prior to being optically evaluated to determine an amount of THC that is present in the sample.

Quantitative detection of THC in human breath is challenging due to the extremely low concentration of THC in human breath and the presence of many common, similarly structured contaminants or chemical interferences. As disclosed herein, breath constituents from one or more (e.g., 1-3) exhalations may be captured with a handheld device, and processed and analyzed for roadside analysis.

Chemistry & Technique

Figure 1:
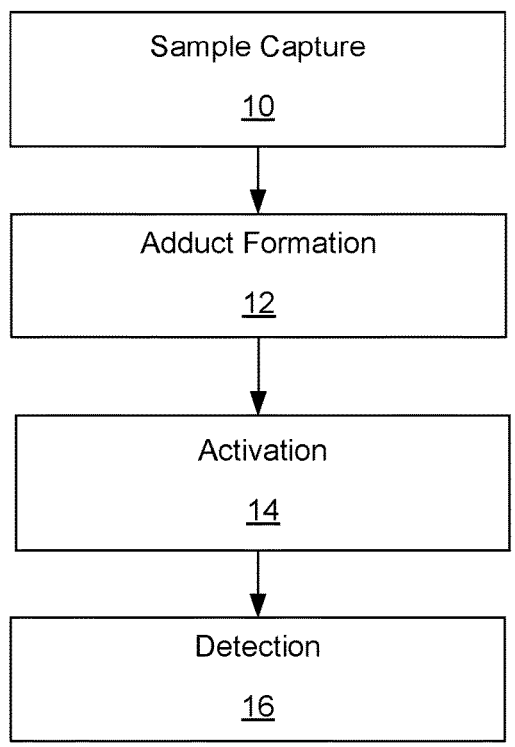
FIGS. 1 and 2 depict process flow charts for methods in accordance with the present disclosure.

FIG. 1 depicts a flow chart showing operations in a general method in accordance with the present disclosure. It should be understood that methods in accordance with this disclosure may be practiced with various permutations, and with or possibly without all of the operations described with reference to FIG. 1, and other operations may be conducted in some embodiments, such as are otherwise described herein, for example.

Referring to FIG. 1, a method of detecting THC in exhaled breath in accordance with one embodiment is shown. The method includes capturing an exhaled breath sample (10), such as by receiving or obtaining, such as from or with a breath capture device or system module, an exhaled breath sample. A fluorescent-labeled sample adduct is then formed with any THC in the captured breath sample in a nonpolar sample adduct solution (12), such as by processing the breath sample such that any THC in the breath sample forms a fluorescent-labeled sample adduct and is dissolved in a nonpolar sample adduct solution. The fluorescent-labeled THC sample adduct's fluorophore is then activated (14), such as by addition of a liquid phase chemical activator, such as an acryloyl species, followed by detecting by determining an amount of THC in the captured breath sample (16), such as by measuring fluorescence of the activated fluorescent-labeled THC sample adduct in the nonpolar sample adduct solution isolated from aqueous media.

Figure 2:
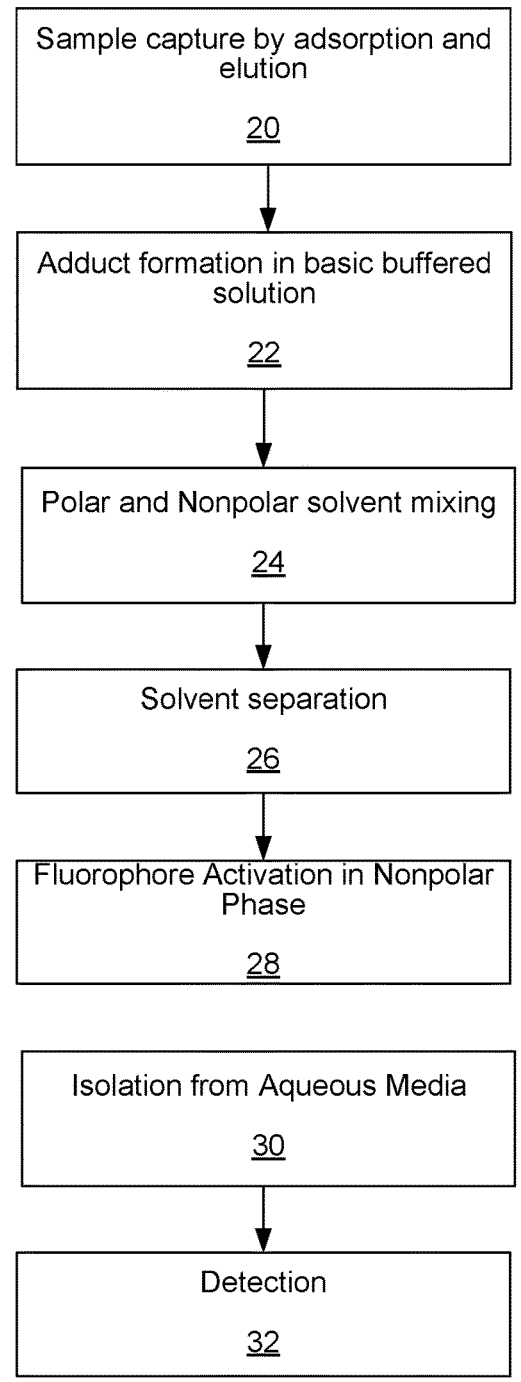

Referring to FIG. 2, a method of detecting THC in exhaled breath characterized as another embodiment is shown. The method includes capturing an exhaled breath sample by adsorption and elution of constituents including any THC on a capture medium, (20), such as by obtaining or receiving an exhaled breath sample with a breath capture device or system module, capturing any THC in the exhaled breath sample by adsorption on and then elution from a capture medium, then forming a fluorescent-labeled sample adduct with any THC in the captured breath sample in a basic buffered sample adduct solution (22), adding to the sample adduct solution a second solvent and mixing to form a mixture containing polar and nonpolar solvents (24), separating the mixture into polar and nonpolar phase layers, the nonpolar layer containing the fluorescent-labeled THC sample adduct (26), activating the fluorescent-labeled THC sample adduct's fluorophore by adding an acryloyl species to the nonpolar phase (28), isolating the fluorescent-labeled THC sample adduct from aqueous media (30), and detecting by exposing the sample adduct in the nonpolar phase to a light source to produce a fluorescence, measuring the fluorescence, and determining a quantity of THC captured and collected from the breath sample based on the measured fluorescence of the sample adduct in the nonpolar phase (32).

The fluorophore can be activated by adding a liquid phase chemical activator into the nonpolar phase of the sample adduct mixture, for example following solvent extraction to separate the sample adduct in the nonpolar phase, or after isolating the solvent-extracted fluorescent-labeled THC sample adduct from aqueous media, for example with a siphon. Suitable liquid phase chemical activators that can strengthen the signal generated by the fluorophore include acryloyl species, for example, an acrylate, acrylic acid, acrylic resin or polyacrylate having sufficiently nonpolar side chains to dissolve in nonpolar solvents under the processing conditions.

In accordance with the embodiments depicted in either FIG. 1 or 2, THC in a breath sample can be captured by adsorption on a catch medium or catch media. The breath sample may be taken, for example, with a handheld device suitable for roadside use, such as are described in further detail in U.S. Patent Application No. 62/337,286, referenced herein below. The catch media may be contained within a breath capture module that includes a mouthpiece into which a subject can exhale a breath sample, a saliva trap downstream of the exhaled breath flow, and a porous medium or media contained in a passage downstream of the saliva trap. The porous catch media may take a number of different forms. For example, the porous media may be composed of discrete granules, beads, or particles that may be retained in the passage by permeable mesh screens or other porous bulkheads. In some implementations, the porous media may include silica microbeads having a size of between 10 microns to 5 mm in size (diameter or maximum dimension). In some implementations, the size of the silica microbeads may be between 400 μm and 1500 μm, or 600 μm and 800 μm or a size of between 800 μm and 1000 μm. In some implementations, the silica beads are longer in one dimension than the other, or cubic, spherical, or cylindrical. In some implementations, the silica microbeads may be packed in a volume of from about from 0.1 mL to 10 mL, For example, in some implementations, the beads are substantially spherical, between 800 μm and 1000 μm in diameter packed in a volume of about 0.5 mL. Performance, including facilitation of adsorbed material recovery from the silica beads in the subsequent elution operation, may be enhanced by washing or otherwise moistening the beads with water prior to capturing a breath sample. Materials other than or in addition to silica may be used as well, including, for example, one or more of filter paper, activated charcoal granules, glass wool, layered mesh screens, or frits, e.g., sintered frits.

THC adsorbed on the catch medium may be eluted from the capture medium using a solvent to form a capture solution. A basic buffer and a diazotized fluorophore solution may then be added to the capture solution to form a fluorescent-labeled THC adduct in a sample adduct solution.

After formation of the sample adduct solution, the fluorescent-labeled THC adduct is separated from polar (e.g., aqueous) components of the sample adduct solution. A second solvent may be added to the sample adduct solution, the resulting mixture mixed, preferably vigorously to obtain short path lengths to expedite the diffusion of the adduct into the nonpolar solvent, and the mixture then allowed to separate into polar and nonpolar phase layers. Any fluorescent-labeled THC-adduct will be contained in the nonpolar layer, and thereby separated by solvent extraction from molecular species that dissolve in polar, but not nonpolar solvents.

In various implementations, the first (elution) and/or second solvents can be organic solvents, the diazotized fluorophore solution is aqueous, and at least one of the first and second solvents is a nonpolar solvent immiscible with water. In some implementations the first solvent is a polar organic solvent miscible with water and the second solvent is a nonpolar organic solvent immiscible with water. Suitable examples of the first polar solvent are alcohols, for example ethanol. Suitable examples of the second nonpolar solvent are alkanes and ethers, or combinations thereof. For example, the nonpolar organic solvent may include heptane and methyl tertiary butyl ether (MTBE) in proportions from about 15-50% by volume MTBE with the balance heptane, such as 75 vol % heptane and 25 vol % MTBE.

In various embodiments, the basic buffer buffers the sample adduct solution to a pH between about 9 and 11, or between about 9.5 and 10, such as 9.87. Suitable examples of the basic buffer include $NaHCO_3$ and $Na_2CO_3$, for example about 60 mol % $NaHCO_3$ and 40 mol % $Na_2CO_3$, although a wide variety of well-known buffers may also be suitable.

Also in various implementations, the added diazotized fluorophore solution is acidic with an acid strength such that the pH of the sample adduct solution remains basic by the action of the basic buffer.

In various embodiments, the diazotized fluorophore has the formula:

$$F-N+{\equiv}N\ X^-\cdot S$$

wherein:
F is a functionalized fluorophore;
$N+{\equiv}N$ is a diazo functional group;
$X^-$ is a negatively charged ion balancing the charge on the diazo functional group; and
S is a diazo functional group stabilizer.

F can be an amine-functionalized fluorophore, such as a primary amine-functionalized fluorophore. The fluorophore can be any one of: xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, and mixtures thereof. In particular examples, the fluorophore is a xanthene, for example a rhodamine, for example rhodamine 123, for example rhodamine 123 diazotized at a primary amine group.

The $F-N+{\equiv}N$ group of a suitable diazotized fluorophore is selected to bind to a cannabinoid. In various embodiments, the $F-N+{\equiv}N$ binds to the para or ortho position of a phenol ring of tetrahydrocannabinol forming an $N{=}N$ azo bond such that an adduct is formed having the formula:

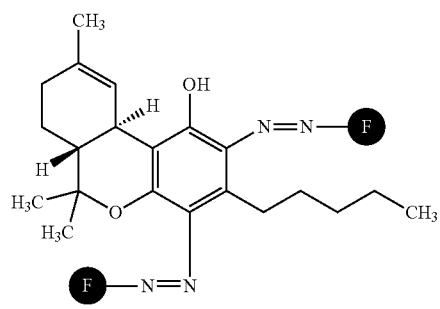

wherein:
F is the functionalized fluorophore, and only one or the other —N≡N-F group is present.

The acidic diazotized fluorophore solution is formed from constituent materials in an acidic solution. For example, the acidic solution may contain dilute HCl, such as 100 μM HCl. Indicators/labels containing stabilized N⁺≡N diazo functional groups can be been synthesized to rapidly (e.g., <2 min) and selectively bind to THC and/or derivatives thereof at the para or ortho position of the phenol ring forming an N═N azo bond. The binding produces a chemically bonded fluorescent-labeled THC adduct. The diazotized fluorophore indicator/label is generally of the form:

where:
F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium seleninde sulfide/zinc sulfide alloy quantum dot, cadmium telluride quantum dot, cadmium sulfide quantum dot, lead sulfide quantum dot, or indium phosphide/zinc sulfide alloy quantum dot derivatives, or any combination thereof;
N⁺≡N is a diazo-functional group that is chemically bonded/grafted/functionalized/conjugated to F;
X⁻ is a negatively charged ion that charge balances the positively charged diazo functional group N⁺≡N, examples of which may include fluoride, sulfide, chloride, nitride, bromide, iodide, arsenate, phosphate, arsenite, hydrogen phosphate, dihydrogen phosphate, sulfate, nitrate, hydrogen sulfate, nitrite, thiosulfate, sulfite, perchlorate, iodate, chlorate, bromate, chlorite, hypochlorite, hypobromite, carbonate, chromate, hydrogen carbonate, dichromate, acetate, formate, cyanide, amide, cyanate, peroxide, thiocyanate, oxalate, hydroxide, or permanganate ion derivatives, or any combination thereof;
S is a N⁺≡N stabilizer, for prevention of decomposition of the diazo compound, composed of salts and/or polymers, examples of which may include tin chloride, cadmium chloride, manganese chloride, zinc chloride, sodium fluoroborate, aromatic, aliphatic, or heterocyclic sulfonic acids, sulfates, and chlorides, polymers with free terminal halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocarbonate ester, amide, amine, ammonium, imine, imide, azide, azo, diazo, cyanate, nitrate, nitrile, nitro, pyridine, thiol, sulfide, disulfide, sulfoxide, sulfone, sulfinic acid, sulfonic acid, camphosulphonic acid, thiocyanate, thione, thial, sulfonyl chloride, carbonyl chloride, phosphine, phosphonic acid, phosphate, phosphodiester, boronic acid, boronic ester, boronic acid, borinic ester, or any combination thereof.

Indicators including stabilized N⁺≡N diazo functional groups can be synthesized, for example, by a process including the combination of a primary amine (—NH₂) functionalized fluorophore, F (listed above), in an acidic solution (H⁺X⁻) with sodium nitrite (NaNO₂) and stabilizers, S (listed above):

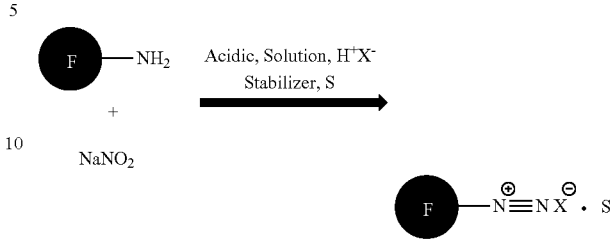

Acidic solutions may include any negatively charged ion X⁻ (such as those listed above) charge balanced with a positively charged hydrogen ion H⁺, in a solvent that has been chosen for suitable or optimal reaction conditions, examples of which include pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, nitromethane, propylene carbonate, formic acid, n-butanol, isopropanol, n-propanol, n-octanol, ethanol, methanol, acetic acid, water, hydrochloric acid, nitric acid, sulfuric acids, propanoic acid, trifluoroacetic acid, perchloric acid, boric acid, p-toluene sulfonic acid, pyridine, methyl isobutyl ketone, isooctane, carbon disulfide, carbon tetrachloride, o-xylene, m-xylene, p-xylene, petroleum ether, heptane, diethyl amine, triethyl amine, tert-butyl methyl ether, tert-butyl alcohol, isobutyl alcohol, methyl ethyl ketone, isoamyl alcohol, diethyl ketone, dimethoxyethane, butyl acetate, 1-chlorobutane, hexamethylphosphorous triamide, 2-ethoxyethyl ether, N,N-dimethylacetimide, ethylene glycol, diethylene glycol, glycerin, diethylene glycol dimethyl ether, 2-methoxyethanol, 2-methoxyethyl acetate, benzonitrile, 1-methyl-2-pyrrolidinone, hexamethylphosphoramide, acetic anhydride, chlorobenzene, propylene carbonate, 1,2-dichloroethane, 1,2-dichlorobenzene, 2,2,2-trifluoroethanol, 1,1,2-trichlorotrifluoroethane, tetrachloroethylene, or any combination thereof.

In various implementations, prior to detecting THC by the exposing the adduct to the light source, the adduct is separated from non-target molecular by phase separation, as described above. For example, a second nonpolar solvent (e.g., 75:25 heptane:MTBE) may be added to the aqueous sample adduct solution (e.g., containing both polar organic solvent and water), the resulting mixture vigorously mixed, and the mixture then allowed to separate into polar and nonpolar phase layers. Any fluorescent-labeled THC-adduct will be contained in the nonpolar phase layer, and thereby separated by solvent extraction from molecular species that dissolve in polar, but not nonpolar solvents.

In various implementations, prior to the exposing the sample adduct to the light source, the fluorophore is activated. Suitable liquid phase chemical activators that can strengthen the signal generated by the fluorescent-labeled THC adduct's fluorophore can be added to the sample adduct solution nonpolar phase. These include acryloyl species, for example, an acrylate, acrylic acid, acrylic resin or polyacrylate having sufficiently nonpolar side chains to dissolve in nonpolar solvents under the processing conditions. Such species can include acryloyls that are soluble in alkanes, ethers, or combinations thereof at temperatures normally encountered in the field, such as in the range of −40 to 40° C., or any subrange or temperature within that range.

For example, the nonpolar organic solvent may include heptane and methyl tertiary butyl ether (MTBE) in proportions from about 15-50% by volume MTBE with the balance heptane, such as 75 vol % heptane and 25 vol % MTBE. And the acryloyl may be a polyacrylate, such as those having 1-10, 1-8, 1-6, 2-10, 2-8 or 2-6 alkyl substituents on the acrylate group, or their corresponding acrylate monomers. Examples include poly(2-ethyl hexyl acrylate) (PEHA) and its corresponding ethylhexyl acrylate (EHA) monomer, and poly(butyl acrylate) (PBA). A specific example is PEHA available from Sigma-Aldrich Co. as P/N 182060 (0.903 g/ml in toluene).

In various implementations, prior to detecting THC by the exposing the adduct to the light source, fluorescence strength of the fluorophore is improved by removing the nonpolar phase from contact with the polar phase following solvent extraction and activation. This isolation of the fluorophore-activated THC adduct from aqueous media can be performed, for example, with a siphon.

Thus, in various embodiments, this disclosure also provides, a method of making a fluorescent-labeled THC-adduct including the operations of combining a primary amine-functionalized fluorophore, sodium nitrite and a diazo functional group stabilizer to form an aqueous solution of a diazo-functionalized fluorophore reactant, the fluorophore reactant solution having an acidic pH; forming a THC solution by dissolving (e.g., by eluting from a breath capture medium) THC in a polar organic solvent; buffering the THC solution by adding a basic buffer to the THC solution; combining the fluorophore reactant solution with the buffered THC solution to form a fluorescent-labeled THC-adduct solution, the adduct solution having a basic pH in the range of about 9-11 (e.g., about 10, such as 9.87); adding a nonpolar solvent (e.g., 75:25 heptane:MTBE) to the adduct solution, mixing and allowing the mixture to separate into polar and nonpolar phase layers whereby any fluorescent-labeled THC-adduct, for example as depicted below:

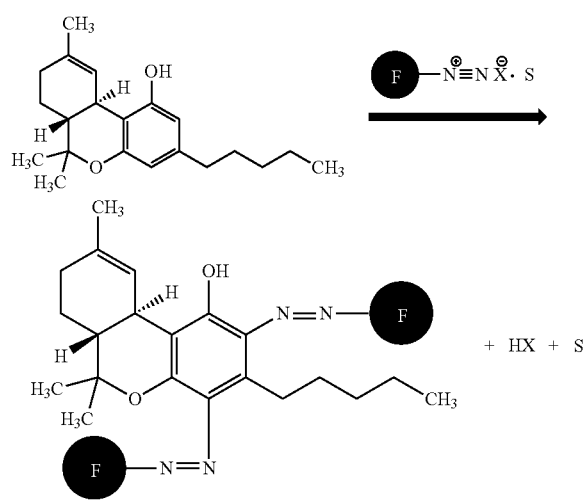

wherein:
F is the functionalized fluorophore, and only one or the other —N=N-F group is present, will be contained in the nonpolar phase, and thereby separated by solvent extraction from molecular species that dissolve in polar, but not nonpolar solvents.

In this way, a fluorophore-activated fluorescent-labeled THC-adduct, the adduct dissolved in a nonpolar adduct solution, is formed.

Returning to the processes of FIGS. 1 and 2, once the sample adduct, if any, is separated, activated, and isolated in the nonpolar fraction of the solvent extraction, it can then be detected and quantified by optical techniques, for example by exposure to a light source and then measuring the fluorescence of the fluorescent-labeled adduct and determining a quantity of any THC captured from the original breath sample based on the measured fluorescence. The detection using optical techniques can be conducted using any suitable technique given the context provided herein. In some implementations, it may be done using an optical measurement sensor that projects an optical beam having a first wavelength range that is selected so as to stimulate emission of light having a second wavelength range from the THC adduct. The emitted light may then be collected by the same optics used for projection and routed to a photodetector in the optical measurement sensor for quantification. A photoemitter may be located so as to direct light along a first axis and a photodetector may be configured to receive light received along a second axis that is orthogonal to the first axis. A beam splitter, e.g., a window that is generally reflective to the first wavelength range but generally transmissive to the second wavelength range, may be located at the intersection of the first axis and the second axis, and may be positioned at a 45° angle to both axes so as to cause light from the photoemitter to be turned 90° and directed out of the optical measurement sensor to form the optical beam. At the same time, light that is emitted by the THC adduct in response to stimulation by the light of the first wavelength range may pass through the beam splitter without being reflected and thus be received by the photodetector. When measurement of the amount of THC adduct present in a sample is desired, the photoemitter may be turned on so that light of the first wavelength range is emitted to optically pump or stimulate the THC adduct; the light of the second wavelength range that is emitted by the THC adduct in response may then be measured by the photodetector, and the intensity of such detected light may be correlated with an amount or concentration of THC adduct (and thus THC) that is present in the sample. It is to be understood that other types of optical sensors may be used as well, and that some optical sensors may, depending on the particular adduct used, not include a photoemitter, e.g., in implementations where the THC adduct does not require optical pumping in order to emit light. In various embodiments, data corresponding to the determined quantity of THC may be wirelessly transmitted from the detection location to a remote location by any suitable technique.

Detecting by determining an amount of THC in the captured breath sample based on the measured fluorescence of the isolated and activated fluorescent-labeled THC sample adduct can be accomplished by exposing the sample adduct in the nonpolar phase to a light source to produce a fluorescence, measuring the fluorescence, and determining a quantity of THC captured and collected from the breath sample based on the measured fluorescence of the sample adduct in the nonpolar phase. In various embodiments, determining the quantity of THC based on the measured fluorescence of the sample adduct in the nonpolar phase involves comparing the fluorescence of the sample adduct in the non-polar phase to the fluorescence of one or more standard positive and/or negative controls. This can be accomplished by adding to one or more standard/control/calibration THC solutions containing a known amount of THC (including, in the case of a negative control, no THC), the basic buffer and the aqueous diazotized fluorophore solution to form one or more fluorescent-labeled THC standard adducts in standard adduct solutions. The standard adduct solutions are then processed in the same manner as the sample adduct solution, for example in each case adding to the standard adduct solution the nonpolar organic solvent and mixing, and separating the mixture into polar and nonpolar phase layers, wherein the nonpolar layer contains the fluorescent-labeled THC standard adduct, if any. In various embodiments, these standard (control or calibration) adduct solutions are prepared in parallel with the sample adduct solution, and using the same reagents to minimize variation. In particular, the sample and standard adduct solutions can be prepared using the same diazotized fluorophore solution added to each control THC solution, since it can be difficult to prepare diazotized fluorophore solutions consistently. Thereafter, the standard adduct solutions may be subjected to the same detection procedure as the sample adduct. Comparisons of the fluorescence measurements of the standards and the sample can facilitate more accurate determination of a quantity of THC captured and collected from a breath sample.

It should also be understood that breath-testing for THC at the roadside may be combined with breath-testing for alcohol where a portion of the breath sample is tested for blood alcohol content (BAC) according to any suitable BAC analysis. In various embodiments, the breath sample obtained from the subject is also tested for a second substance, in particular ethanol, such that both THC and ethanol are measured from the same breath sample. According to such embodiments, a portion of the breath sample may be routed through a blood alcohol concentration (BAC) sensor for ethanol measurement. BAC sensors, including calorimetric, capacitive and others, and their operation are well known in the art. Briefly, in a typical example of a fuel call-based BAC sensor, when a subject exhales into a breath analyzer, any ethanol present in their breath is oxidized to acetic acid at the anode. At the cathode, atmospheric oxygen is reduced. The overall reaction is the oxidation of ethanol to acetic acid and water. The electric current produced by this reaction is measured by a microcontroller, and displayed as an approximation of overall blood alcohol content (BAC). Blood alcohol content or concentration is not measured directly, which would require the analysis of a blood sample. Instead, a BAC sensor determines BAC indirectly by measuring breath alcohol level. Any suitable BAC sensors may be integrated with a device associated with the test cartridge, for example fuel cell based sensors from PAS Systems, Inc.

EXAMPLES

Example 1 provides data from experiments evaluating fluorophore chemical activator species. Example 2 provides a workflow summary of a benchtop protocol for THC detection in accordance with the present disclosure that may be used or adapted for use in roadside detection and quantification of THC obtained from a breath sample taken using a handheld device. These examples are provided to exemplify and more clearly illustrate aspects of the present disclosure, and/or provide proof-of-concept, and are in no way intended to limit the scope of the coverage provided by this application to the specific details described.

Example 1

Figure 3:
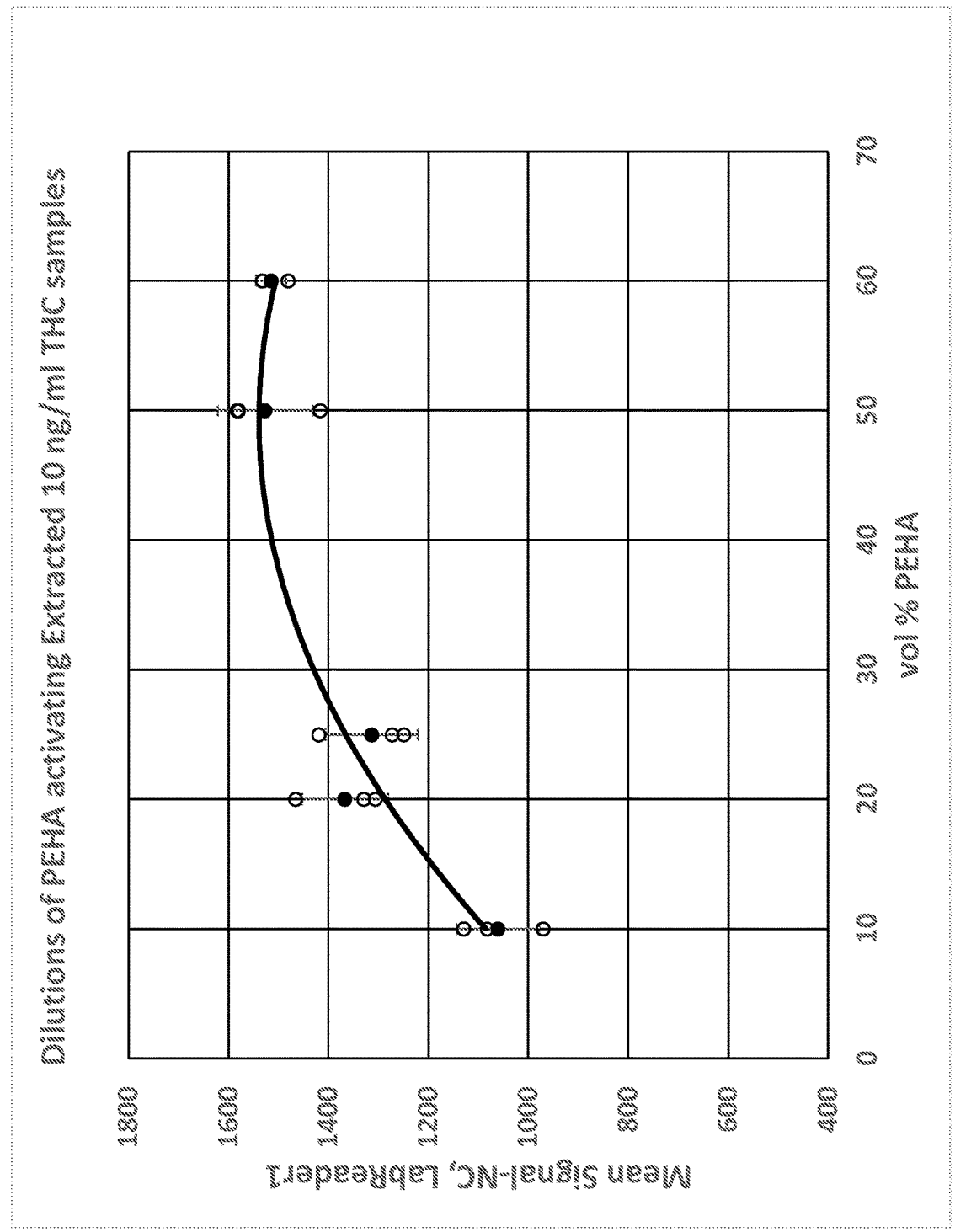
FIG. 3 depicts a plot showing activation of a fluorescent-labeled THC adduct's fluorophore achieved by poly(2-ethyl hexyl) acrylate at various dilutions.
Figure 4:
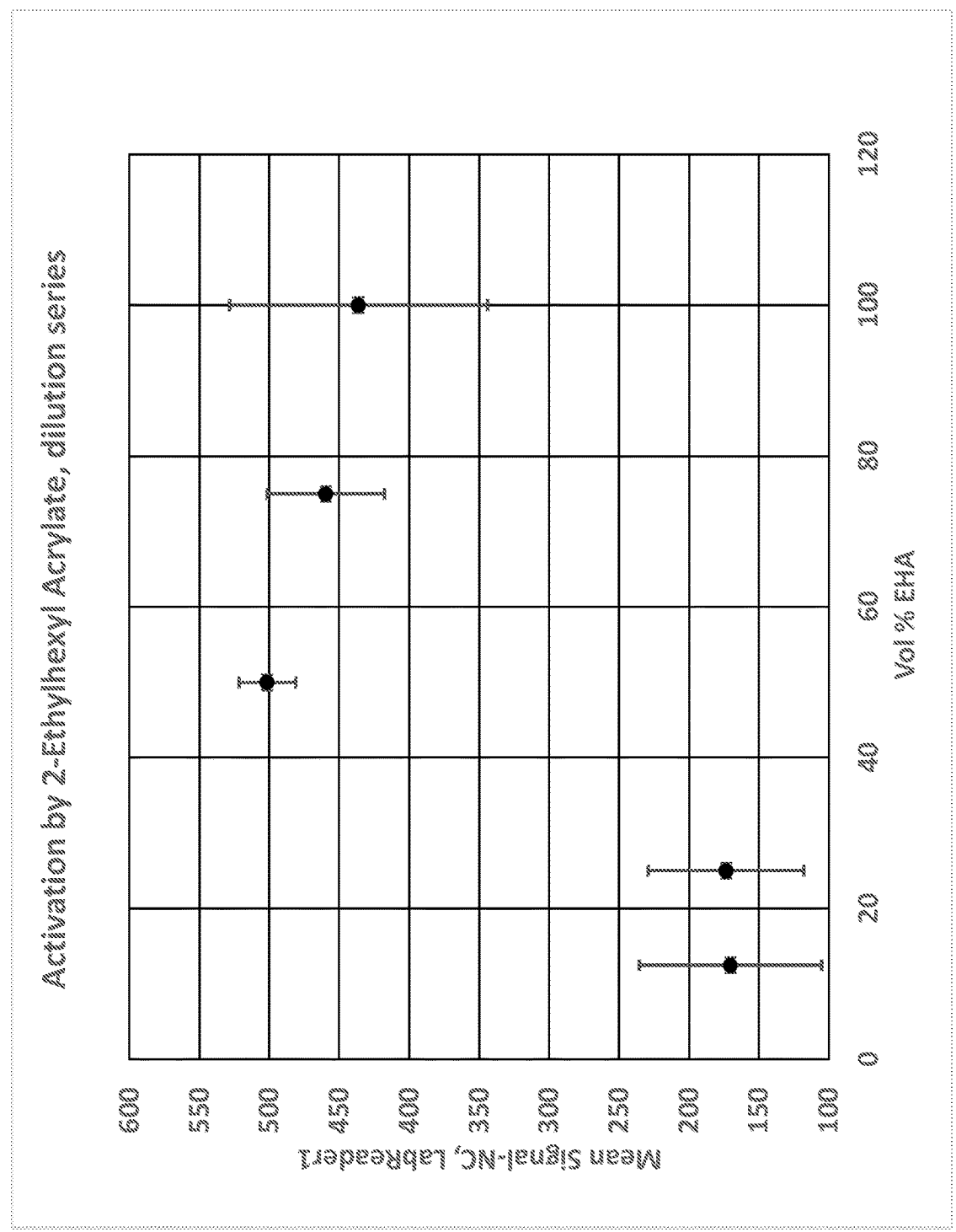
FIG. 4 depicts a plot showing activation of a fluorescent-labeled THC adduct's fluorophore achieved by 2-ethyl hexyl acrylate at various dilutions.

Experiments were performed to determine the effectiveness of the polyacrylate include poly(2-ethyl hexyl acrylate) (PEHA) and its corresponding monomer ethylhexyl acrylate (EHA) as fluorophore activators. PEHA and EHA samples were obtained from Sigma-Aldrich Co., 0.903 g/ml in toluene. Triplicate samples of 10 ng/ml fluorescent-labeled THC adduct were activated with 200 ul of each concentration of the original dilution series. FIG. 3 depicts a plot showing activation of a fluorescent-labeled THC adduct's fluorophore achieved by poly(2-ethyl hexyl) acrylate at various dilutions. FIG. 4 depicts a plot showing activation of a fluorescent-labeled THC adduct's fluorophore achieved by 2-ethyl hexyl acrylate at various dilutions.

Activation by EHA can be seen, with the optimal concentration being around 50%. However the EHA level of activation is much lower than that achieved with the corresponding polymer, PEHA (signal is about 38% of that achieved with PEHA). Therefore, the polyacrylate appears to be the more effective fluorophore activator from the experiments to date.

Toluene itself does not appear to cause any activation in concentrations of 50%, 25%, and 12.5% by volume (remainder is heptane:MTBE).

Example 2

Materials

Glass vials for all reaction chemistries and to hold all buffers and intermediates
  2 mL or 4 mL (TBD) glass vials for mixing chambers (mimics automated system)
  4 mL glass vials acceptable for separated solvent with THC (post solvent extraction)
  20 mL glass vials for batch processing if desired
P1000 μL pipettor and 1000 uL pipette tips
Lab Reader #1
  Glass pipettes for mixing and cleaning
  non-RPT pipette tips (TBD blue box)
Lab Reader #2
  2×2.5 mL glass syringes+2× PTFE tube fittings for each
  4×20 mL glass vials filled with EtOH (refilled as needed)
Scale (measurement accuracy and precision <0.1 mg)
Solvents:
  EtOH
  Organic solvent
    MTBE (25% v/v)
    Heptane (75% v/v)
  THC in EtOH
  Activator
PEHA (25% in toluene, density 0.903 g/ml, as stated by Sigma)
Buffers: acidic (100 uM HCl) and basic buffer (20 mM $NaHCO_3$ and 13 mM $Na_2CO_3$—pH 9.87)
Reagents: Mix C (Rhodamine, CSA, sodium nitrite mixture)
Magnetic stir bars (if needed): PTFE 10×3 mm micro stir bars (SBM-1003-MIC www.stirbars.com)

Lab Readers
  #1: Top load cuvette
  #2: Bottom load flow cell
Air or nitrogen cylinder for drying sample cuvette Chemistry Reaction Protocol (Solvent Extraction Protocol is Per Sample)

1. Creating controls and samples
   a. Pipette necessary ratio of THC:EtOH to reach a final volume of 250 uL at desired concentration in "mix chamber vials" (nominally 2 mL to mimic automated assay)
      i. Assay typically ranges from 0 to 5 ng THC (0 to 20 ng/mL)
   b. Add 500 uL of buffer solution (20 mM $NaHCO_3$ and 13 mM $Na_2CO_3$)—pH 9.87
   c. Mix by hand with shaking or with stir bar
2. Preparing diazonium fluorophore
   a. In separate vial, measure 1.0+/−0.2 mg Mix C (Rhodamine, CSA, sodium nitrite mixture)
   b. Add 250 uL of 100 uM HCl to Mix C powder
   c. Mix and allow to stand for at least 5 minutes (if not actively mixing)
   d. Protect from light (e.g., in dark box)
3. Creating the THC-adduct
   a. Add 250 uL of Mix C solution to THC:EtOH solution
   b. Mix and allow to stand for at least 5 minutes (if not actively mixing)
4. Solvent extraction to isolate THC-adduct product
   a. In a separate vial, prepare at least 1 mL of 75:25 Heptane:MTBE
   b. Add 750 uL of 75:25 Heptane:MTBE solution
   c. Mix
      i. 2 mL vials
         1. Vortex 10 seconds
         2. Mix with 10 mm stir bar at 1640RPM for 30 seconds
      ii. 4 mL vials
         1. Vortex 5 seconds
         2. Mix with 10 mm stir bar at 800 RPM for 30 seconds
   d. Carefully pipette 500 uL from top layer of solution and transfer to separate glass vial (4 mL vial OK); DO NOT TAKE ANY OF THE BOTTOM LIQUID.

Optical System Procedure

1. Turn on power to detector for at least one hour prior to any testing
2. Measure a few boluses of 100% EtOH to ensure a stable baseline
3. Record optical signal (V)
4. Lab Reader #1 (needs at least 580 uL sample volume to have meniscus over optical beam spot)
   a. Remove as much EtOH as possible using a glass Pasteur pipette and dry cuvette with compressed air for 10 seconds—Check cuvette visually
   b. Activation and sample measurement
      i. Add 200 uL of dilute activator into cuvette using P1000 or P200 pipettor (70% of the 200 ul is PEHA (which is at about 25% in toluene, density 0.903 g/ml, as stated by Sigma))
      ii. Start data capture using Hyperterminal program
      iii. Reset pipettor to 500 uL if using single P1000 or use separate P1000 pipettor
      iv. Start LED cycling (file collection now starts)
      v. Add 500 uL of sample into cuvette using pipettor, cover with black cloth and continue to capture data for 5-10 seconds
      vi. Turn off LED
      vii. From data file, record peak signal (ignoring spurious spikes from initial fluid transfer into cuvette)—note that signal will decay due to photo effects
   c. Remove as much fluorescent sample as possible using a glass Pasteur pipette
   d. Dispose of contaminated glass Pasteur pipette and use new glass Pasteur pipette
   e. Add about 1 mL of 100% EtOH into cuvette and pipette up and down to rinse cuvette using a glass Pasteur pipette
   f. Remove EtOH and add 1 mL of 100% EtOH
   g. Record signal from EtOH to ensure return to EtOH baseline
   h. Repeat steps a-g as needed to measure all samples
5. Lab Reader #2
   a. Remove as much EtOH as possible using a glass syringe and dump to waste
   b. Remove plunger
   c. Dry syringe, plunger and PTFE fitting/tubing with compressed air
   d. Reassemble syringe
   e. Dry cuvette with compressed air at 10 psi for 20 seconds—Check lines visually
   f. Dry flow cell input fitting with compressed air
   g. Activation and sample measurement
      i. Transfer 200 uL activator to an intermediate 2 mL or 4 mL vial
      ii. Pull the 200 uL of diluted activator into 2nd syringe and PTFE fitting/tubing (used only for dilute activator=activator syringe)
      iii. Remove PTFE fitting from activator syringe
      iv. Push 200 uL of dilute activator into flow cell
      v. Close input valve
      vi. Cover flow cell with black cloth
      vii. Remove activator syringe
      viii. Pull 500 uL of sample into clean syringe using clean PTFE fitting
      ix. Remove PTFE fitting
      x. Attached sample syringe to flow cell input fitting
      xi. Open input valve
      xii. Add the 500 uL of sample into the flow cell using the syringe
      xiii. Take measurement to record the measured signal
   h. Remove as much fluorescent sample as possible using attached glass syringe and dump sample to waste
   i. Reattach contaminated PTFE fitting to syringe
   j. Rinse syringe with PTFE fitting with 3 serial washes of about 1 mL EtOH in 3 20 mL vials (dumping to waste)
   k. Remove (now clean) PTFE fitting
   l. Pull in 1 mL 100% EtOH into (now clean) syringe
   m. Add 1 mL of 100% EtOH into the flow cell to rinse flow cell using the glass syringe
   n. Titurate 3× to rinse flow cell
   o. Remove EtOH using syringe and dump to waste
   p. Rinse syringe with 3 serial washes of ~1 mL EtOH in 3 20 mL vials (dumping to waste)
   q. Pull 1 mL of clean EtOH into the glass syringe
   r. Add 1 mL of 100% EtOH to flow cell using the glass syringe s. Record signal from EtOH to ensure return to EtOH baseline t. Repeat steps a-s as needed to measure all samples It is to be understood that the above-described methods may be implemented in a number of different ways, and that such different implementations are also considered within the scope of this disclosure.

Analysis System

Figure 5:
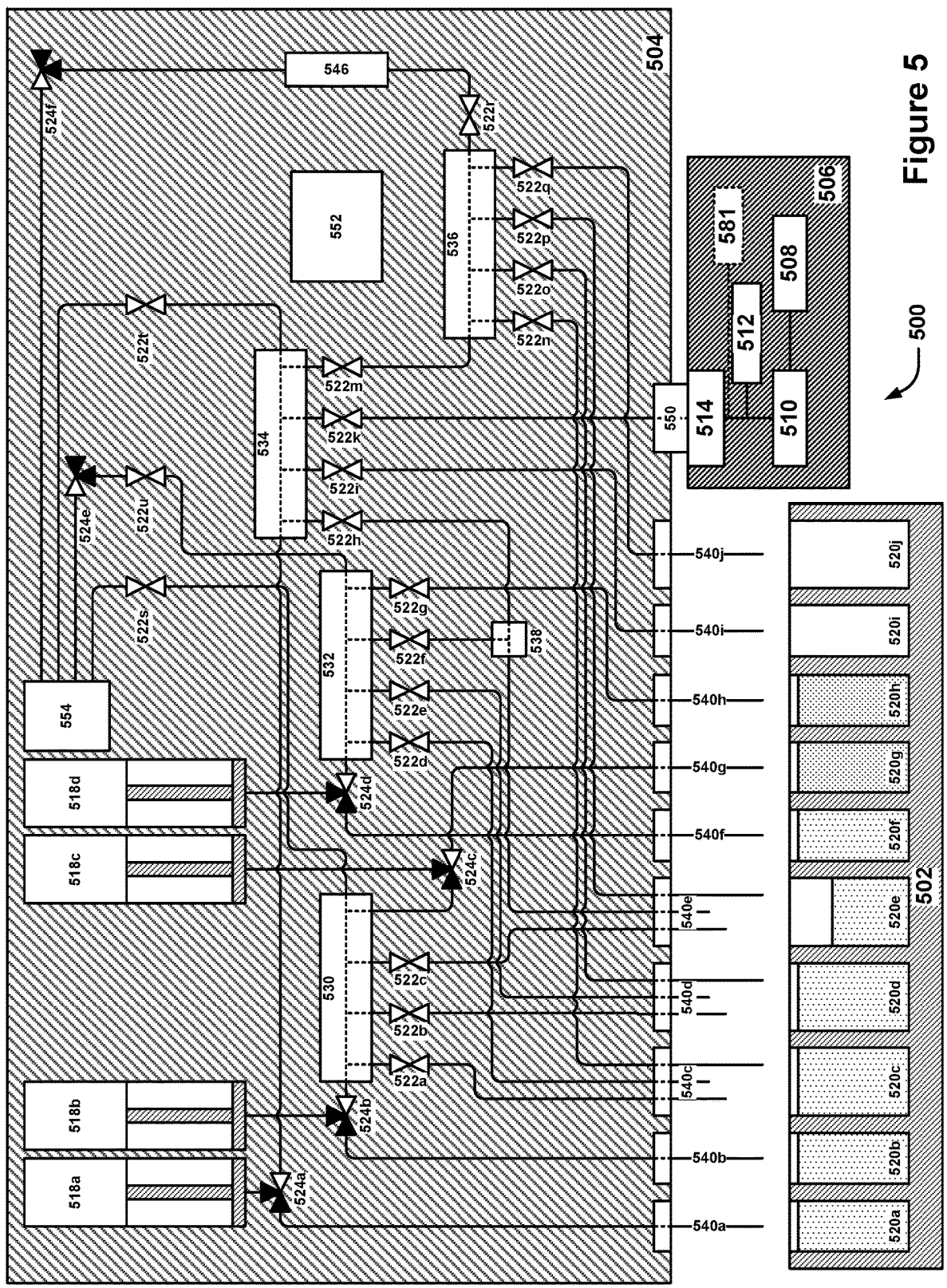
FIG. 5 depicts a schematic of another example target substance analysis system.

FIG. 5 depicts a schematic of an example target substance analysis system that is discussed in more detail herein and that may be used to perform analyses and techniques such as those discussed above. The example target substance analysis system of FIG. 5 is configured to facilitate the detection of THC in a person's breath, thereby allowing for "Breathalyzer®" type testing for people suspected of being under the influence of THC. As will be appreciated from the following discussion, the detection of THC in a breath sample may involve a number of different steps, and it is to be understood that while these steps are described with respect to a particular embodiment of a THC analysis system, other embodiments falling within the scope of this disclosure may operate differently from the specific examples discussed but may nonetheless still fall within the scope of the disclosure. The example of FIG. 5 differs from that shown and discussed, for example, in U.S. patent application Ser. No. 15/217,264, which is hereby incorporated herein by reference in its entirety, in that the reagents that are used are housed in a removable cartridge while the pump mechanisms are located in the analysis system, there are multiple mixing chambers instead of a single mixing chamber, and a liquid activator may be used to activate the fluorescent adduct that is produced by mixing of the indicator and THC. Other differences also exist, and this recitation of differences is not to be considered exclusive of other differences that may be apparent from this disclosure.

The target substance analysis system of FIG. 5 includes an analysis unit 500 that has a base station 504, a reagent cartridge 502, and a handheld sample collection unit 506. As shown in FIG. 5, the reagent cartridge 502 may be stored separately from the base station 504 or, alternatively, may be stored in the base station 504 but without being engaged with the fluidic interfaces of the base station 504. The reagent cartridge may have a number of interior volumes forming mixing chambers and/or reservoirs within it.

For example, the reagent cartridge 502 in FIG. 5 includes an eluent reservoir 520*a*, an organic solvent reservoir 520*b*, a negative control mixing chamber 520*c*, a positive control mixing chamber 520*d*, a sample mixing chamber 520*e*, an indicator solvent reservoir 520*f*, an activator reservoir 520*g*, an indicator mixing chamber 520*h*, a sample reservoir 520*i*, and a waste reservoir 520*j*.

It is to be understood that the reagent cartridge 502 may, in some embodiments, be split into multiple pieces, e.g., the mixing chambers may be in one cartridge and the other reservoirs may be located in another cartridge. For ease of use and reduction of the chance of potentially mixing up reagents/mixing chambers/reservoirs, the implementation disclosed in FIG. 5 collocates all of the mixing chambers, reservoirs, and reagents in one common cartridge. However, the various reagents and interior volumes used may be split apart in any desired manner. For example, in some implementations, some of the reagents that that may have a longer shelf-life or may not need to be preserved for evidentiary purposes may be housed in a cartridge with larger reservoirs (or even housed in a permanent reservoir of the base station 504 that is refilled directly from a reagent source). For example, the indicator solvent, eluent, and organic solvent may, in some implementations, be stored separately from the reagent cartridge, e.g., in a separate reagent cartridge that may be used for multiple analysis runs before needing to be replaced or in permanent reservoirs in the analysis unit. In the most extreme case, each reservoir or mixing chamber may be housed in a separate cartridge and be separately installable in the base station 504.

It is also to be understood that some reservoirs and/or mixing chambers may be omitted in some implementations. For example, the sample reservoir 520*i* may be omitted if it is not desired to retain any portion of the sample that is not used. Similarly, the waste reservoir 520*j* may be omitted if waste fluids are simply allowed to exit the base station 504 via a drain, or otherwise disposed of.

The other removable component of the analysis unit 500 that is depicted is the handheld sample collection unit 506, which is shown connected to the base station 504 in FIG. 5. The handheld sample collection unit 506 may include a breath capture module (or breath collector module) (BCM) 514 (also referred to as "catch media" in some circumstances) that is connected with a saliva trap 510 and a mouthpiece 508 such that when a person blows through the mouthpiece 508, the exhaled breath passes through the mouthpiece 508 and then through the saliva trap 510 before passing through the BCM 514. The BCM may, for example, be a BCM such as is described in U.S. Patent Application No. 62/337,286, filed May 16, 2016, which is hereby incorporated by reference in its entirety. In some implementations, the mouthpiece 508, the saliva trap 510, and/or the BCM 514 may be a single piece. For example, the saliva trap 510 and the mouthpiece 508 may be a single-piece, commercial-off-the-shelf combination mouthpiece/saliva trap such as may be used with Breathalyzer® test units. In fact, in some implementations, the handheld sample collection unit 506 may additionally or optionally include a blood alcohol concentration (BAC) sensor 581, which may be fluidically connected with the mouthpiece 508/saliva trap 510 in a manner similar to the pressure sensor 512 (see discussion below) so that a portion of the exhaled breath passing through the handled sample collection unit 506 is diverted to the BAC sensor 581 to allow a BAC measurement to be obtained during sample collection. The results/measurements from the BAC sensor 581 may be stored, e.g., for later transmission to the base station (or other device), and then combined with whatever the results are from a THC analysis performed by the base station into a single result set later on. See, for example, the disclosures of U.S. patent application Ser. No. 14/997,405 and U.S. Provisional Patent Application Nos. 62/104,813; 62/107,331; and 62/277,854 for further details of such arrangements (all of which are previously incorporated by reference herein). The BAC sensor 581 is shown in FIG. 5, but is omitted in later Figures (it may be assumed to be present, however, in implementations that include it).

The BCM 514 may be designed to be relatively lightweight and may have features, such as catch media, that are configured to promote the capture of breath constituents from a person's breath as the person exhales through the handheld sample collection unit 506. In some implementations, the handheld sample collection unit 506 may include a BCM 514 that includes catch media having a plurality of microbeads or microspheres, as discussed in U.S. Patent Application No. 62/337,286, that are sandwiched between and retained by two mesh screens. In some such implementations, a woven or fibrous filter media or membrane may be interposed between each mesh screen and the microbeads or microspheres; such a woven or fibrous filter media or membrane may provide further surface area onto which breath constituents may adsorb during sample collection and may enhance the ability of the BCM 514 of the handheld sample collection unit 506 to capture useful samples. For example, in some implementations, the BCM 514 of the handheld sample collection unit 506 may include one or more layers of filter media such as Technostat® 90 Plus, which is a meltblown synthetic fiber carried on a spunbond polypropylene backing material. Technostat® 90 Plus is manufactured by Hollingsworth & Vose of East Walpole, Massachusetts, and is distributed in the United States of America by Superior Felt & Filtration of McHenry, Illinois, at the time of this writing. In implementations utilizing Technostat® 90 Plus or a similar filter media, the BCM 514 of the handheld sample collection unit 506 may, in some instances, omit additional filter media such as microbeads and instead rely on one or more layers of the filter media. In some such implementations, the filter media may be sandwiched between mesh screens to provide support to the filter media and to prevent the filter media from getting dislodged. In other such implementations, the filter media may not be sandwiched between mesh screens but may be clamped in place directly, e.g., about the periphery of the filter media.

The handheld sample collection unit 506 may also include electronics (not shown), such as one or more processors and a memory storing instructions for controlling the one or more processors, that may control or monitor operation of the handheld sample collection unit 506 and provide information regarding the progress of the sample collection using the handheld sample collection unit 506. For example, the handheld sample collection unit 506 may include a pressure sensor 512 that has a pressure measurement port that is interposed between the saliva trap 510 and the BCM 514 so as to monitor the pressure downstream of the saliva trap 510 and upstream of the BCM 514. The one or more processors may monitor the data from the pressure sensor and determine therefrom the amount of air that is blown into the mouthpiece 508, through the saliva trap 510, and then delivered to the BCM 514. When the amount of exhaled breath that passes through the handheld sample collection unit 506 exceeds a predetermined amount (as determined from the pressure sensor data, or from another sensor providing similar information), e.g., 3 liters, then the one or more processors may cause a signal to be provided that a sufficient sample has been collected, e.g., the handheld sample collection unit 506 may be caused to emit a "beep" or provide some other sort of indication that a sufficient sample has been collected.

The handheld sample collection unit 506 may be docked with the base station 504 such that the BCM 514 interfaces with an elution port 550 on the base station 504. The elution port 550 may seal to the BCM 514 to form a liquid-tight interface so that the eluent from the eluent reservoir 520a may be delivered to the BCM 514 for elution of any breath constituent samples that are adsorbed onto the catch media therein.

The base station 504 may contain the non-disposable and/or non-handheld portions of the analysis unit 500. For example, the base station 504 may include a plurality of valves, such as binary (on/off) valves 522a-522u (the use of a lower-case "L" callout suffix was avoided to prevent confusion with the number "1"; the lower-case "J" callout suffix was inadvertently omitted) and/or 3-way valves 524a-524f, that may be configured to provide for controllable fluidic flow between various other components of the base station 504, the reagent cartridge 502 (when docked), and the handheld sample collection unit 506 (when docked), one or more pumps, such as pumps 518a-518d, that may be operable to move fluids through the analysis unit 500, an optical measurement chamber 546 and corresponding optical measurement device 552, and one or more air pumps 554. The pumps 518a-518d may, for example, be metering pumps, such as linear-actuator-driven syringe pumps. The flow paths between these components may be provided by way of flexible tubing, rigid manifolds, or combinations thereof. For example, in the example implementation, four large manifolds (an activator manifold 530, an indicator manifold 532, an elution manifold 534, and an optics manifold 536) and one smaller manifold (a T manifold 538) are used, in conjunction with various valves 522 to allow for controllable switching between flow paths. It is to be understood that junctions between the various flow paths discussed herein may be provided using any suitable combination of components. For example, a six-port manifold may be formed by joining together two four-port cross-shaped manifolds, or a five-port manifold may be formed by joining together a 3-port T manifold and a 4-port cross-shaped manifold. In some implementations, one or more of the valves may be integrated into the manifolds.

The base station 504 may also include a plurality of fluidic interfaces 540, including, for example, an eluent fluidic interface 540a, an organic solvent fluidic interface 540b, a negative control fluidic interface 540c, a positive control fluidic interface 540d, a sample fluidic interface 540e, an indicator solvent fluidic interface 540f, an activator fluidic interface 540g, an indicator fluidic interface 540h, a sample overflow fluidic interface 540i, and a waste fluidic interface 540j. The fluidic interfaces 540 may be any fluidic interfaces that, for example, allow a component having an internal volume, e.g., a reservoir or a mixing chamber, to be connected or interfaced to the fluidic interface in order to allow fluids to be withdrawn from, or introduced into, the internal volume.

One example of a fluidic interface that may be used is one or more hollow needles or probes that may pierce a septum or seal on a reservoir or mixing chamber when the septum or seal of the reservoir or mixing chamber is aligned with the needles or probes and the reservoir or mixing chamber is then translated towards the fluidic interface along a direction generally parallel to the needles or probes. Some other types of fluidic interfaces that may be used include, for example, quick-release fittings, o-ring sealed ports, threaded fittings, etc. The fluidic interfaces may be hermetic interfaces or may be non-hermetic, depending on the requirements of the pumping and fluid movement mechanisms used.

Operation of the analysis unit of FIG. 5 is discussed below with reference to further Figures. In the following Figures, valves may be depicted using a "bowtie" symbol, e.g., two or three triangles arranged about a point with a point of each triangle coincident on a common center point. When triangles associated with a valve symbol are colored black, this indicates that the valve is open or that the valve permits flow through the ports represented by those black triangles. It should be noted that valves may be indicated as open in some diagrams but may also be closed (for example, a valve that controls fluid flow along a fluid flow path that does not have any fluid flowing through it or that is not pressurized may be either open or closed without changing the flow condition of that flow path). Another convention that is used in these Figures is to emphasize fluid flow paths that see liquid flow in the operational stage represented by a particular diagram by bolding/thickening the lines representing those fluid flow paths in that diagram. For fluid flow paths that may see air flow, such lines may be emphasized using heavy dotted lines.

Figure 6:
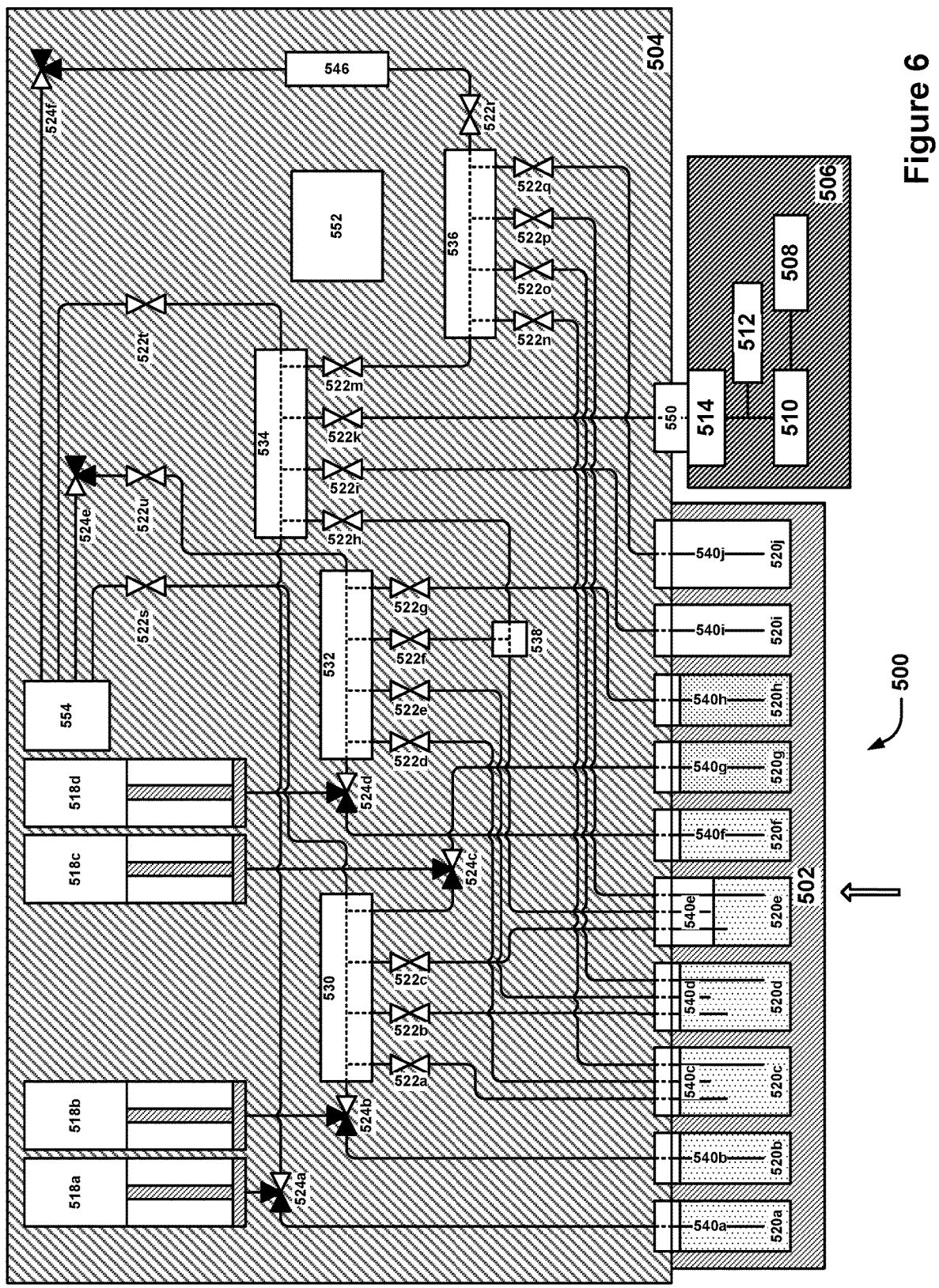
FIG. 6 depicts a schematic of the example target substance analysis system of FIG. 5 during a cartridge loading operation.

FIG. 6 depicts a schematic of the example target substance analysis system of FIG. 5 during a cartridge loading operation. In the cartridge loading operation, the reagent cartridge 502 may be inserted into the base station 504 and the fluidic interfaces 540 may each be interfaced with their respective mixing chambers or reservoirs 520. In some implementations, the loading of the reagent cartridge 502 may cause a sensor to register the insertion of the reagent cartridge 502, which may cause a controller of the analysis unit 500 to initiate certain actions. For example, the controller of the analysis unit 500 may cause the handheld sample collection unit 506 to turn on, or may cause a lock or latch securing the handheld sample collection unit 506 to be released to allow the handheld sample collection unit 506 to be removed. In some implementations, insertion of the reagent cartridge 502 may cause the analysis unit 500 to turn on and boot up.

Figure 7:
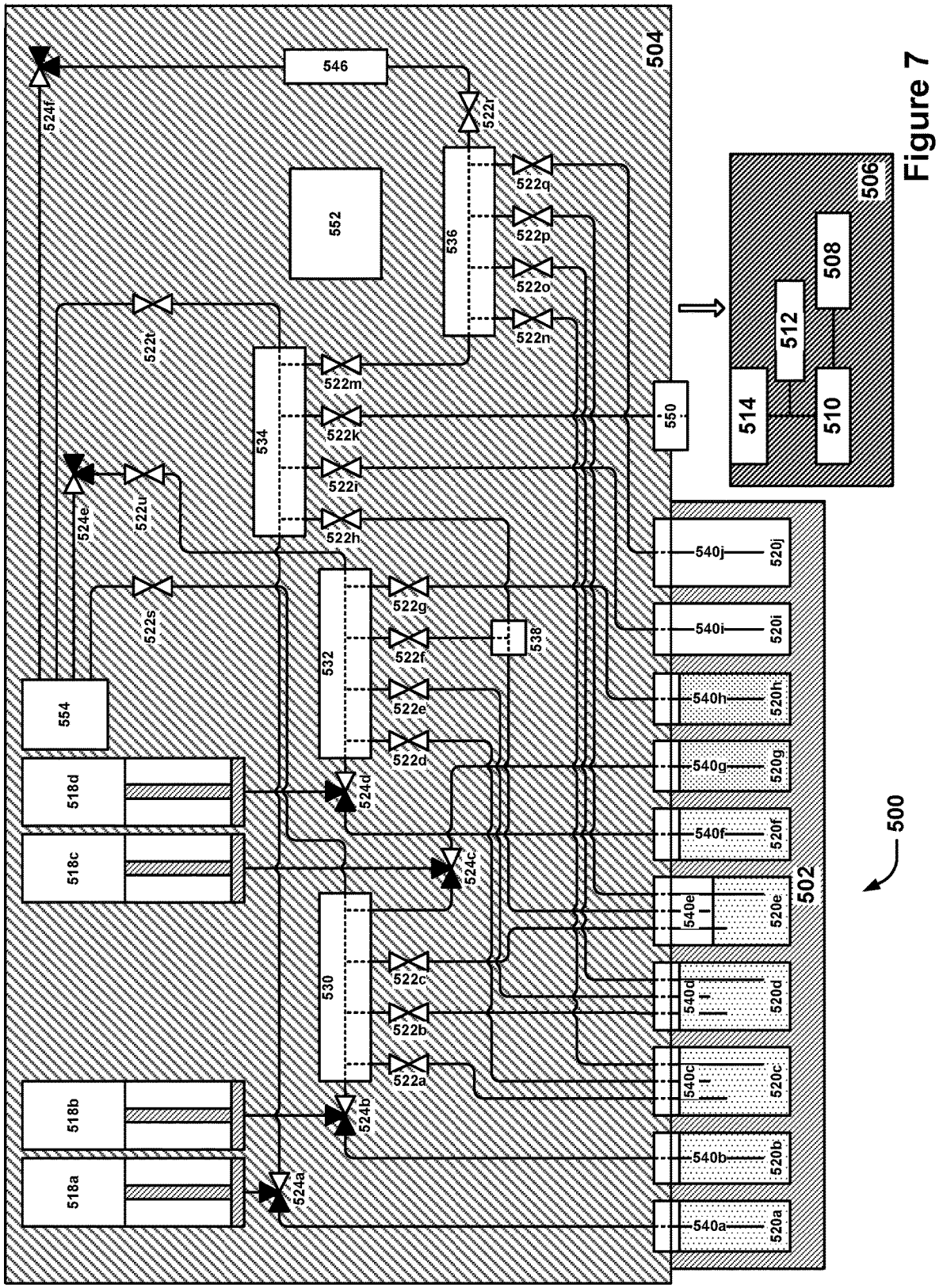
FIG. 7 depicts a schematic of the example target substance analysis system of FIG. 5 during removal of a handheld sample collection unit.

FIG. 7 depicts a schematic of the example target substance analysis system of FIG. 5 during removal of a handheld sample collection unit. The handheld sample collection unit 506 may, for example, be stored on the base station 504 during analysis operations and also stored on the base station 504 for long-term storage, e.g., in between analyses. Thus, in some implementations, removal of the handheld sample collection unit 506 may be used as an indicator that a sample collection is being initiated and that sample analysis may be imminent. For example, a sensor may be configured to detect when the handheld sample collection unit 506 is removed from the base station 504. In response to information from such a sensor indicating that the handheld sample collection unit 506 has been removed, the controller of the analysis unit 500 may, in some implementations, begin preparing reagents for a subsequent analysis. For example, in implementations where limited shelf-life reactants are used, such as diazo-functionalized solid-phase reactants that are then dissolved into a solvent to provide a diazo-functionalized liquid reactant (the solid phase may be relatively stable, but once mixed with the solvent, the shelf life of the resulting mixture may see significant degradation in potency in a relatively short window of time, e.g., within hours to tens of hours), it may be advantageous to prepare the limited shelf-life reactants only if analysis is anticipated in the near future. Thus, in some implementations, the controller may be configured to initiate preparation of one or more of the reactants on receipt of a signal indicating that sample collection preparation has begun. For example, in some implementations, a signal indicating that the handheld sample collection unit 506 has been removed from the base station 504 may cause the controller to initiate the preparation of such reagents. In other implementations, powering on the handheld sample collection unit 506 may cause the handheld sample collection unit 506 to send a wireless signal to the base station 504 indicating that the handheld sample collection unit 506 has been activated, and the controller may then, in response thereto, initiate the preparation of such reagents.

In some implementations, the analysis unit controller may be configured to perform a pre-wetting operation on the BCM 514 in the handheld sample collection unit 506 prior to removal of the handheld sample collection unit. In such implementations, the analysis unit may be caused to, for example, dispense a quantity of eluent into the BCM 514 that is sufficient to flood the catch media within the BCM 514 (beads, filters, meshes, etc.) with eluent. After the catch media has been immersed in eluent, the eluent may be removed and directed to the waste reservoir, if desired. Pre-wetting the BCM 514 may enhance the breath constituent collection efficiency of the BCM 514.

Removal of the handheld sample collection unit 506 from the base station 504 may also be detected by a sensor on the handheld sample collection unit 506. In some implementations, detection of the removal of the handheld sample collection unit 506 from the base station 504 may be communicated to both the base station 504 and the handheld sample collection unit 506. Thus, regardless of whether the sensor that detects the removal of the handheld sample collection unit 506 from the base station 504 resides in the handheld sample collection unit 506 or in the base station 504, controllers in both apparatuses may be notified of such an event. This allows both systems to initiate various operations or protocols to facilitate sample collection and/or analysis.

The handheld sample collection unit 506 may also include a sensor that can determine whether or not a BCM 514 is installed in the handheld sample collection unit 506. If no BCM 514 is installed, then a controller of the handheld sample collection unit 506 may cause the handheld sample collection unit 506 to generate an alarm or notification (or may send a signal to the base station 504 to have the base station 504 do the same) indicating that the BCM 514 should be installed. Additionally, in many implementations, the BCM 514 may include a machine-readable code, e.g., a bar code, a QR code, an RFID tag, or an NFC tag, that uniquely identifies the BCM 514, and the handheld sample collection unit 506 may be configured to read such a code, e.g., via a bar code scanner, QR scanner, RFID receiver, or NFC reader, and compare it against a database of codes previously read from other BCM's 514—if the BCM 514 that is installed in the handheld sample collection unit 506 is identified as a BCM 514 that has been previously used in sample collection and analysis, the handheld sample collection unit 506 may sound a warning. In some implementations, the handheld sample collection unit 506 may send a signal to the base station 504 in such cases, and the controller of the base station 504 may prevent the performance of any analysis of a sample until the BCM 514 that is installed in the handheld sample collection unit 506 is replaced with a new BCM 514 that has a serial number or code that is not listed as having been previously used. In some implementations, the preparation of limited shelf-life reagents may not be initiated by the base station 504's controller until after the handheld sample collection unit 506 has confirmed that a BCM 514 having a serial number that indicates that it has not previously been used during sample collection has been connected with the handheld sample collection unit 506.

Figure 8:
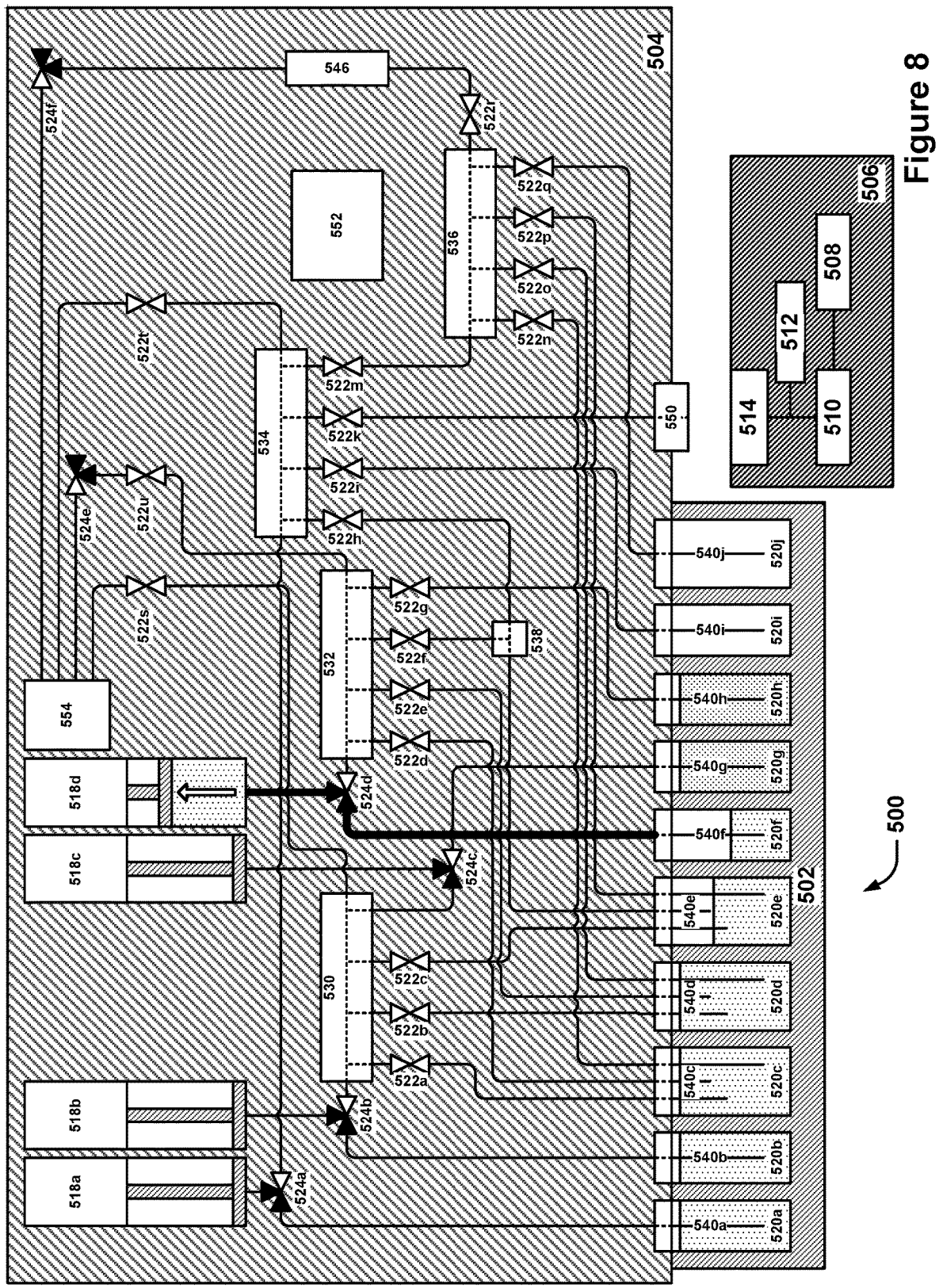
FIG. 8 depicts a schematic of the example target substance analysis system of FIG. 5 during an indicator solvent load operation.

FIG. 8 depicts a schematic of the example target substance analysis system of FIG. 5 during an indicator solvent load operation. Once the controller of the base station 504 has determined that indicator preparation is to begin, the controller may initiate various systems designed to produce a liquid-form indicator. For example, in FIG. 8, an indicator solvent pump 518d, which may be a syringe pump, for example, may be actuated to cause the indicator solvent in the indicator solvent reservoir 529f to be loaded into the indicator solvent pump 518d. A 3-way valve 524d may be set to a position that allows for fluidic communication between the indicator solvent pump 518d and the indicator solvent reservoir 520f prior to such pumping occurring.

Figure 9:
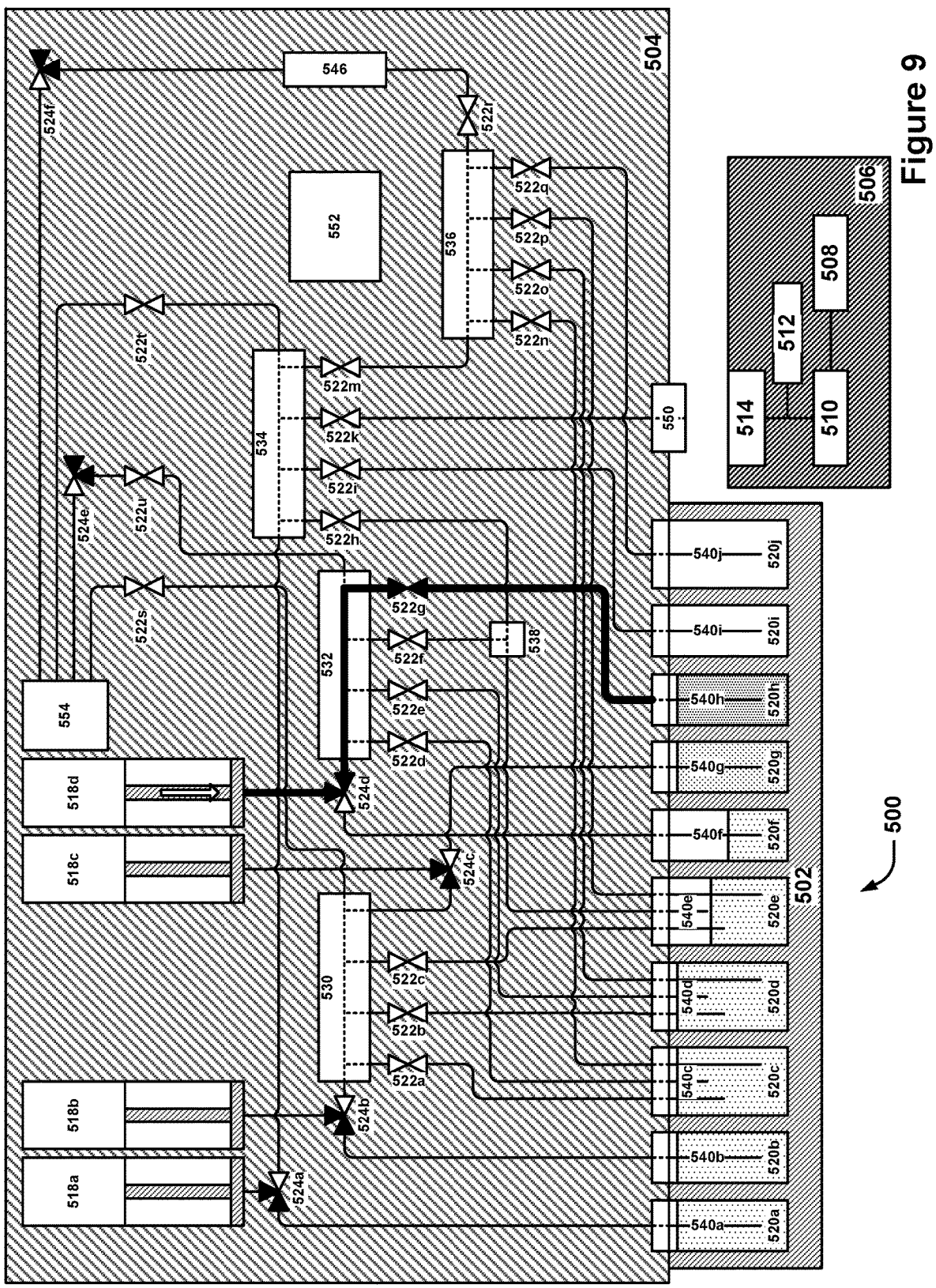
FIG. 9 depicts a schematic of the example target substance analysis system of FIG. 5 during dispensing of the indicator solvent into an indicator mixing chamber.

FIG. 9 depicts a schematic of the example target substance analysis system of FIG. 5 during dispensing of the indicator solvent into an indicator mixing chamber. In FIG. 9, the 3-way valve 524d has been set to a different position that prevents fluidic communication between the indicator solvent pump 518d and the indicator solvent reservoir 520f, but allows for fluidic communication between the indicator solvent pump 518d and the indicator mixing chamber 520h; valve 522g may also be opened to permit such fluidic communication. The indicator solvent pump 518d may then be actuated to dispense the indicator solvent into the indicator mixing chamber 520h, where the indicator solvent may mix with the powderized or granular indicator. In some implementations, the indicator may be a diazotized fluorophore, such as an amine-functionalized fluorophore or a primary amine functionalized fluorophore. Examples of potentially suitable fluorophores may include any one of: xanthenes, cyanines, naphthalenes, coumarins, oxadiazoles, anthracenes, pyrenes, oxazines, acridines, arylmethines, tetrapyrroles, green fluorescent proteins, red fluorescent proteins, yellow fluorescent proteins, cadmium selenide quantum dots, cadmium selenide/zinc sulfide alloy quantum dots, cadmium selenide sulfide quantum dots, cadmium selenide sulfide/zinc sulfide alloy quantum dots, cadmium telluride quantum dots, cadmium sulfide quantum dots, lead sulfide quantum dots, or indium phosphide/zinc sulfide alloy quantum dot, derivatives thereof, and mixtures thereof. In particular implementations, the fluorophore may be a xanthene, for example a rhodamine, for example rhodamine 123, for example rhodamine 123 diazotized at a primary amine group. The indicator solvent, for example, may be an acidic solution, e.g., diluted HCl, such as 100 µM HCl; combination of the indicator with the indicator solvent may produce, for example, an aqueous diazotized fluorophore solution that is relatively stable in liquid form (or at least stable for a long enough interval to allow analysis to reasonably be performed).

Figure 10:
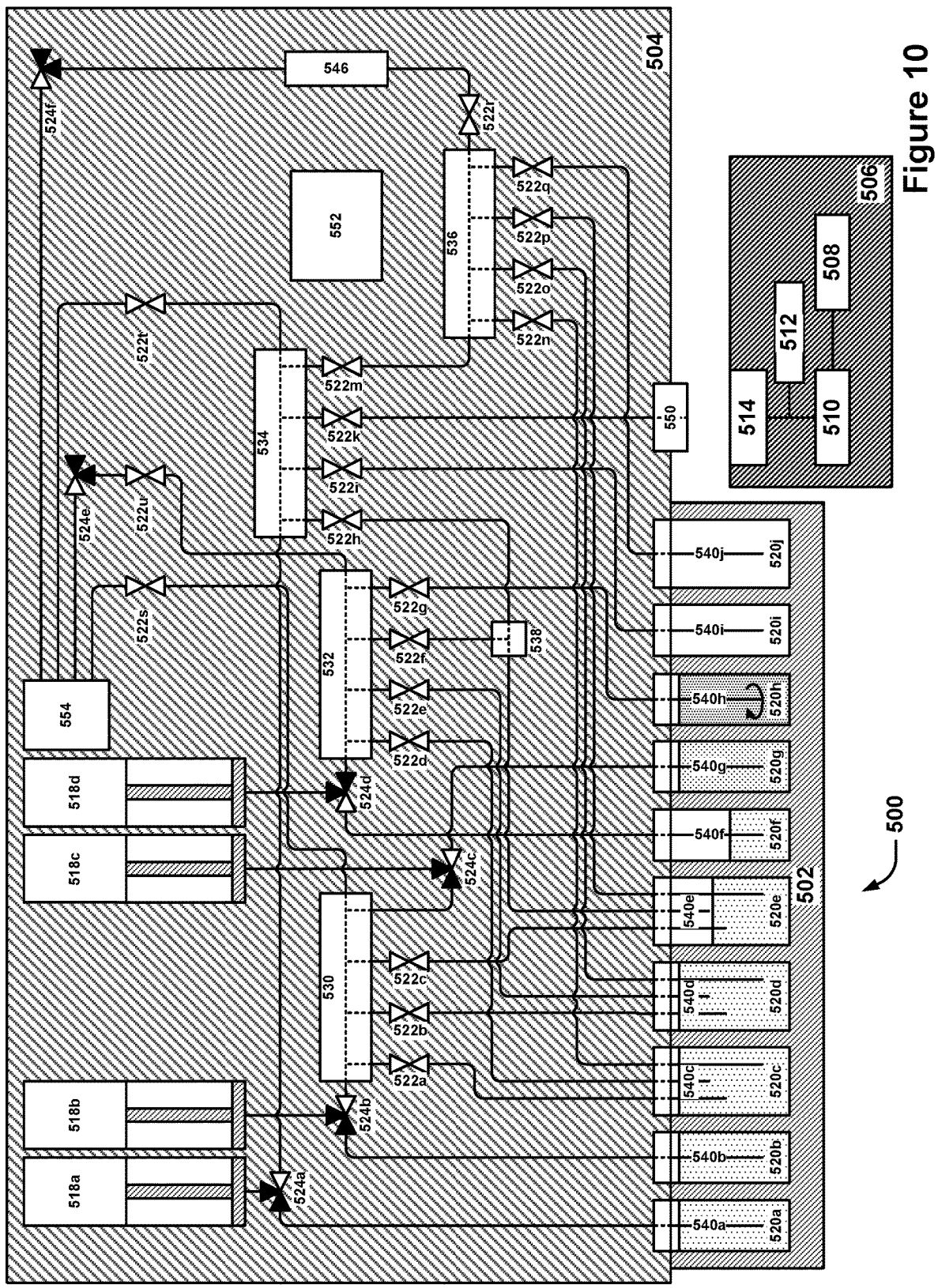
FIG. 10 depicts a schematic of the example target substance analysis system of FIG. 5 during mixing of the indicator and indicator solvent.

FIG. 10 depicts a schematic of the example target substance analysis system of FIG. 5 during mixing of the indicator and indicator solvent. In some implementations, after the indicator solvent and the indicator have been mixed together in the indicator mixing chamber 520h, a mixing mechanism may be activated to agitate the mixture and accelerate or otherwise enhance the mixing process. For example, in some implementations, the indicator mixing chamber 520h may include a magnetic stir bar that may be caused to rotate within the indicator mixing chamber 520h in order to agitate the contents. In other implementations, the mixing chamber 520h (or the entire reagent cartridge 502) may be vibrated or shaken, e.g., through the activation of a vibramotor or other oscillatory device, in order to agitate the contents of the indicator mixing chamber 520h.

Figure 11:
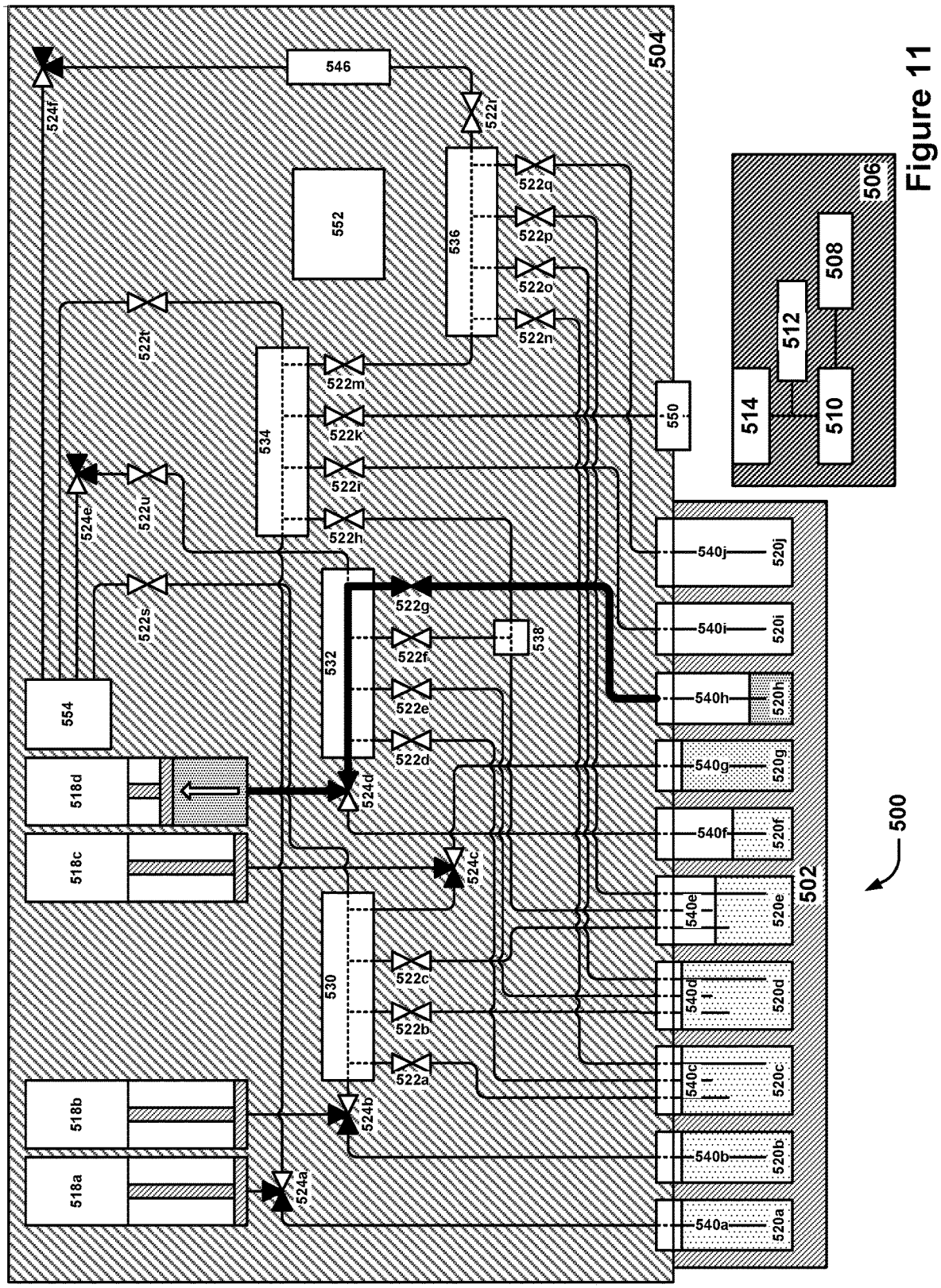
FIG. 11 depicts a schematic of the example target substance analysis system of FIG. 5 during a liquid indicator load operation.

FIG. 11 depicts a schematic of the example target substance analysis system of FIG. 5 during a liquid indicator load operation. Once the indicator solvent and indicator have been mixed in the indicator mixing chamber 520h for a period of time sufficient to produce adequate mixing, e.g., for 1 to 2 minutes, the liquid indicator that results may be withdrawn from the indicator mixing chamber 520h and, for example, stored in the indicator solvent pump 518d; valve 522g and 3-way valve 524d may be left in the states that they were in during the indicator solvent dispense operation discussed with respect to FIG. 9 to allow for such fluidic flow.

Figure 12:
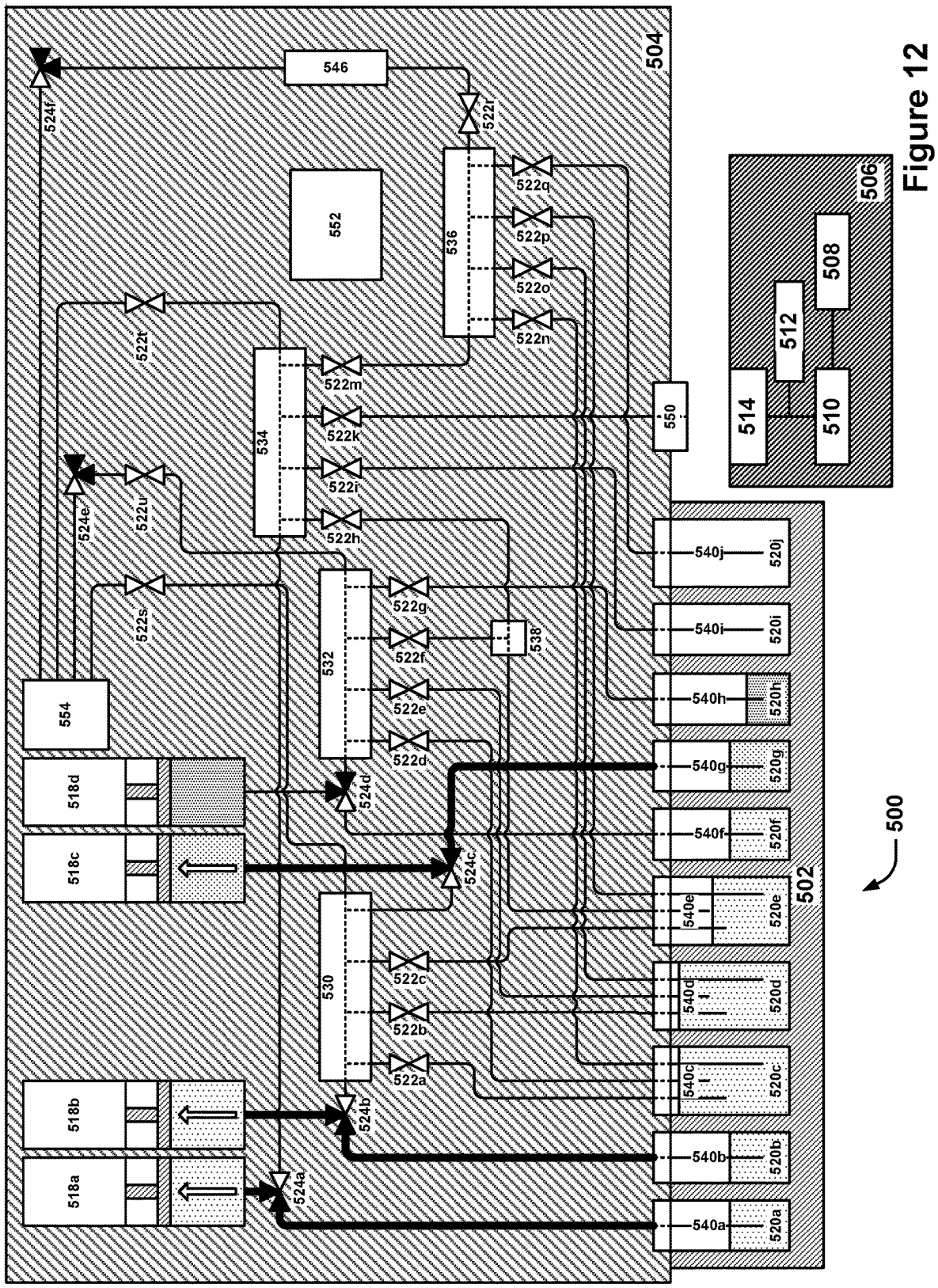
FIG. 12 depicts a schematic of the example target substance analysis system of FIG. 5 during eluent loading, organic solvent loading, and activator loading operations.

FIG. 12 depicts a schematic of the example target substance analysis system of FIG. 5 during eluent loading, organic solvent loading, and activator loading operations. After the indicator has been mixed, or, in some implementations, concurrently with or before such mixing occurs, the various other liquid reagents that may be used during the analysis technique may be prepared for dispensation. For example, the eluent stored in the eluent reservoir 520a may be withdrawn from the eluent reservoir 520a and loaded into an eluent pump 518a. Similarly, the organic solvent stored in the organic solvent reservoir 520b may be withdrawn from the organic solvent reservoir 520b and loaded into an organic solvent pump 518b, and the liquid activator stored in the activator reservoir 520g may be withdrawn from the activator reservoir 520g and loaded into an activator pump 518c. The 3-way valves 524a, 524b, and 524c, respectively, may each be positioned to allow for such fluidic communication.

The indicator mixing and reagent loading operations may be performed while the handheld sample collection unit 506 is being used to collect a sample from a subject. Alternatively, some implementations may perform such loading operations at different times or may even, if configured appropriately, simply pump chemicals directly to their destinations from their reservoirs rather than loading them into a pump as an intermediate step.

Figure 13:
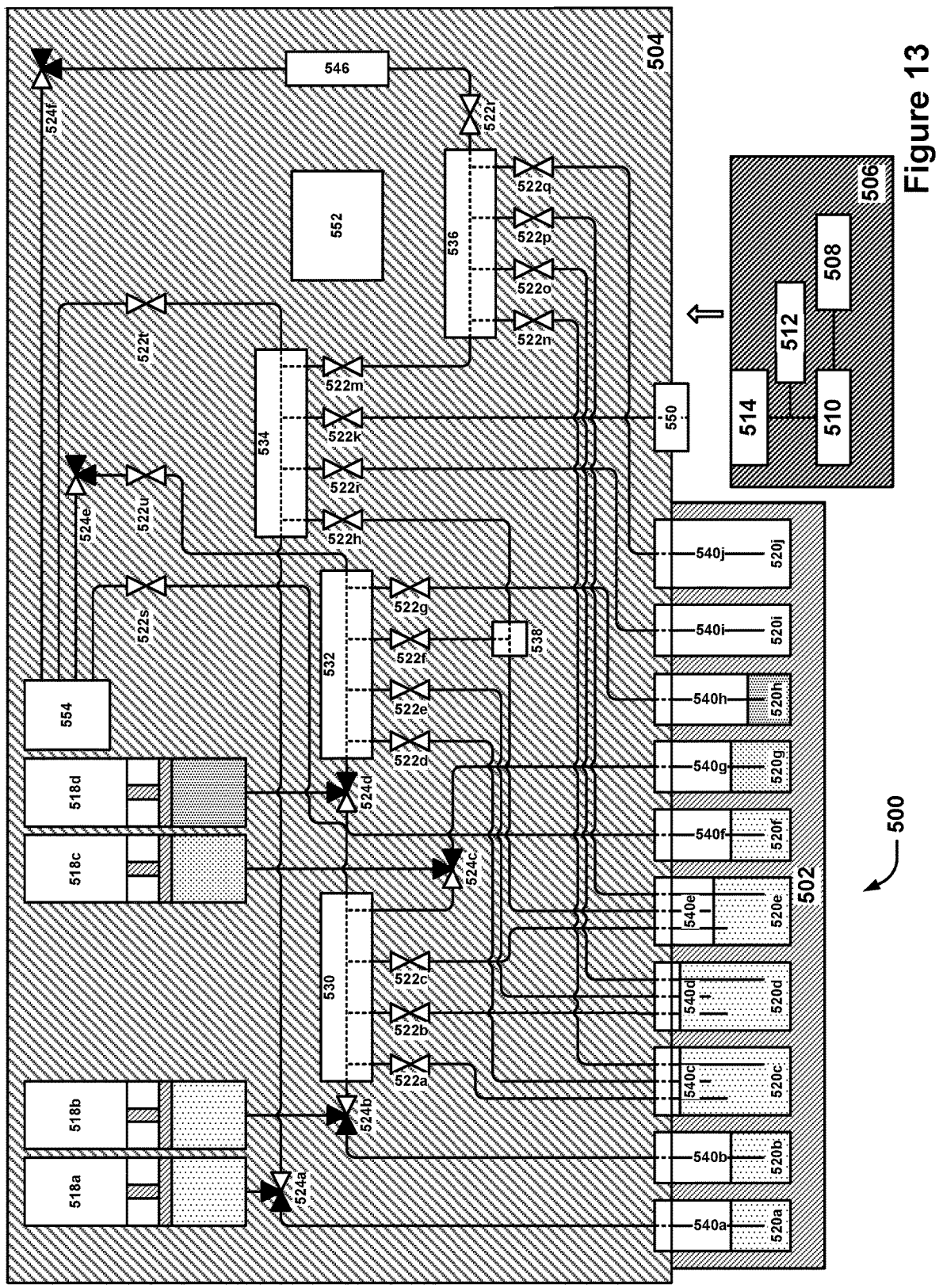
FIG. 13 depicts a schematic of the example target substance analysis system of FIG. 5 during docking of the handheld sample collection unit.

FIG. 13 depicts a schematic of the example target substance analysis system of FIG. 5 during docking of the handheld sample collection unit 506. Once an adequate breath constituent sample has been collected with the handheld sample collection unit 506, the handheld sample collection unit 506 may be docked with the base station 504 such that the BCM 514 is interfaced with the elution port 550.

Figure 14:
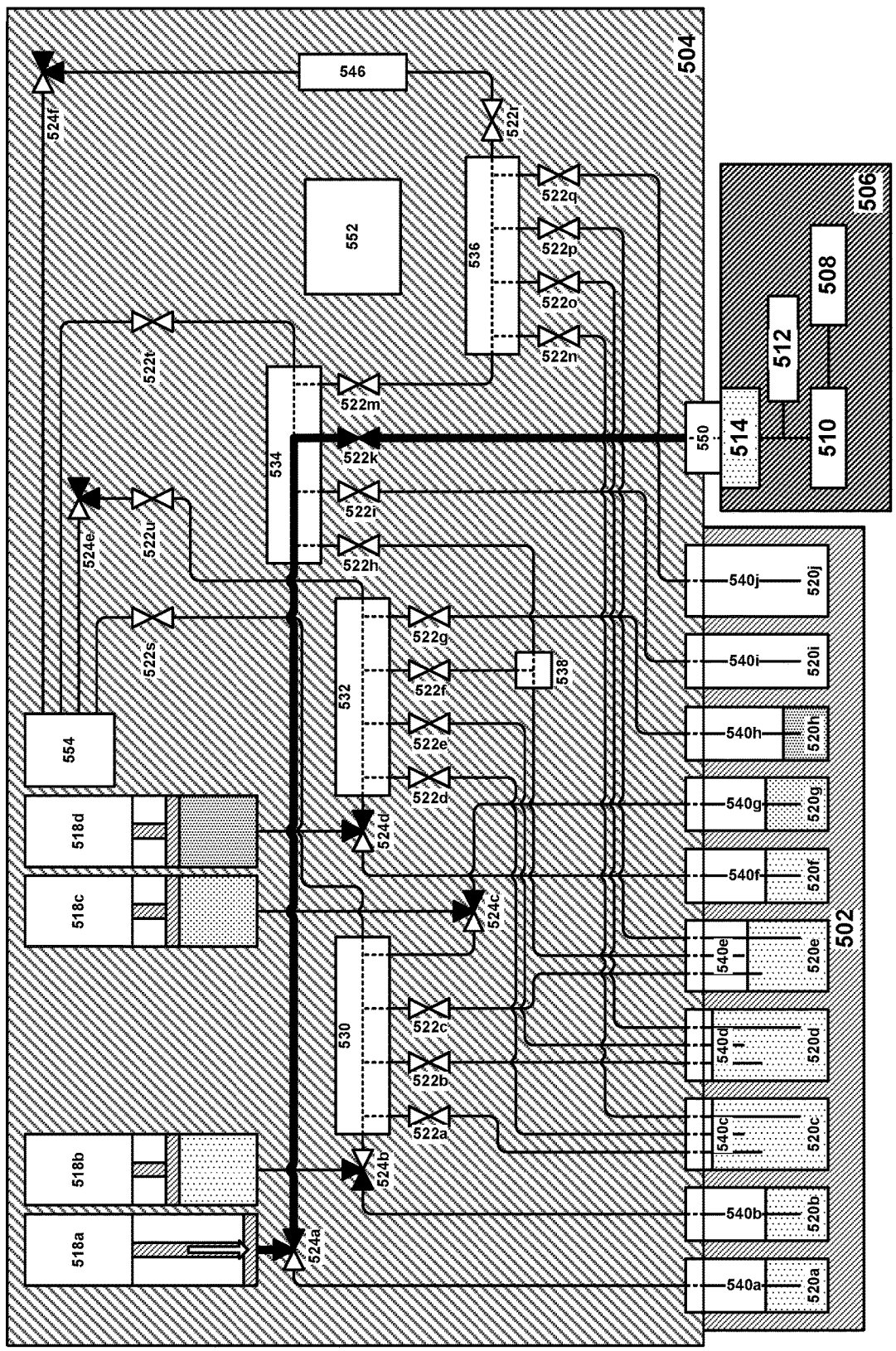
FIG. 14 depicts a schematic of the example target substance analysis system of FIG. 5 during delivery of the eluent to a breath capture module docked with the target substance analysis system.

FIG. 14 depicts a schematic of the example target substance analysis system of FIG. 5 during delivery of the eluent to a breath capture module docked with the target substance analysis system. After the handheld sample collection unit 506 is docked with the base station 504, the eluent pump 518a may be activated by the controller to cause the eluent (or a portion thereof) to be dispensed to the elution port 550 and then into the BCM 514. The 3-way valve 524a and the valve 522k may be positioned or set to permit such fluidic flow. In some implementations, the eluent may be a polar organic solvent such as ethanol (EtOH) or other suitable polar organic solvent that is miscible with water, e.g., alcohols.

Once the eluent has been dispensed to the BCM 514, the eluent may be allowed to soak the interior of the BCM 514 for a predetermined period of time, e.g., 30 seconds, a minute, or some other sufficiently long period of time to allow for breath constituents that have been adsorbed onto the interior surfaces of the BCM 514 to be eluted into the eluent.

Figure 15:
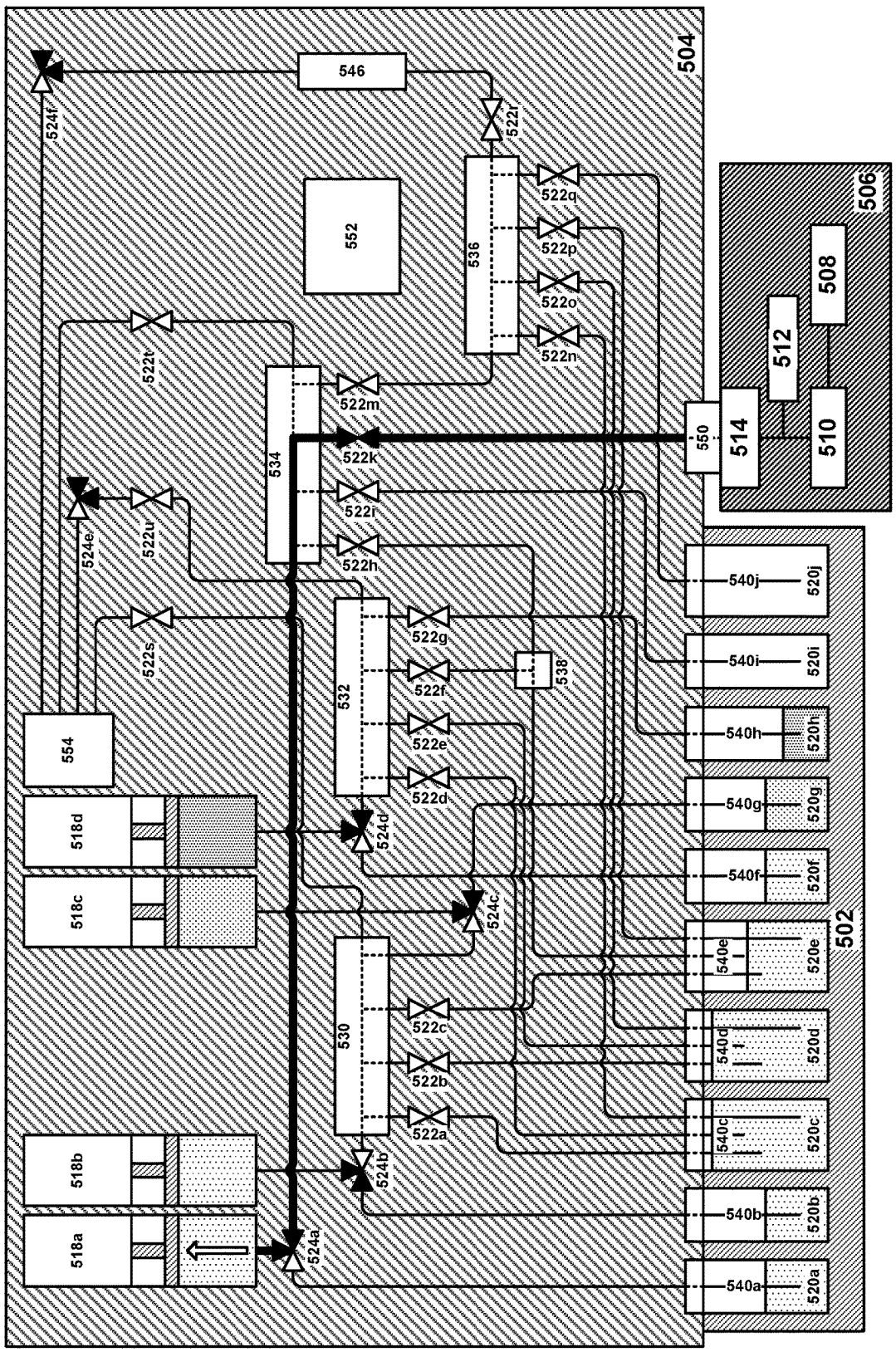
FIG. 15 depicts a schematic of the example target substance analysis system of FIG. 5 during loading of a mixture of the eluent and eluted breath constituents from the breath capture module.

FIG. 15 depicts a schematic of the example target substance analysis system of FIG. 5 during loading of a mixture of the eluent and eluted breath constituents from the breath capture module. Once the eluent has been resident in the BCM 514 for a suitably long enough period of time, the eluent pump 518a may be activated again to withdraw the eluent and the eluted breath constituents from the BCM 514 and into the eluent pump 518a. The 3-way valve 524a and the valve 522k may be positioned or set to permit such fluidic flow, similar to their positioning in FIG. 14.

Figure 16:
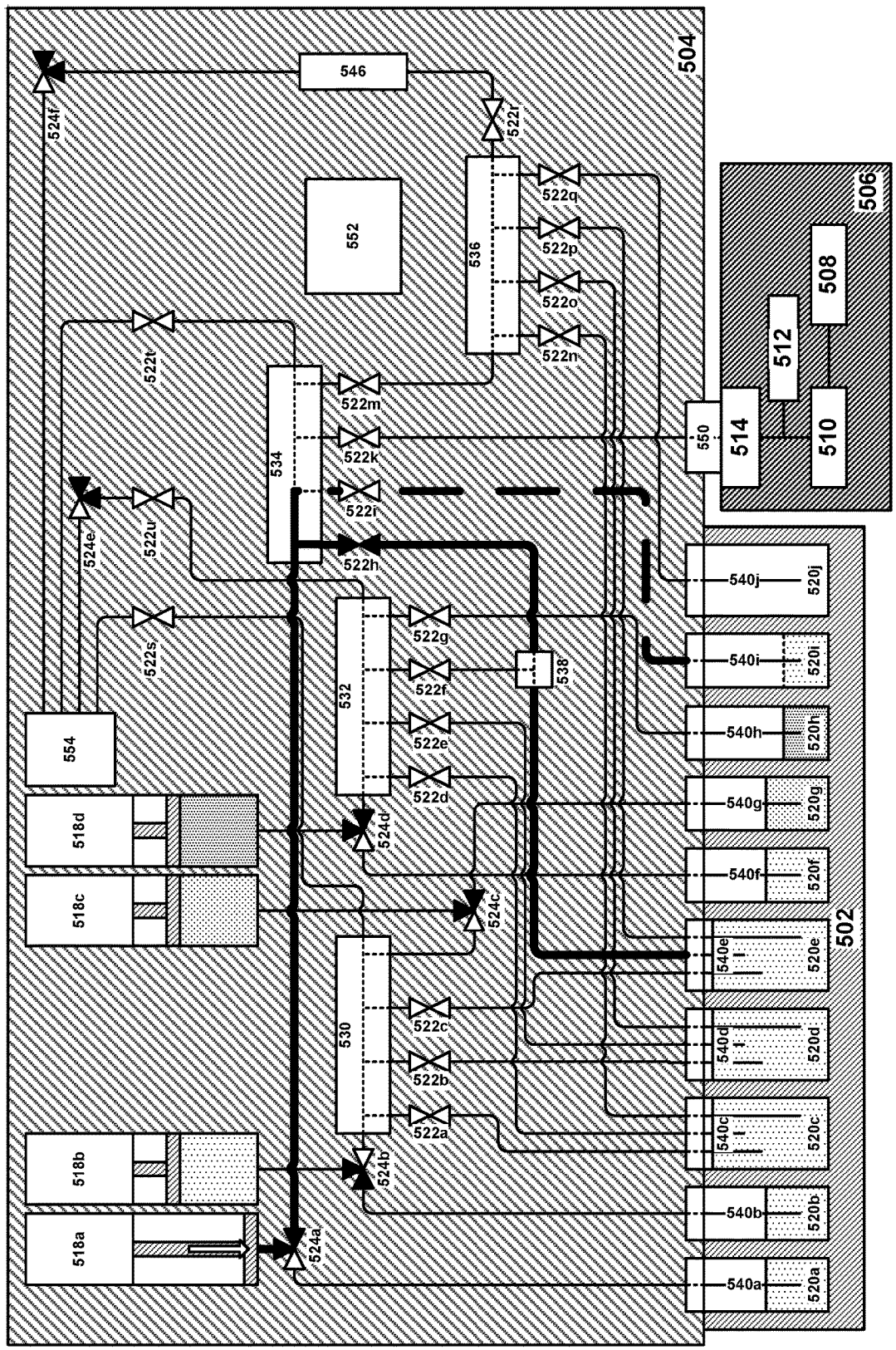
FIG. 16 depicts a schematic of the example target substance analysis system of FIG. 5 during dispensing of the eluent and eluted breath constituents into a sample mixing chamber.

FIG. 16 depicts a schematic of the example target substance analysis system of FIG. 5 during dispensing of the eluent and eluted breath constituents into a sample mixing chamber. Once the eluted breath constituents and eluent have been loaded into the eluent pump 518a, the eluted breath constituents and eluent may be dispensed into the sample mixing chamber 520e by activating the eluent pump 518a. Valve 522k may be switched off and valve 522h may be switched on to facilitate such fluidic transfer. The amount of eluent and eluted breath constituents that may be transferred to the sample mixing chamber 520e may be metered by the eluent pump 518a to ensure that only a predetermined amount of eluent and breath constituent sample are transferred to the sample mixing chamber 520e. The amount of eluent and breath constituent sample that are transferred may be selected such that the total amount of fluid that is in each of the sample mixing chamber 520e, the negative control mixing chamber 520c, and the positive control mixing chamber 520d after sample delivery is complete is the same.

For example, the positive control mixing chamber 520d may include a predetermined quantity of THC, e.g., up to 5 ng of THC or a concentration of up to 20 ng/mL, mixed with a basic buffer solution, e.g., a mixture of $NaHCO_3$ and $Na_2CO_3$, e.g., 60% mol $NaHCO_3$ and 40% mol $Na_2CO_3$, to reach a first predetermined volume of buffer and THC. The basic buffer solution may counteract the acidity of the liquid indicator, for example, and leave the mixed solution of buffer, THC (if present), eluent (if present), and indicator to a basic pH, e.g., between 9 and 11, or between about 9.5 and 10. Fluorescent-labeled THC adducts are stable when in a basic solution, but may rapidly degrade when exposed to an acidic environment. Conversely, the aqueous diazotized fluorophore solution may be stable in an acidic solution, e.g., such as when dissolved in hydrochloric acid. In order to increase the longevity of the THC adducts that may result from mixing of the liquid-phase indicator with the eluted breath constituent sample and/or the calibration samples or controls, the eluted breath constituent sample and the calibration or control samples may be combined with the basic buffer to prevent or mitigate the degradation of any THC adducts that are formed when the eluted breath constituent sample and/or the calibration or control samples are combined with the liquid-phase indicator, e.g., by raising the pH of the eluted breath constituent sample and/or the calibration or control samples sufficiently high enough that the subsequent addition of an acidic indicator solution to the eluted breath constituent sample and/or the calibration or control samples does not cause the THC adduct to degrade significantly (or at all). Other basic buffers may be used as well in place of $NaHCO_3$ and $Na_2CO_3$. The buffer may be added to the eluted sample after elution occurs to avoid diluting the eluent and interfering with the effectiveness of elution of the breath constituent sample. An amount of eluent may be added to this mixture in an amount similar to the amount of eluent that may be used to obtain the sample from the BCM 514. The eluent may be pre-added to the positive control mixing chamber 520d when the reagent cartridge 502 is manufactured, or, in some implementations, may be added by transferring eluent from the eluent reservoir 520a during an analysis. Thus, the positive control may have an overall fluid volume that is predominantly divided between the basic buffer and the eluent, with some small amount of THC included as well. The negative control may be formulated in the same manner, but with a lower amount (or no amount) of THC included. The positive control and negative control may also be referred to as calibration samples, e.g., a first calibration sample and a second calibration sample.

The positive control or calibration sample may, in some implementations, have an amount of THC thought to be slightly higher, e.g., 10% higher, than the amount of THC that could reasonably be expected to be in an eluted breath constituent sample of a person who has recently used marijuana so that the fluorescent response of the breath constituent sample during the analysis is bracketed by the positive and negative calibration samples or controls. It is to be understood that in some implementations, a non-zero negative control (not truly negative) or a positive control that is lower than the expected maximum quantity of THC that could reasonably be expected to be in the eluted breath constituent sample may be used. For example, if the legal framework surrounding marijuana use evolves to allow some amount of THC to be present in a person's breath before the person is considered to be "impaired," then the negative control may be pegged to this lower limit instead of to zero.

The sample mixing chamber 520e, however, may initially be pre-loaded with approximately the same amount of basic buffer as is used in the positive control mixing chamber 520d and the negative control mixing chamber 520c, but may not initially include any of the eluent, which may instead be added later as part of the sample delivery.

For example, in some implementations, the positive and negative control mixing chambers 520d and 520c, respectively, may each include approximately 500 µL of basic buffer and 250 µL of eluent, e.g., ethanol (EtOH), for an overall fluid volume of approximately 750 µL (the positive control mixing chamber 520d, at least, may also have some small portion of that 750 µL occupied by THC). Correspondingly, the sample mixing chamber 520e may only be stocked with approximately 500 µL of basic buffer, with the remaining 250 µL of fluid volume to be supplied later as part of the delivery of eluent and breath constituents. Thus, all three of the mixing chambers 520c through 520e may include the same overall volume of fluids, and in approximately the same ratios, prior to analysis, thereby reducing the variance between the sample and the controls, e.g., the main differences between the controls and the sample will be in the amount of sample that is present, as opposed to the amounts of eluent and basic buffer that are present. This may reduce error in the analysis.

If there is left over eluent and breath constituent sample after filling the sample mixing chamber 520e to the desired volume, the extra eluent and breath constituent sample may be shunted (indicated by the heavy dashed flow path) to a sample reservoir 520i by turning off valve 522h and activating valve 522i. In other implementations, the leftover eluent and breath constituent sample may instead be directed to the waste reservoir 520j, retained in the eluent pump 518a, or otherwise housed or disposed of. However, retaining the leftover eluent and breath constituent sample in the sample reservoir 520i may be desirable from an evidentiary perspective, in that the leftover eluent and breath constituent sample may be preserved for later, confirmatory laboratory testing.

Figure 17:
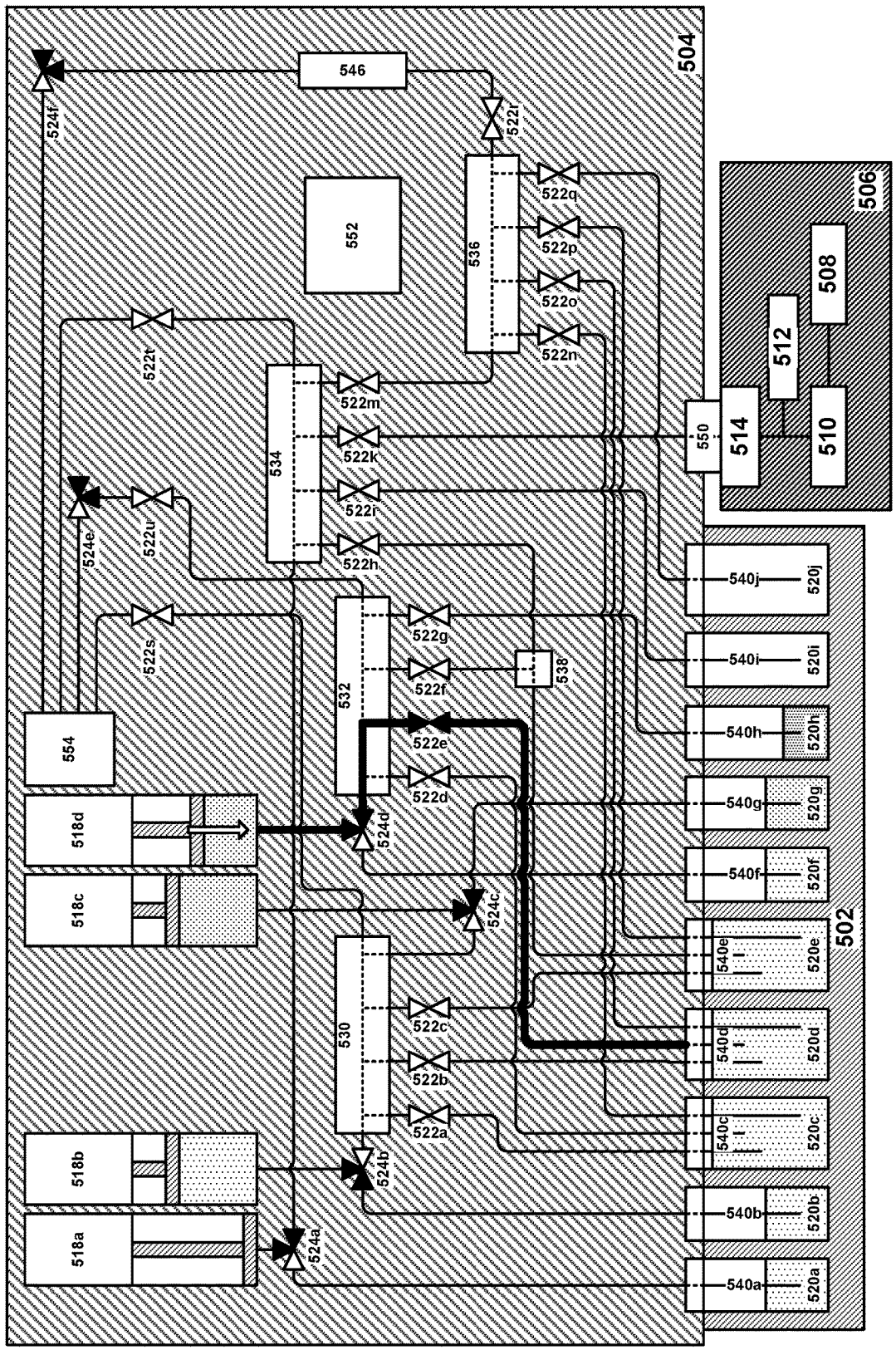
FIG. 17 depicts a schematic of the example target substance analysis system of FIG. 5 during dispensing of a portion of the liquid indicator into a positive control mixing chamber.

FIG. 17 depicts a schematic of the example target substance analysis system of FIG. 5 during dispensing of a portion of the liquid indicator into the positive control mixing chamber. For example, the indicator solvent pump 518d may be controlled to dispense a portion of the indicator fluid through the 3-way valve 524d and the valve 522e and into the positive control mixing chamber 520d.

Figure 18:
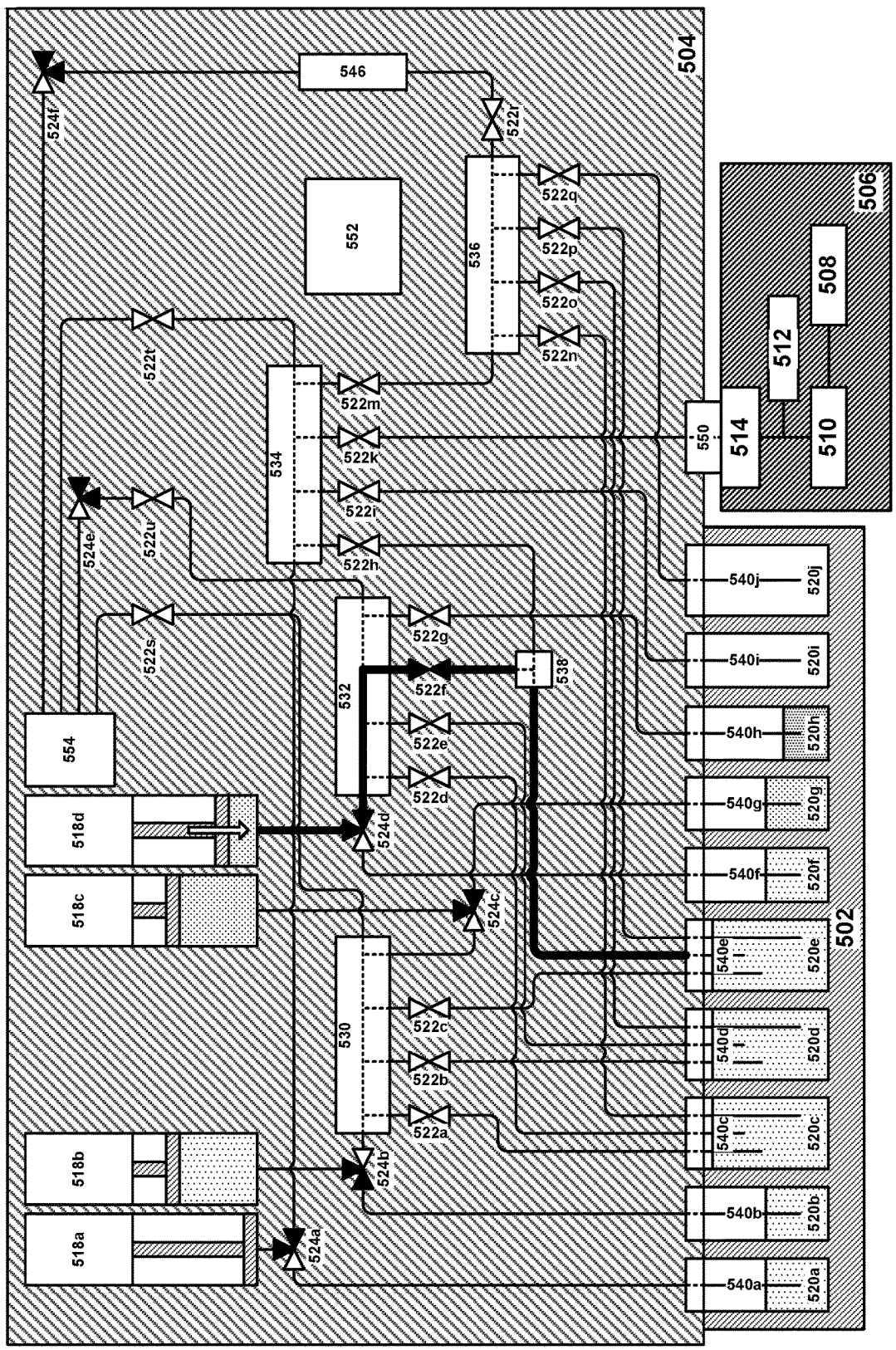
FIG. 18 depicts a schematic of the example target substance analysis system of FIG. 5 during dispensing of another portion of the liquid indicator into the sample mixing chamber.

FIG. 18 depicts a schematic of the example target substance analysis system of FIG. 5 during dispensing of another portion of the liquid indicator into the sample mixing chamber. For example, the indicator solvent pump 518d may be controlled to dispense a further portion of the indicator fluid through the 3-way valve 524d and the valve 522f (which may be opened; valve 522e may correspondingly be closed) and into the sample mixing chamber 520e.

Figure 19:
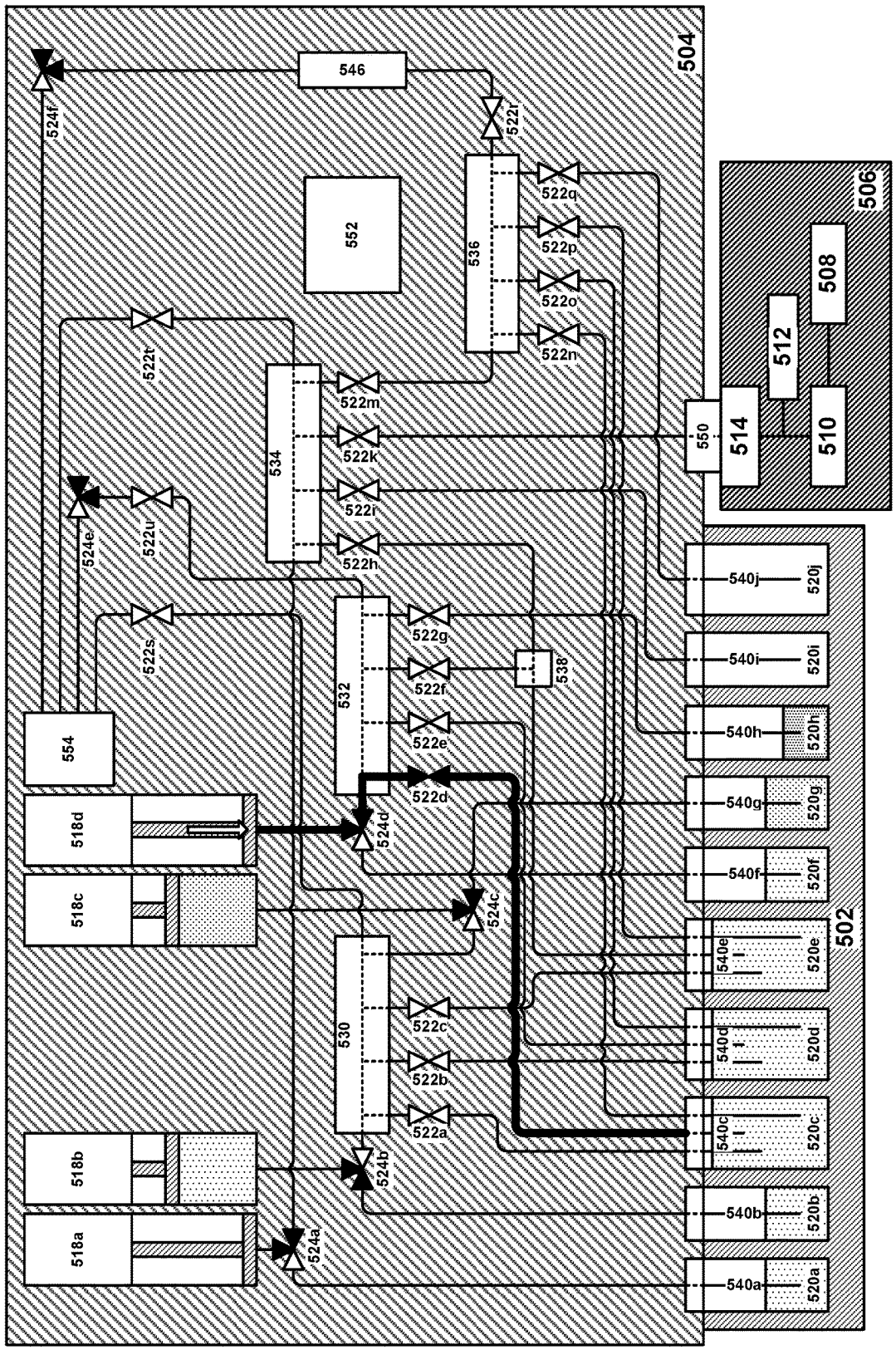
FIG. 19 depicts a schematic of the example target substance analysis system of FIG. 5 during dispensing of a portion of the liquid indicator into a negative control mixing chamber.

FIG. 19 depicts a schematic of the example target substance analysis system of FIG. 5 during dispensing of a portion of the liquid indicator into the negative control mixing chamber. For example, the indicator solvent pump 518*d* may be further controlled to dispense a another portion of the indicator fluid through the 3-way valve 524*d* and the valve 522*d* (which may be opened; valve 522*f* may correspondingly be closed) and into the negative control mixing chamber 520*c*. The particular order in which the indicator liquid is dispensed into the various mixing chambers may be different from the order discussed above. For example, the indicator liquid may first be added to the mixing chambers in the order that the contents of the mixing chambers will be analyzed.

Figure 20:
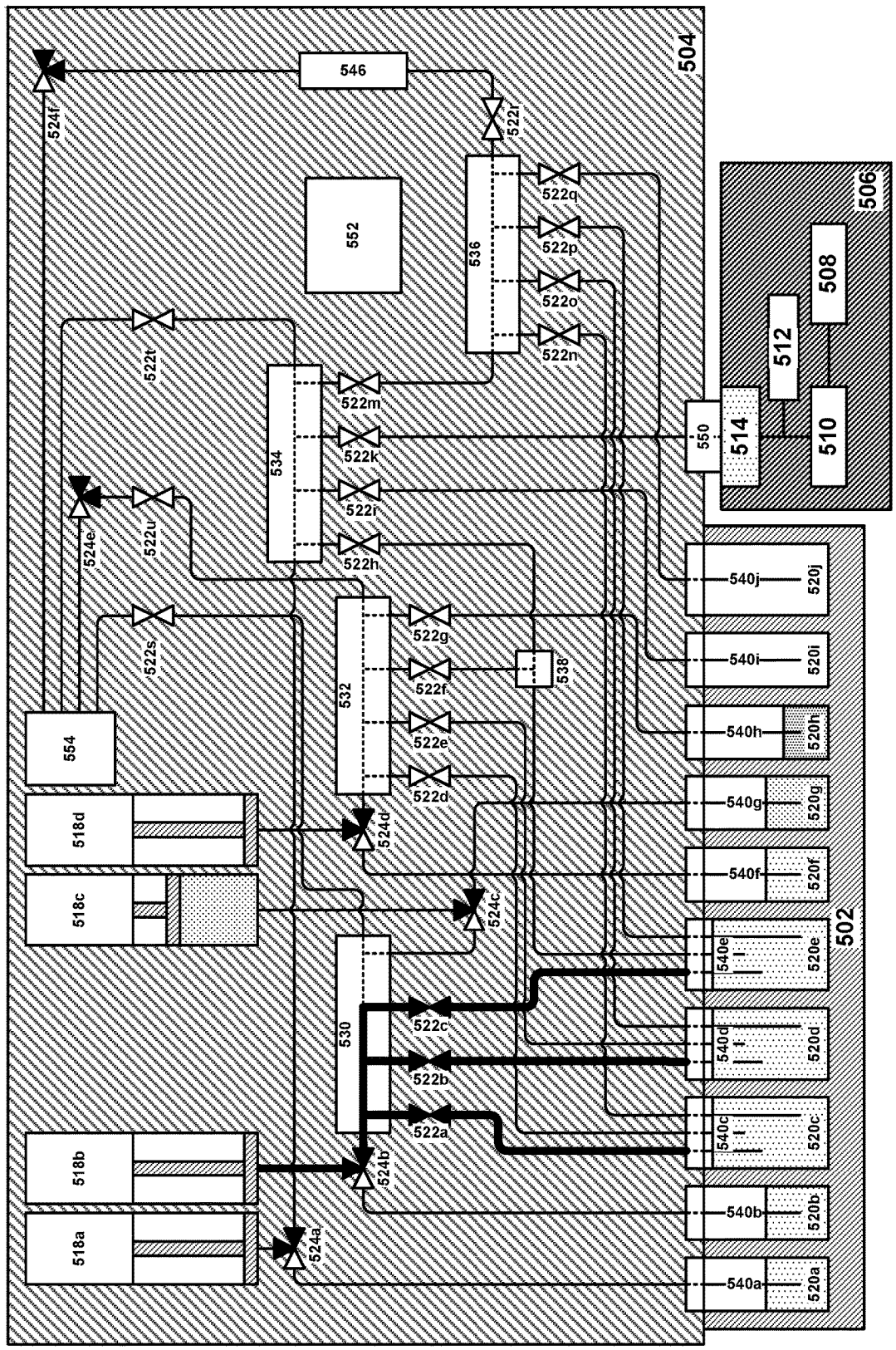
FIG. 20 depicts a schematic of the example target substance analysis system of FIG. 5 during dispensation of an organic solvent into the negative control mixing chamber, the sample mixing chamber, and the positive control mixing chamber.
Figure 21:
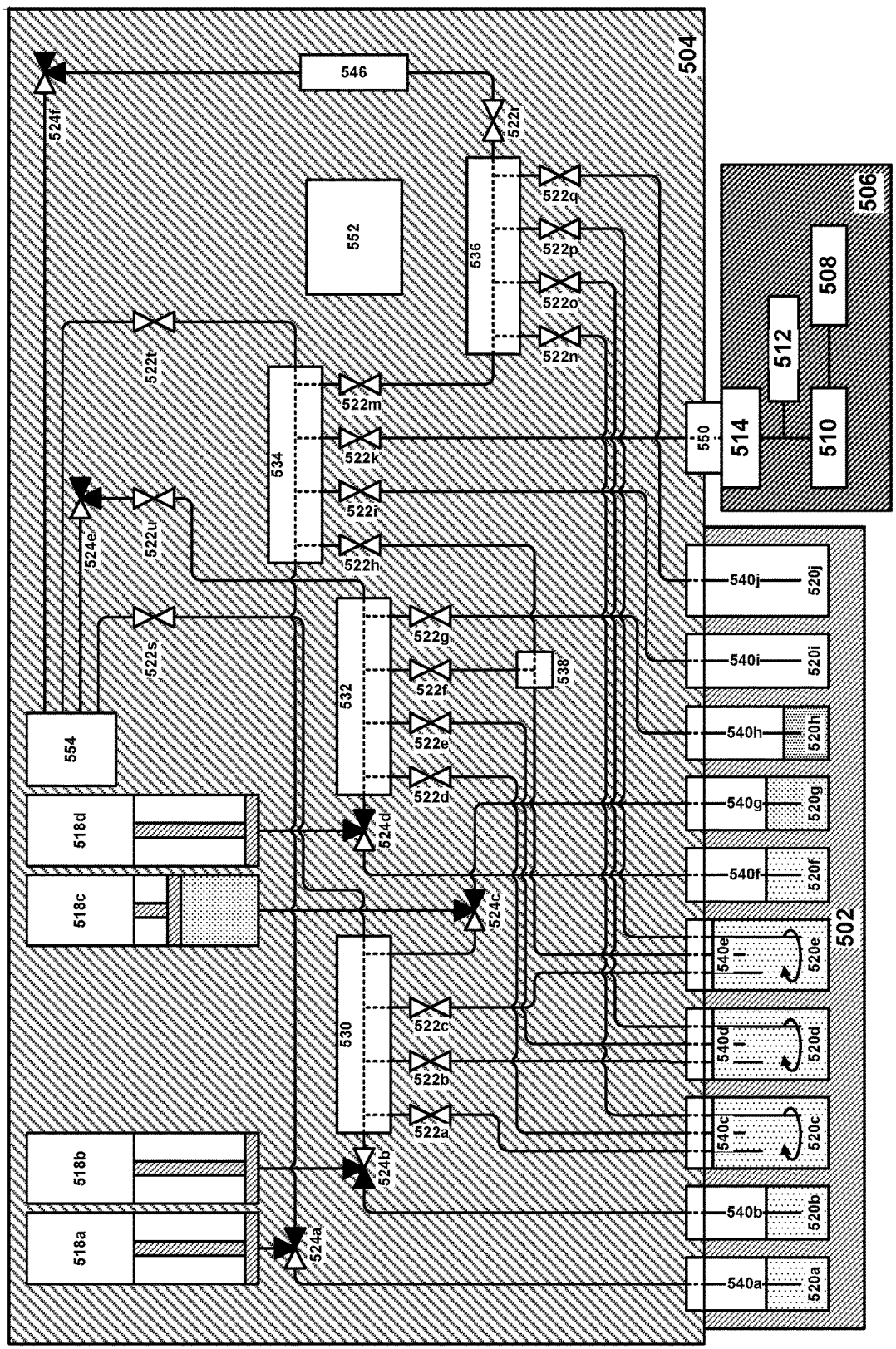
FIG. 21 depicts a schematic of the example target substance analysis system of FIG. 5 during mixing of the contents of the negative control mixing chamber, the sample mixing chamber, and the positive control mixing chamber.

FIG. 20 depicts a schematic of the example target substance analysis system of FIG. 5 during dispensation of an organic solvent into the negative control mixing chamber, the sample mixing chamber, and the positive control mixing chamber. Once the indicator has been dispensed into the sample mixing chamber 520*e*, the negative control mixing chamber 520*c*, and the positive control mixing chamber 520*d*, the organic solvent may be added to all three of these mixing chambers. The organic solvent may, in various implementations, be a non-polar organic solvent that is immiscible in water, such as a mixture of heptane and methyl tertiary butyl ether (MTBE), e.g., a 75:25 volumetric ratio of heptane to MTBE (such as 15-50% by volume MTBE with the remainder heptane), or other similar organic solvents, e.g., alkanes, ethers, etc. The organic solvent pump 518*b* may be actuated to deliver portions, preferably equal-volume portions (such as, for example, 750 μL per mixing chamber), of the organic solvent from the organic solvent pump 518*b* to each of these three mixing chambers. In FIG. 20, the organic solvent is delivered to the sample mixing chamber 520*e*, the negative control mixing chamber 520*c*, and the positive control mixing chamber 520*d* in parallel, e.g., simultaneously. However, in actual practice, such organic solvent delivery may be done serially so as to more accurately control the amount of organic solvent that is delivered to each mixing chamber to ensure that equal amounts of organic solvent are delivered to each mixing chamber. FIG. 21 depicts a schematic of the example target substance analysis system of FIG. 5 during mixing of the contents of the negative control mixing chamber, the sample mixing chamber, and the positive control mixing chamber. After the organic solvent has been added to the sample mixing chamber 520*e*, the negative control mixing chamber 520*c*, and the positive control mixing chamber 520*d*, the contents of these three mixing chambers may be agitated to cause the organic solvent, indicator, basic buffer, eluent, and any breath constituents in the mixing chambers to more thoroughly mix. Such mixing or agitation may be accomplished using mixing mechanisms similar to those discussed earlier with respect to the mixing that may be performed in the chamber, e.g., magnetic stir bars located in the mixing chambers and mechanism that induces a rotating magnetic field that causes the stir bars to rotate. Such mixing may be performed for a sufficiently long enough period of time, e.g., 30 seconds, a minute, or several minutes, for the contents to be thoroughly mixed and for the adduct that results from the combination of the indicator with any THC that is present to be mixed with the non-polar organic solvent. After the contents of the mixing chambers have been mixed, the mixing chambers may be left to rest, e.g., for 30 seconds, a minute, or several minutes, to allow the polar and non-polar mixtures contained within each mixing chamber to separate out into separate polar and non-polar layers, with the adduct being contained within the non-polar layer.

Figure 22:
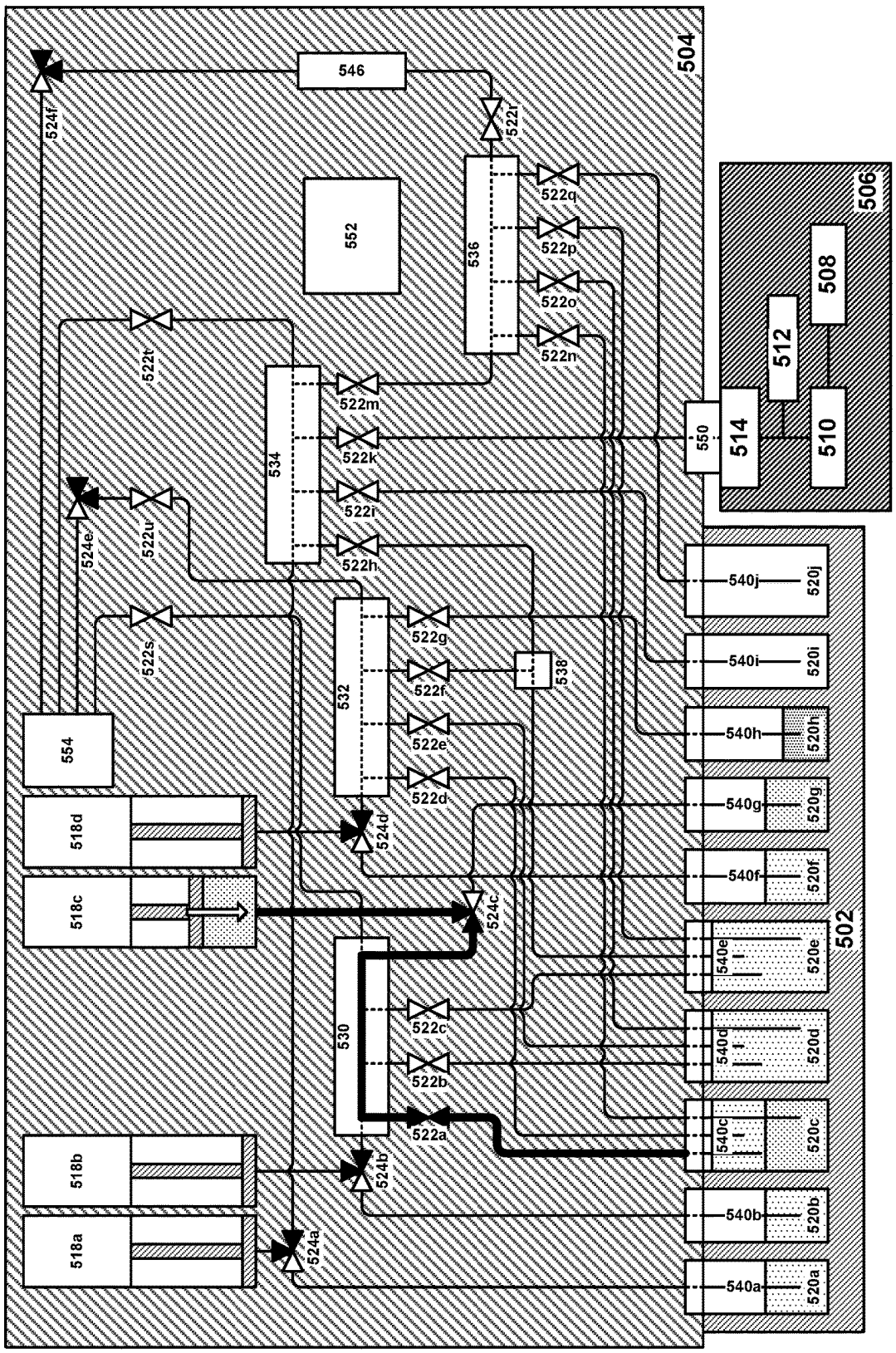
FIG. 22 depicts a schematic of the example target substance analysis system of FIG. 5 during dispensing of an activator to the negative control mixing chamber.

In some implementations, an activator may be applied to the separated-out non-polar layer. FIG. 22 depicts a schematic of the example target substance analysis system of FIG. 5 during dispensing of an activator to the negative control mixing chamber. In FIG. 22, the activator pump 518*c* has been actuated to dispense a predetermined amount of activator from the activator pump 518*c* into the negative control mixing chamber 520*c*; fluidic interfaces 540*c*, 540*d*, and 540*e* may each have, for example, a tube that extends into the corresponding mixing chamber to a depth that places the end of the tube at some location above the polar layer after separation, e.g., at an elevation that is between 20% and 50% of the thickness of the non-polar layer above the polar layer/non-polar layer interface (it should be noted that the relative lengths of the tubes/probes/needles of each fluidic interface shown in FIGS. 5 through 30 are not drawn to scale and should not be viewed as indicative of their relative lengths or their lengths relative to other elements depicted in the Figures). The activator may be dispensed directly into each of the non-polar layers using such tubes. The activator may react with the adduct to cause the adduct's fluorescent characteristics to be enhanced, which may allow for easier measurement of the amount of fluorescence from the adduct. For example, one activator that proved to be particularly effective in tests is poly(2-ethyl hexyl acrylate) (PEHA), although other implementations may use any one or more of the activators discussed elsewhere in this disclosure. The activator may also be added to the non-polar adduct solution after it is withdrawn from the mixing chamber and isolated from the polar layer. In the depicted implementation, the amount of non-polar adduct solution that may be withdrawn from each mixing chamber may vary somewhat since the transfer of the non-polar adduct mixture from the mixing chambers to the optical measurement chamber is performed by pressurizing the mixing chamber with air (see later discussion) and forcing the mixture into the tube/siphon that leads to the optical measurement chamber. Since there may be some air leakage during this operation, the pressure conditions and volumetric displacement for each mixing chamber may differ, and the amount of fluid that is transferred may thus vary to a greater extent than if a positive displacement pump, such as a syringe pump, were used to accomplish the same transfer. As a result, it may be beneficial to add the activator to the non-polar layer prior to such extraction so that the ratio of activator volume to non-polar layer volume is the same for each mixing chamber so that the activator dilution factor is constant. If a more precise fluid transfer system is used, i.e., one that results in metered quantities of fluid being transferred from each mixing chamber to the optical measurement chamber, then the activator may be added after withdrawal of the fluid from each mixing chamber without such varying dilution factors being a concern.

At this stage, the positive and negative controls, as well as the sample, are prepared for analysis. While the analysis of the contents of each mixing chamber may be done in any order, it may be beneficial, in some implementations, to first analyze the contents of the negative control mixing chamber 520*c*, followed by the sample mixing chamber 520*e* contents, followed by the positive control mixing chamber 520*d* contents so that there is a reduced chance that the negative control will be contaminated by the THC in the positive control or any THC that may be in the sample, and so that there is also a reduced chance that the sample may be contaminated by THC from the positive control. In the implementation depicted in FIG. 17, the negative control is prepared first for analysis.

Figure 23:
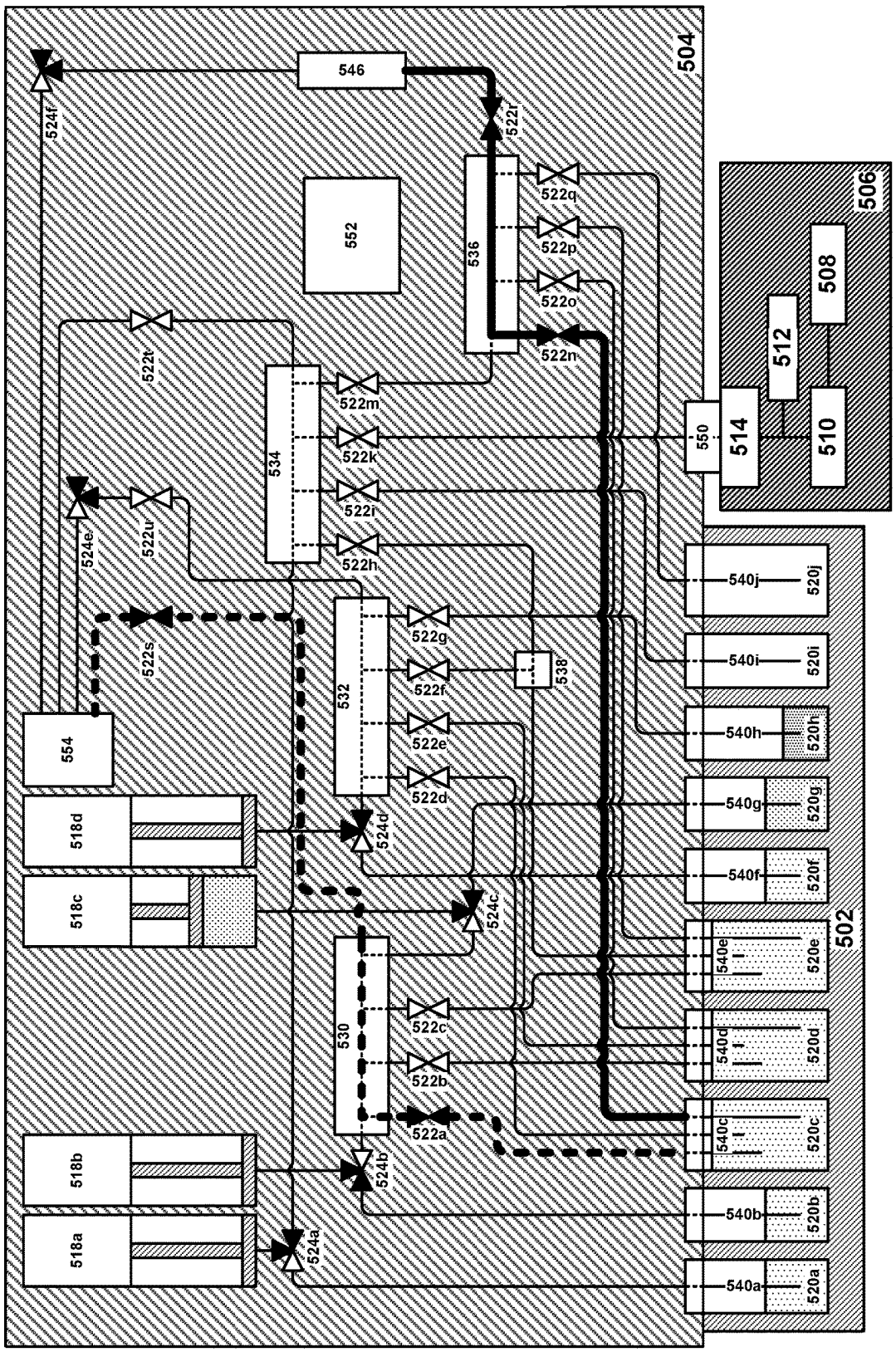
FIG. 23 depicts a schematic of the example target substance analysis system of FIG. 5 during dispensation of the negative control to an optical measurement chamber.

FIG. 23 depicts a schematic of the example target substance analysis system of FIG. 5 during delivery of the negative control to an optical measurement chamber. In FIG. 23, the controller has activated the air pump 554 and opened valves 522s, 522a, 522n, and 522r to cause the air pump 554 to pressurize the negative control mixing chamber and cause the non-polar layer containing the adduct to be pumped through the negative control fluidic interface 540c and into the optical measurement chamber 546. For example, using the air pump 554 to drive the fluidic movement of the mixing chamber contents to the optical measurement chamber 546 avoids drawing the mixing chamber contents into one of the pumps, which might cause contamination issues for subsequent such transfers of mixing chamber contents due to residue that might be left in the pump.

Figure 24:
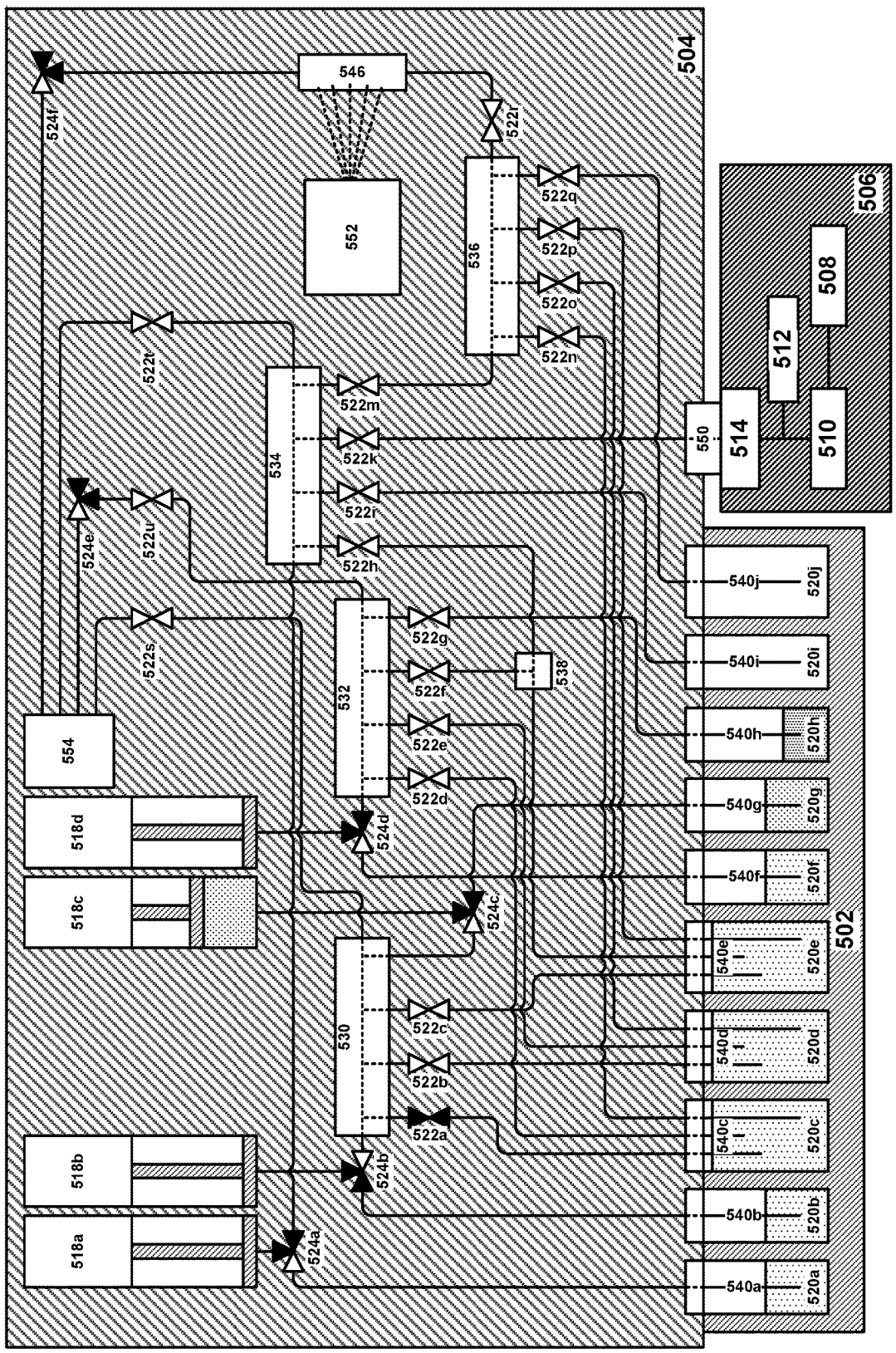
FIG. 24 depicts a schematic of the example target substance analysis system of FIG. 5 during an optical measurement of the contents of the optical measurement chamber.

FIG. 24 depicts a schematic of the example target substance analysis system of FIG. 5 during an optical measurement of the contents of the optical measurement chamber. The optical measurement chamber 546 may, for example, be a cuvette or other vessel that allows for the contents within to be optically analyzed. For example, an optical measurement device 552 may illuminate the optical measurement chamber 546 with light of a wavelength that causes any adduct that is present within the optical measurement chamber 546 to fluoresce and emit light of a different wavelength; the optical measurement device 552 may have one or more photodetectors or other sensors that are configured to measure the intensity of the emitted fluorescence, thereby providing a measurement indicative of the amount of adduct (and THC) present in the sample.

Such optical measurement may be made by optically stimulating the adduct using light having a first set of wavelengths and then measuring the amount of light having a second set of wavelengths that is then emitted by the THC adduct in the sample in response to such optical stimulation.

Such optical measurement readings may involve a multi-step process. To begin with, the temperature of the photodetector may be measured for a brief period of time, e.g., 100 ms, and then an optical measurement may be obtained without any illumination of the sample in the optical measurement chamber 546, e.g., for a 100 ms period. The temperature reading may be used to assist in calibrating the output of the photosensor, if necessary (for example, photosensor output voltage may depend on both photosensor temperature and the amount of light that is detected). Subsequent to such a "dark" reading, a "light" reading may be obtained, e.g., one in which the sample is illuminated by the optical source or photoemitter that is used. Again, this may be for a period of time, e.g., 100 ms. The "dark" reading, e.g., the average "dark" reading, may be subtracted from the "light" reading, e.g., the average "light" reading, in order to compensate for any noise-related effects that may affect the results.

In this example, the negative control is a true negative sample, i.e., there is no THC present (and thus no adduct will be formed). Thus, the optical measurement will generally result in a reading of zero, although there may be some low-level luminescence at the frequencies of interest due, for example, to potential contaminants or other sources of light in the sample solution. If present, these low-level luminescence readings may serve as a baseline of what a "zero" reading should correspond to.

Figure 25:
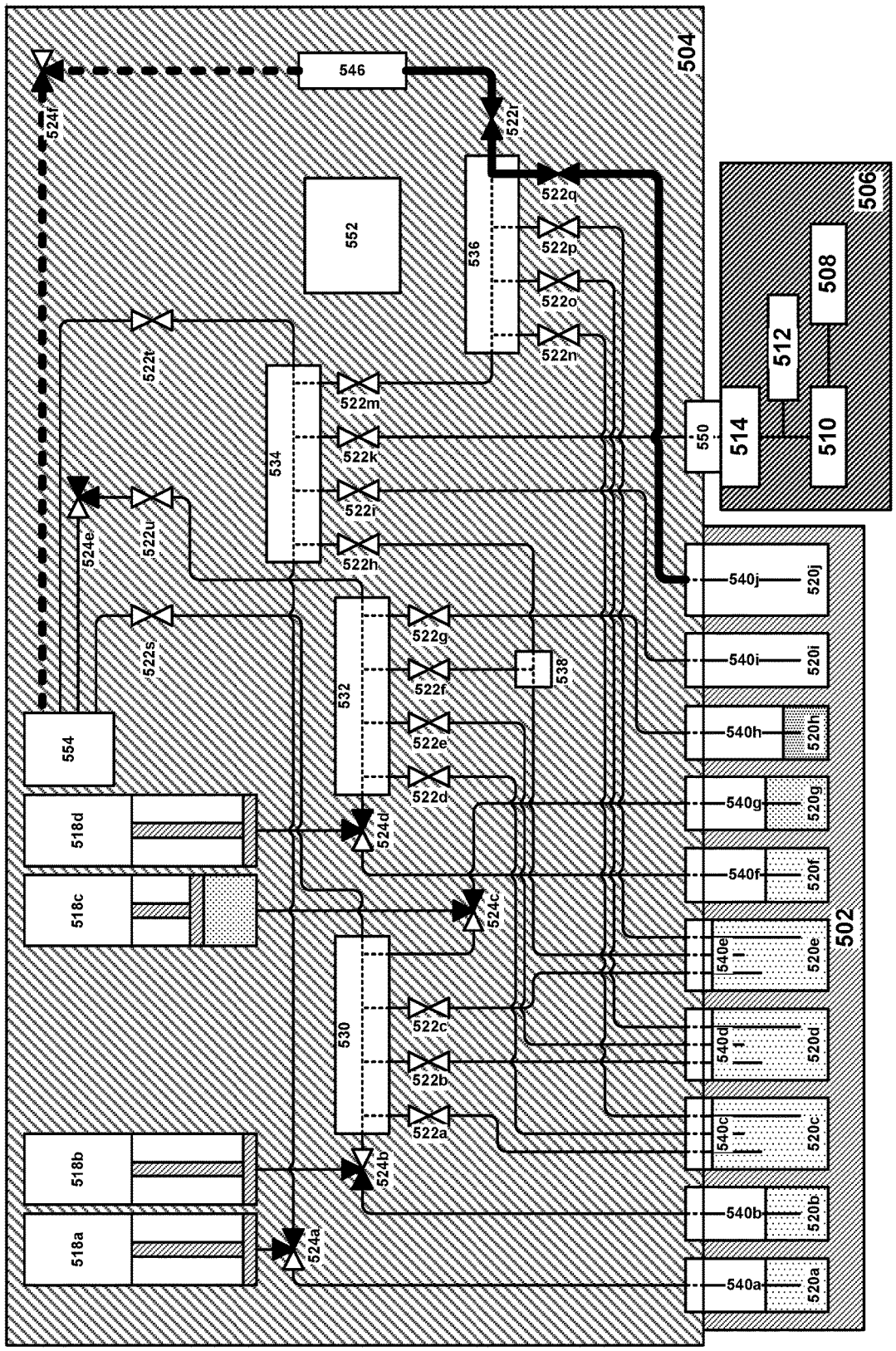
FIG. 25 depicts a schematic of the example target substance analysis system of FIG. 5 during purging of the contents of the optical measurement chamber to a waste reservoir.

FIG. 25 depicts a schematic of the example target substance analysis system of FIG. 5 during purging of the contents of the optical measurement chamber to a waste reservoir. After an optical measurement indicating the amount of adduct that is present in the optical measurement chamber 546 has been obtained, the optical measurement chamber 546 may be purged by opening valves 522r and 522q and pressurizing the optical measurement chamber 546 with air from the air pump 554. This may force the analyzed contents of the optical measurement chamber 546 to be driven into the waste reservoir 520j.

Figure 26:
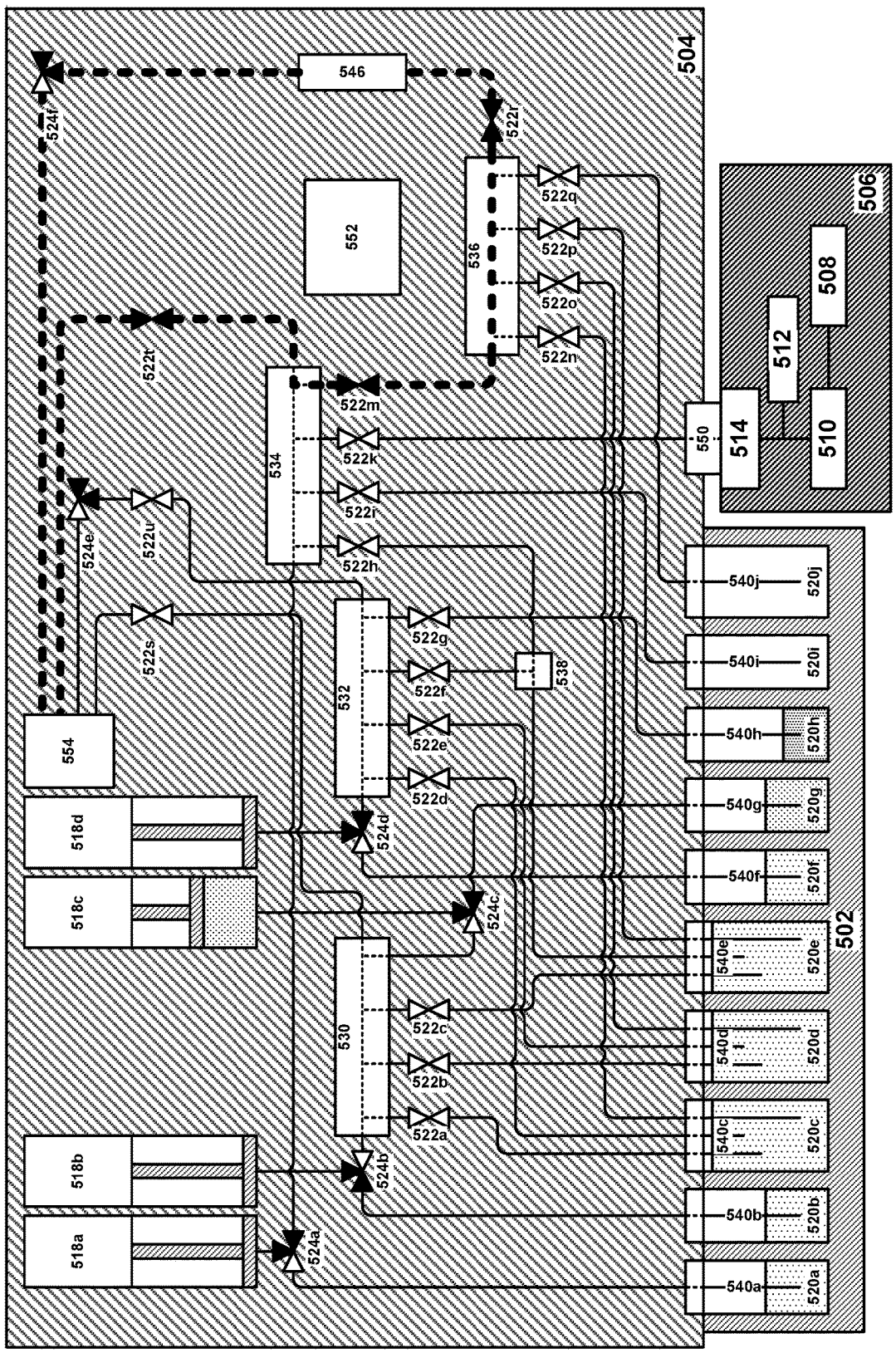
FIG. 26 depicts a schematic of the example target substance analysis system of FIG. 5 during cleaning and drying of various fluid flow paths.

FIG. 26 depicts a schematic of the example target substance analysis system of FIG. 5 during cleaning and drying of various fluid flow paths. After the optical measurement chamber 546 has been emptied of its contents, the various valves 522 and 524 may be opened and close to cause air from the air pump 554 to be routed through the various fluid flow paths for various periods of time in order to remove any remaining fluids and evacuate, to the extent possible, any remaining residues so that contamination of the next fluid sample, e.g., either the sample itself or the positive control, to be delivered to the optical measurement chamber 546 is reduced or eliminated.

Figure 27:
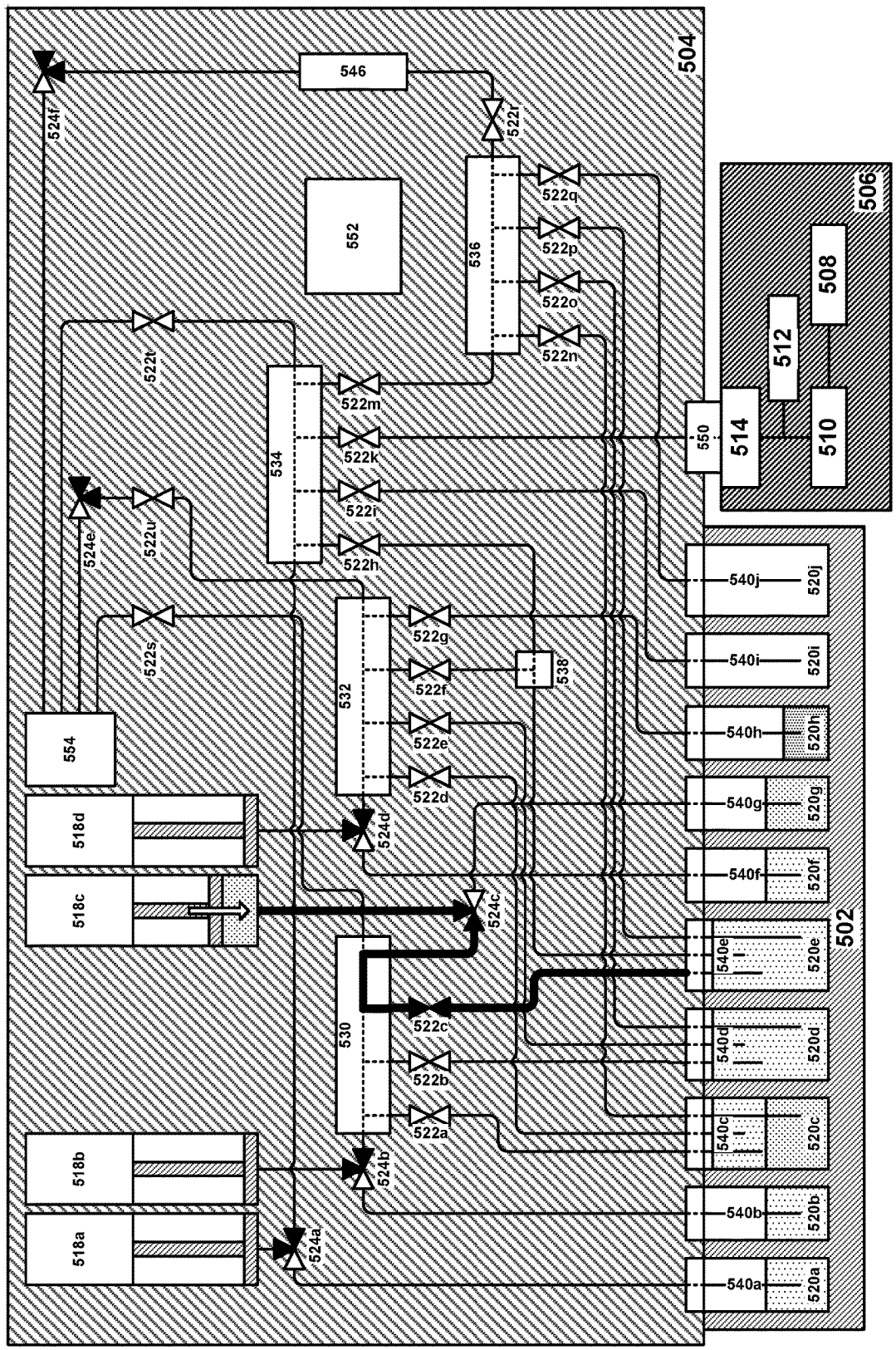
FIG. 27 depicts a schematic of the example target substance analysis system of FIG. 5 during dispensing of an activator to the sample mixing chamber.

FIG. 27 depicts a schematic of the example target substance analysis system of FIG. 5 during dispensing of an activator to the sample mixing chamber. The dispensation of the activator to the sample mixing chamber 520e may occur in generally the same manner as the dispensation of the activator to the negative control mixing chamber 520c, discussed earlier.

Figure 28:
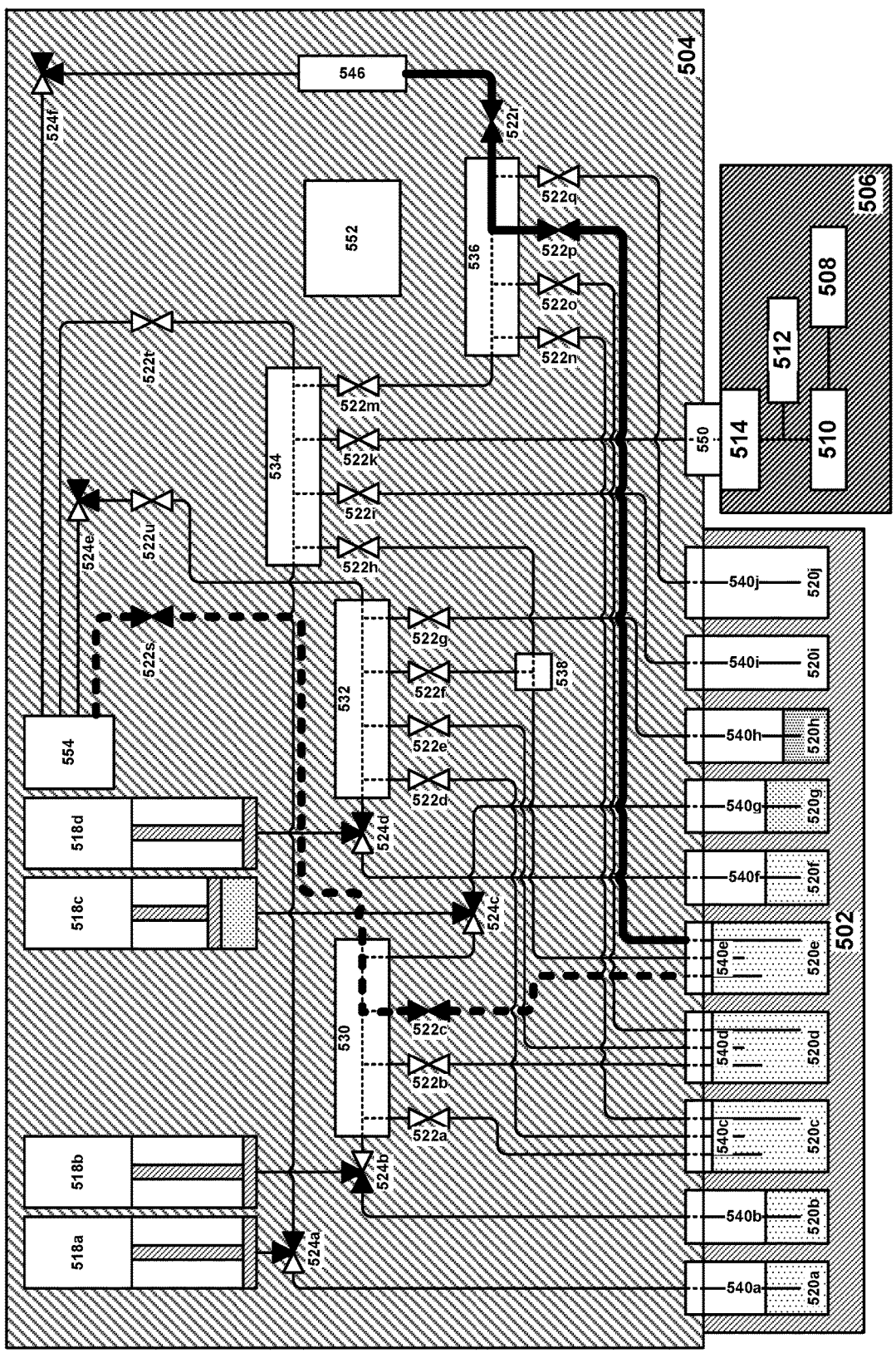
FIG. 28 depicts a schematic of the example target substance analysis system of FIG. 5 during dispensation of the sample to the optical measurement chamber.

FIG. 28 depicts a schematic of the example target substance analysis system of FIG. 5 during dispensation of the contents of the sample mixing chamber to the optical measurement chamber. Dispensation of the contents of the sample mixing chamber 520e to the optical measurement chamber 546 may occur in generally the same manner as dispensation of the contents of the negative control mixing chamber 520c to the optical measurement chamber 546. Subsequent to the delivery of the contents of the sample mixing chamber 520e to the optical measurement chamber 546, the contents of the optical measurement chamber 546 may be measured using the optical measurement device 552 and then, after the measurement has been obtained, emptied into the waste reservoir 520j, followed by air drying of the fluid flow lines (similar to the operation discussed with respect to FIGS. 24 through 26).

Figure 29:
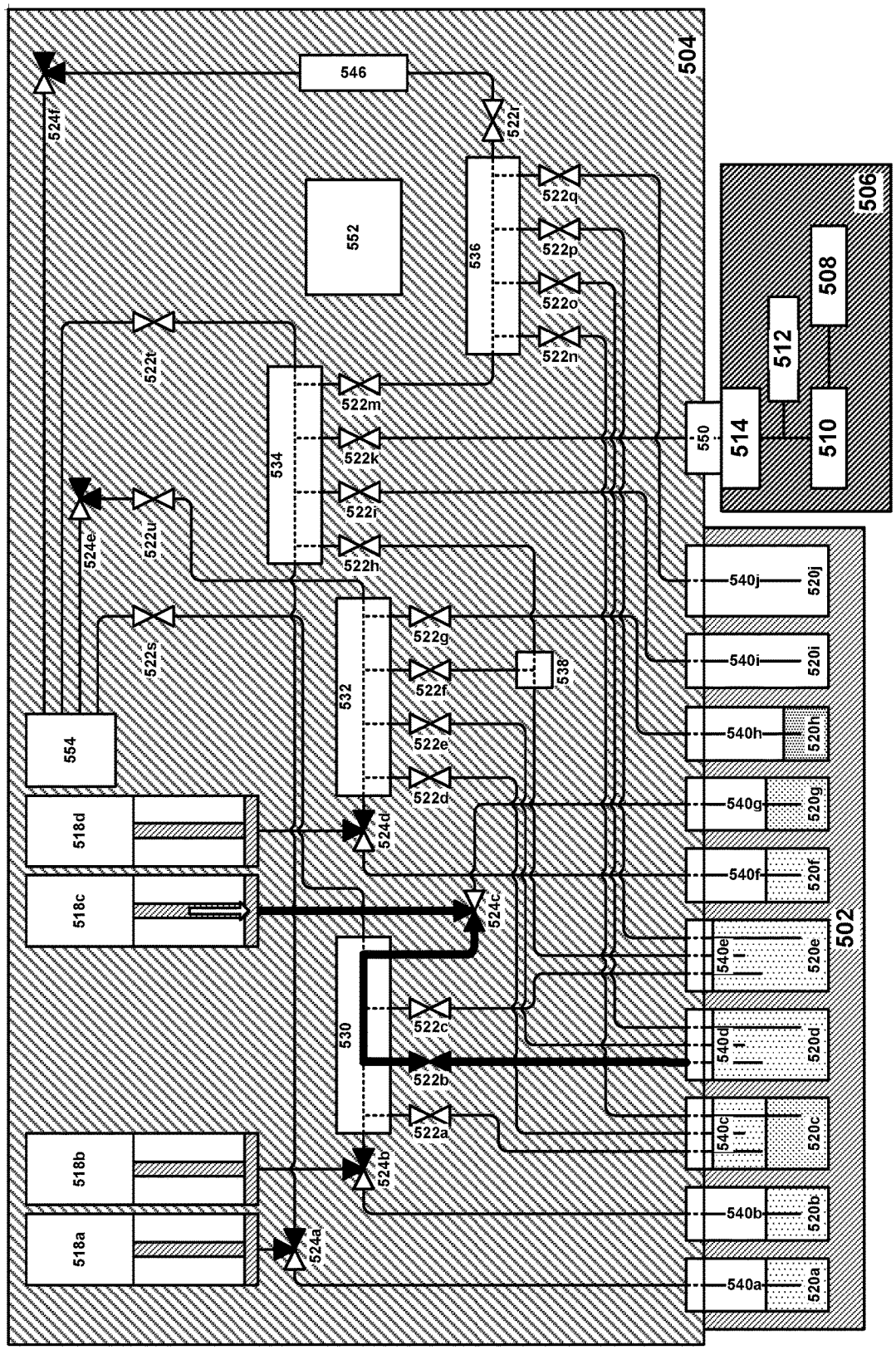
FIG. 29 depicts a schematic of the example target substance analysis system of FIG. 5 during dispensing of an activator to the positive control mixing chamber.

FIG. 29 depicts a schematic of the example target substance analysis system of FIG. 5 during dispensing of an activator to the positive control mixing chamber. The dispensation of the activator to the positive control mixing chamber 520d may occur in generally the same manner as the dispensation of the activator to the negative control mixing chamber 520c and the sample mixing chamber 520e, discussed earlier.

Figure 30:
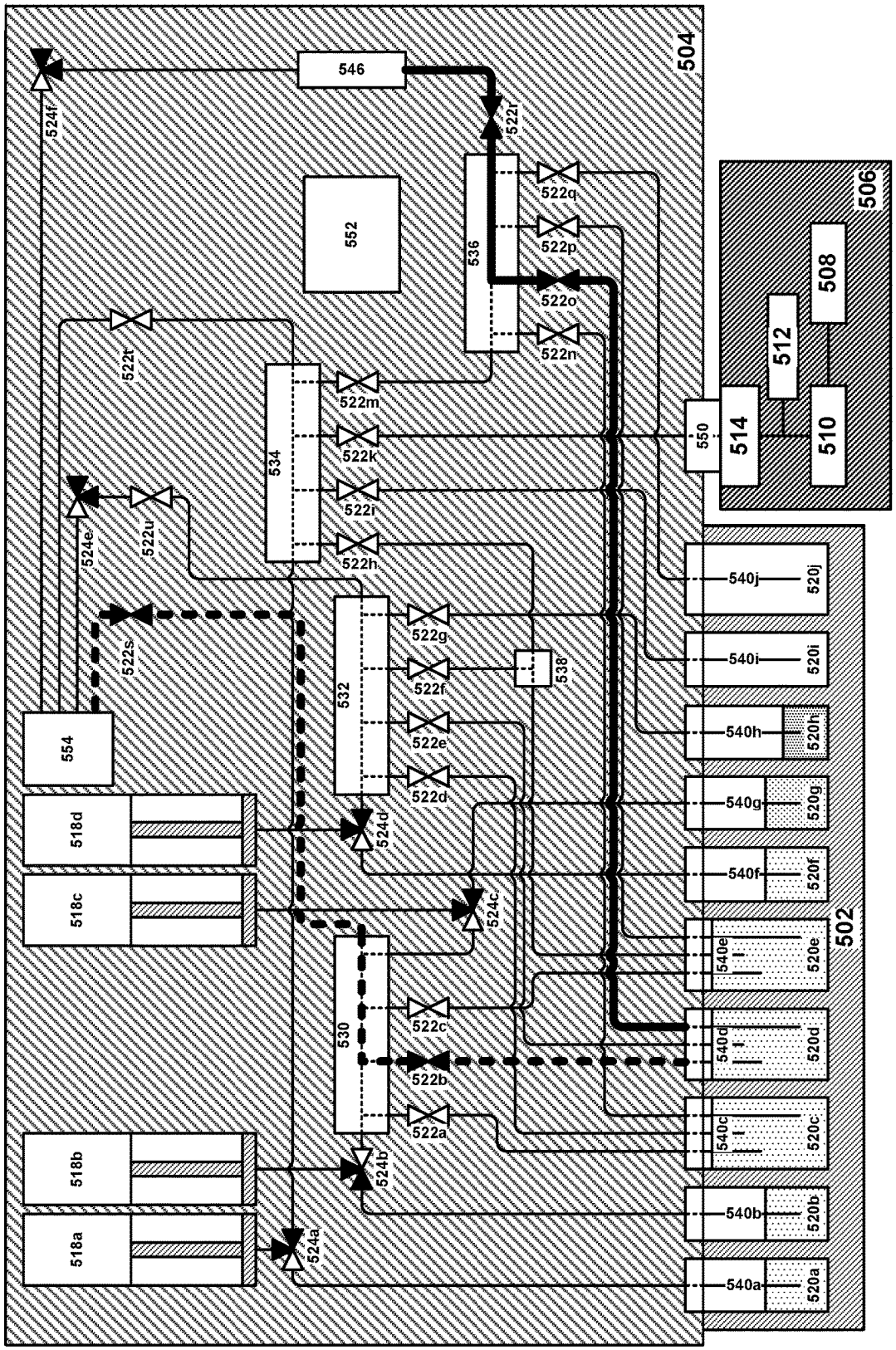
FIG. 30 depicts a schematic of the example target substance analysis system of FIG. 5 during dispensation of the positive control to the optical measurement chamber.

FIG. 30 depicts a schematic of the example target substance analysis system of FIG. 5 during dispensation of the positive control to the optical measurement chamber. Dispensation of the contents of the positive control mixing chamber 520e to the optical measurement chamber 546 may occur in generally the same manner as dispensation of the contents of the negative control mixing chamber 520c or of the sample mixing chamber 520e to the optical measurement chamber 546. Subsequent to the delivery of the contents of the positive control mixing chamber 520e to the optical measurement chamber 546, the contents of the optical measurement chamber 546 may be measured using the optical measurement device 552 and then, after the measurement has been obtained, emptied into the waste reservoir 520j, followed by air drying of the fluid flow lines (similar to the operation discussed with respect to FIGS. 24 through 26).

After obtaining the optical measurements of the positive control, the negative control, and the sample, the positive control and negative control measurements may be used to determine a function that relates measured light intensity to the amount of THC present, which may then be used to estimate the amount of THC present in the sample based on the measured light intensity of the sample.

Figure 31:
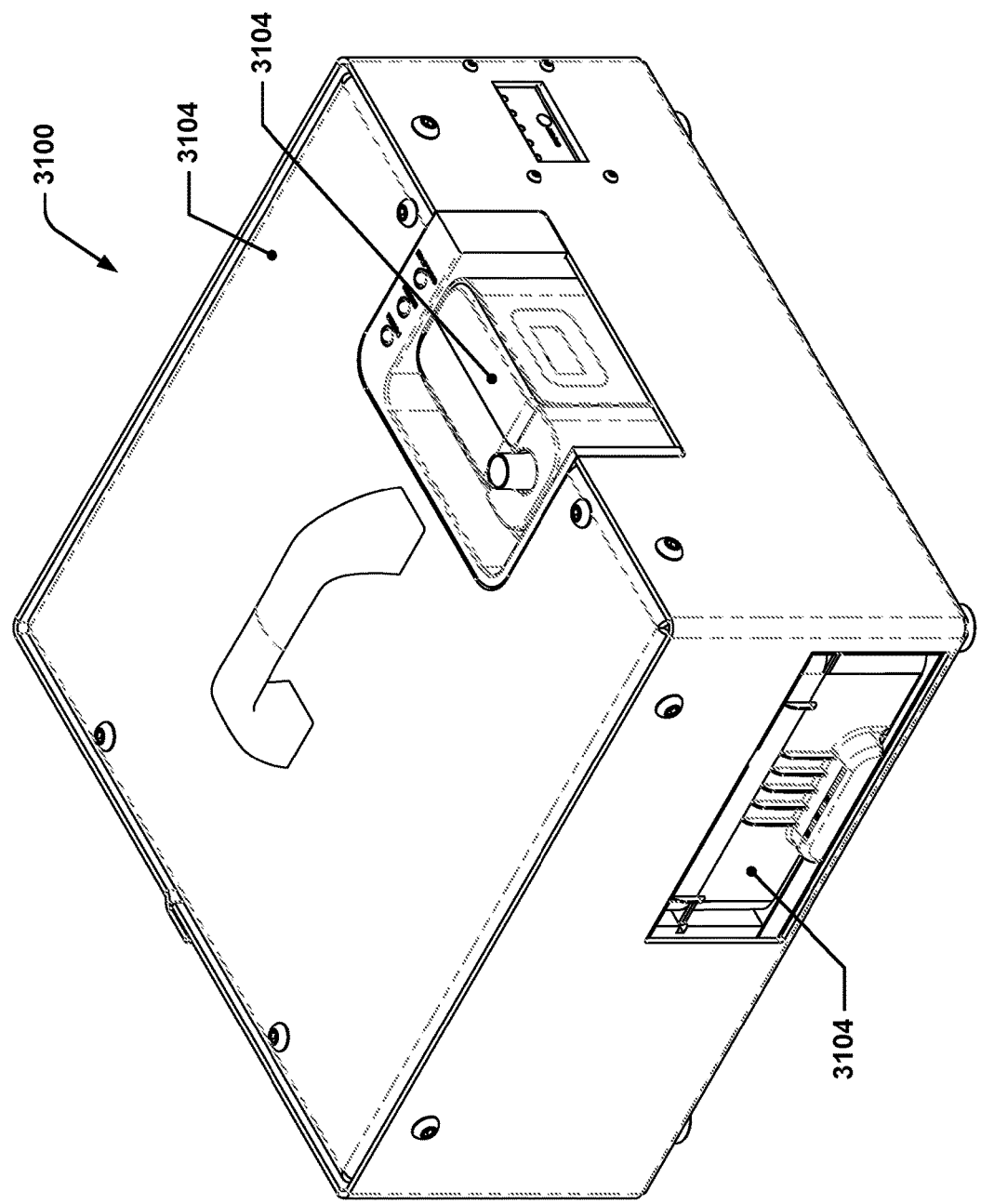
FIG. 31 depicts an isometric view of an example target substance analysis system.

FIG. 31 depicts an isometric view of an example target substance analysis system. The analysis unit 3100 may include a base station 3104 that may have a reagent cartridge 3102 (shown inserted but not yet loaded in this view) and a handheld sample collection unit 3106.

Figure 32:
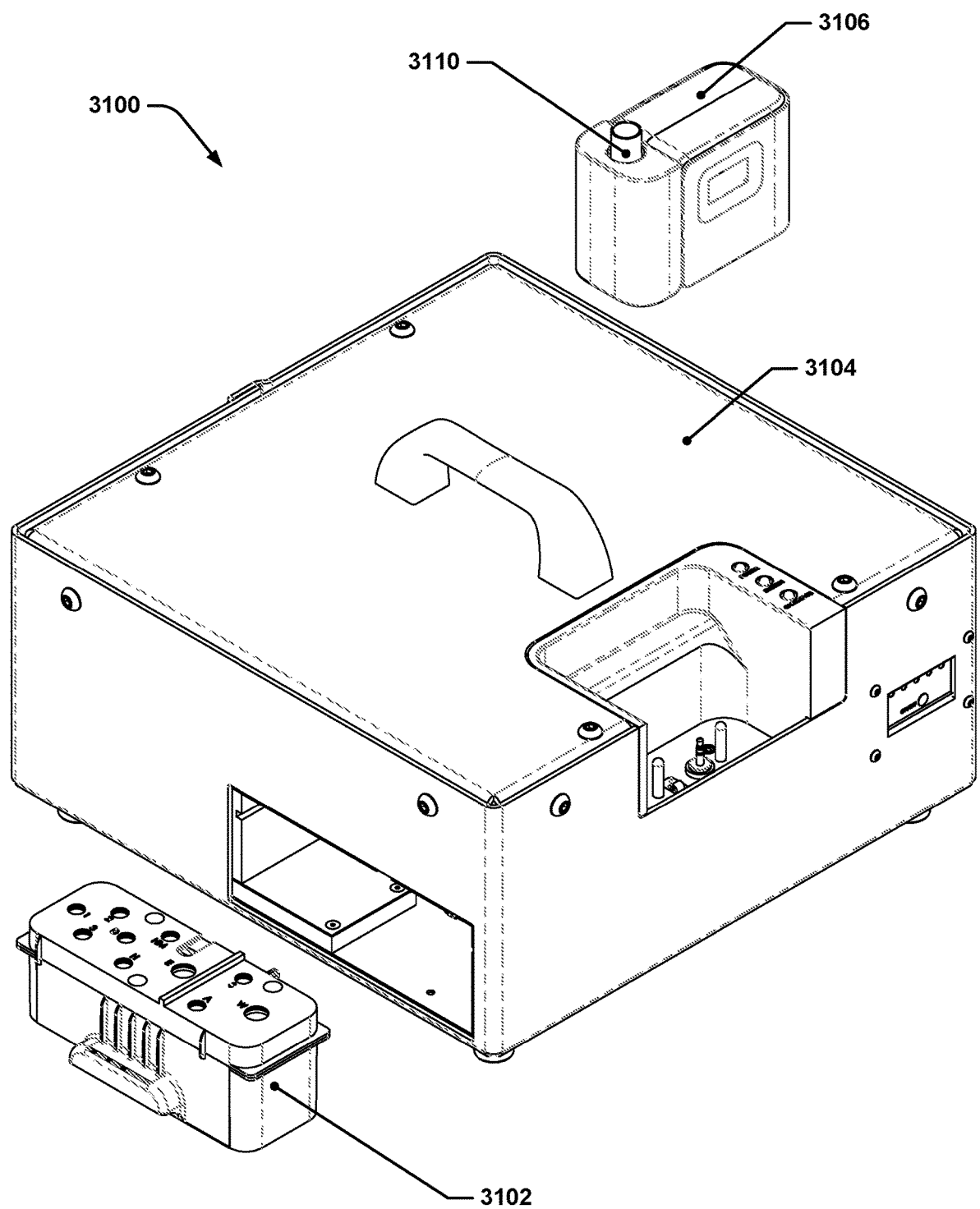
FIG. 32 depicts an isometric view of the example target substance analysis system of FIG. 31 with a reagent cartridge and handheld sample collection unit removed.

FIG. 32 depicts an isometric view of the example target substance analysis system of FIG. 31 with a reagent cartridge and handheld sample collection unit removed. The handheld sample collection unit 3106 may have a mouthpiece 3110 that a subject may blow in to cause exhaled breath to pass through the handheld sample collection unit 3106 and a BCM contained therein. The mouthpiece 3110, in this example, includes a saliva trap as well.

Figure 33:
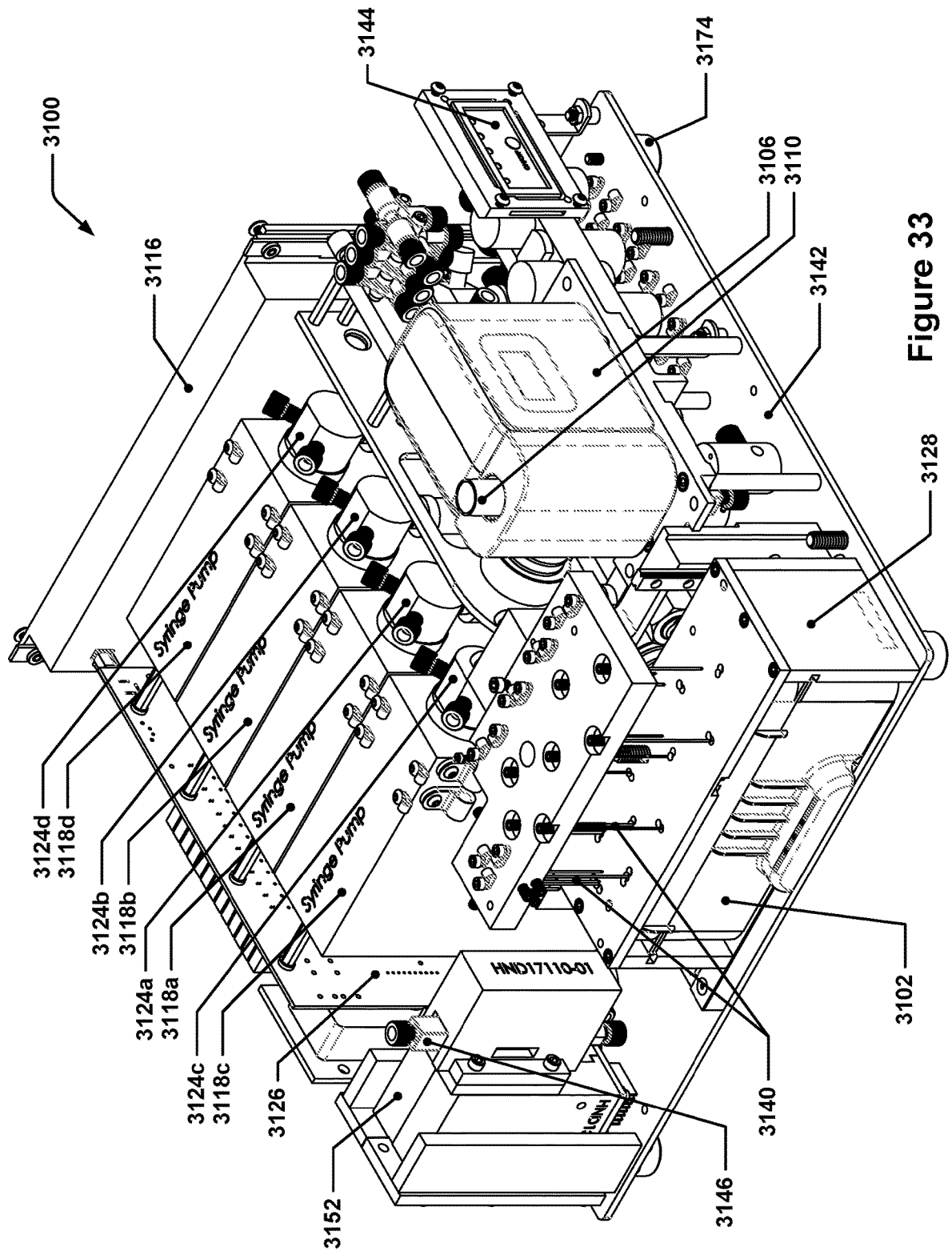
FIG. 33 depicts an isometric view of the example target substance detection system of FIG. 31 with the housing removed.

FIG. 33 depicts an isometric view of the example target substance detection system of FIG. 31 with the housing removed. With the housing removed, various internal components are visible. The components shown may generally correspond to the components depicted in FIGS. 5 through 30 and discussed above. For convenience, components in FIGS. 31 through 46 that correspond to similar schematically illustrated components in FIGS. 5 through 30 are called out with callouts having the same last two digits and, if used, alphabetic suffix; the functionality of such components, if not otherwise described below, may be assumed to be similar to the functionality of the corresponding components in FIGS. 5 through 30.

It is to be understood that the actual fluidic connections and flow paths, e.g., tubes, running between the various depicted components are not depicted, as doing so would likely obscure various other components of the analysis unit 3100 and would provide little practical insight due to the difficulty of being able to discern which tube went where. Similar such fluidic flow paths are, however, diagrammatically illustrated in FIGS. 5 through 30, and the reader is referred to the fluidic flow paths between the components of FIGS. 5 through 30 for reference (again, like components in FIGS. 5 through 30 and in FIGS. 31 through 46 have callouts that share the same last two digits and, if applicable, alphabetic suffix).

Visible in FIG. 33 are an eluent pump 3118a, an organic solvent pump 3118b, an activator pump 3118c, and an indicator pump 3118d, which may each be configured to pump fluids through a corresponding 3-way valve 3124a, 3124b, 3124c, or 3124d. The base station 3104 may also include a printed circuit board (PCB) 526 that may house one or more memories, one or more processors, input/output interfaces, sensors, valve drivers, and various other electronic components that may be used to control or communicate with the various components that are part of the analysis unit 3100. A battery 3116, e.g., a rechargeable battery, may provide electrical power to the analysis unit 3100. Alternatively or additionally, the analysis unit 3100 may have an external power connection to allow the analysis unit 3100 to be operated using a standard wall outlet or to allow the analysis unit 3100 to be recharged.

Also visible in FIG. 33 are an optical measurement device 3152 and an optical measurement chamber 3146. The optical measurement chamber 3146 may, for example, be a cuvette or other vessel that may contain a liquid and allow fluorescence from that liquid to be measured by the optical measurement device 3152. The optical measurement device 3152 may include, for example, one or more photodetectors and one or more light sources or emitters, and may be configured to illuminate the liquid in the optical measurement chamber 3146 with the one or more light sources using light of predominantly a first wavelength or wavelengths and then measure the intensity of light at a second wavelength or wavelengths that is emitted from the liquid in the optical measurement chamber 3146 in response to stimulation by the light of the first wavelength or wavelengths. In some implementations, the optical measurement device may operate using different principles; generally speaking, any suitable optical measurement device may be used to obtain measurements of the amount and/or intensity of light that is produced by fluorescence of the adduct. It is to be understood that other types of optical sensors may be used as well, and that some optical sensors may, depending on the particular adduct used, not include a photoemitter, e.g., in implementations where the THC adduct does not require optical pumping in order to emit light. For example, if the THC adduct that is produced fluoresces when exposed to other types of electromagnetic radiation, or in response to electrical excitation, or some other non-optical stimulus, then the photoemitter may be omitted.

FIG. 33 also depicts a cartridge loader 3128, which may serve as a reagent cartridge receptacle, of the base station 3104, and may include a number of fluidic interfaces 3140. The reagent cartridge 3102 may be inserted into the cartridge loader 3128 for loading. The cartridge loader 3128 is discussed in further detail below with respect to FIGS. 35 through 39.

Also visible in FIG. 33 is the handheld sample collection unit 3106, with the mouthpiece 3110, which is shown in a docked configuration. The base station 3104 may also include one or more indicators or readouts 3144 that may be used to communicate the status of the analysis unit 3100 or otherwise communicate information to the user.

The various components of the base station 3104 may be supported on a base 3142 that rests on feet 3174. The feet 3174 may, for example, be equipped with suction cups or magnets to allow the base station 3100 to be more securely seated on, for example, the roof or hood of a car, such as a police cruiser. For example, during a traffic stop, a police officer may suspect that a person is under the influence of marijuana, and may therefore wish to analyze a breath constituent sample from the person using the analysis unit 3100. The police officer may therefore remove the analysis unit 3100 from his or her police cruiser and place it on the roof, trunk, or hood of the police cruiser for easy access. If the analysis unit 3100 is equipped with magnetic feet or suction cup feet, this may allow the analysis unit 3100 to be firmly seated in place on such a surface and may prevent the analysis unit 3100 from slipping, falling, being jostled, or otherwise moving. In some implementations, the analysis unit 3100 may include further features, discussed later herein, to allow the analysis unit 3100 to be leveled or to otherwise indicate when the analysis unit 3100 is not level, as having the analysis unit 3100 non-level may, in some implementations, adversely affect the analysis being performed.

FIG. 34 depicts an isometric exploded view of the example target substance detection system of FIG. 31 (without the housing). Many of the same components shown in FIG. 33 are visible in FIG. 34, although additional components are also visible. For example, a handheld dock 3148 is shown, on which the handheld sample collection unit 3106 may be placed when docked in the base station 3104. The handheld dock 3148 may include an elution port 3150, which may interface with the BCM in the handheld sample collection unit 3106 to allow the eluent to be introduced into, and withdrawn from, the BCM.

Also more clearly visible in FIG. 34 are various manifolds and valves. For example, valves 3122a-3122u (with 3122l and 3122j omitted for consistency with the designations used in FIGS. 5 through 30) are shown, as are 3-way valves 3124a through 3124f. Some of the valves 3122 are discrete valves, such as valves 3122a through 3122c and valves 3122n through 3122s, whereas other valves 3122 may be included as part of a manifold or other component. For example, valves 3122d through 3122g and valve 3122u are shown as valves that are integrated into an indicator manifold 3132, whereas valves 3122h, 3122i, 3122k, 3122m, and 3122t are shown as valves that are integrated into an elution manifold 3134. Also visible in FIG. 34 are an activator manifold 3130, which in this case, consists of two four-port crosses that are fluidically linked with one another via a port on each (to provide a six-port manifold), an optics manifold 3136, which, in this case, consists of two four-port crosses 3136a and 3136a that may be similarly linked, and a T-manifold 3138, as well as an air pump 3154.

FIGS. 35 through 37 depict an isometric view of an example reagent cartridge receptacle assembly for the example target substance detection system of FIG. 31 during various stages of reagent cartridge loading. The reagent cartridge receptacle assembly or cartridge loader 3128 may include an elevator 3176 that is configured to receive the reagent cartridge 3102, which is inserted in FIG. 36. The elevator 3176 may include features to guide an align the reagent cartridge 3102, such as slots 3178 relative to the elevator 3176 so that when the elevator 3176 is raised vertically, the fluidic interfaces 3140 of the cartridge loader 3128 are properly positioned relative to the reservoirs and mixing chambers of the reagent cartridge 3102.

The fluidic interfaces 3140, in this case, each include one to three hollow needles, probes, or tubes that may pierce thin septums, e.g., thin metal foils or elastomeric membranes, that are used to seal each reservoir or mixing chamber in the reagent cartridge 3102. In some implementations, such as the one depicted, several of the fluidic interfaces may include at least two such needles, probes, or tubes—one that may be used to transfer fluids to and/or from the interfaced reservoir or mixing chamber, and the other to serve as a vent to the ambient environment that allows the reservoir or mixing chamber in question to generally remain at atmospheric equilibrium so as to prevent the buildup of pressure or the creation of a vacuum during fluid transfer operations.

In some fluidic interfaces, such as the fluidic interfaces 3140c through 31e, there may be three such probes, needles, or tubes that may be used to transfer fluids to and/or from the interfaced mixing chamber or reservoirs. For example, in the fluidic interfaces 3140c through 31e, at least one of the probes, needles, or tubes, may have a length that is designed such that the tip of that probe, needle, or tube will be submerged in the non-polar layer of the separated sample or control (after addition of the organic solvent and indicator and subsequent mixing, followed by addition of the activator and subsequent separation operations discussed earlier) without extending into the polar layer of the separated sample or control. If air pressure is used to drive fluids to or from a reservoir or mixing chamber, then the probe, needle, or tube used to supply that pressurized air may be designed to have a length that does not extend into any of the fluids within the interfaced reservoir or mixing chamber so as to avoid creating bubbles that may complicate optical analysis later. Moreover, if air pressure is used to drive fluids to or from a reservoir or mixing chamber, whatever vent path there is via the fluidic interface for that reservoir or mixing chamber, if any, may be connected with a valve to allow the vent path to be selectively closed, as needed. For example, if air pressure is used to pressurize the contents of a mixing chamber to force fluid contained therein to flow into a needle or probe that is immersed in that fluid and thereby be delivered to another location, having an open vent to the reservoir or mixing chamber would generally interfere with such an operation since the pressurized air might escape via the vent quickly enough that it would be impossible to actually develop the necessary pressure environment to effect the pumping of the fluid. If the vent is closed using a valve during such pumping operations, however, this would remedy this issue.

In some implementations, special configurations of needles and septa may be used to reduce the possibility of operational complications. For example, it was found during testing that raising the reagent cartridge 3102 up so that all 23 needles (each of the three mixing chambers—aside from the indicator mixing chamber—included 3 needles, and each of the remaining reservoirs or mixing chambers included 1 needle for fluid transfer and a separate needle for venting to prevent vacuum/pressurization due to fluid transfer) pierced the septa of the reagent cartridge 3102 required significant force.

In order to address this issue, the septa of the reagent cartridge 3102 were customized to be a sandwich of three layers that were bonded together: a PTFE layer, followed by a silicone layer, followed by another PTFE layer. In a standard septum configuration, such as may be used in a vial holding medication, the septum is typically only two layers, with the interior-facing layer being PTFE and the exterior-facing layer being silicone. The PTFE layer is inert and is sealed to the vial to protect the contents thereof from contamination. When a needle is inserted through the PTFE layer and then withdrawn, a hole will remain, allowing fluid to escape from the vial or be exposed to contaminants. The silicone layer in such a septum acts as a "self-healing" layer that, due to its high elasticity, will seal up again after the needle is removed. Thus, the PTFE layer acts as a non-reactive, long-term seal, and the silicone layer acts as a short-term, self-healing seal.

During testing, it was found that needle insertion force could be reduced by including another layer of PTFE in each septum such that the silicone layer was sandwiched between the two PTFE layers (with all three of the layers bonded together). When a needle is inserted into PTFE, it causes plastic deformation, whereas a needle inserted into silicone may only cause elastic deformation—thus, the insertion force through the silicone layer may actually be higher than for the PTFE layer in a standard 2-layer septum. However, if the first layer pierced by the needle is also a PTFE layer, then the inserted needle may experience reduced insertion force even when passing through the silicone layer. This is believed to be due to the fact that the plastic deformation of the initial PTFE layer may also act to elastically deform the underlying silicone layer (which is bonded thereto), thereby reducing the amount of elastic deformation of the silicone layer that the needle will need to provide as it passes through the silicone layer—thus reducing insertion force. As an example, septa with PTFE layers that are 0.003"±0.001" thick (each) sandwiching a 0.054"±0.003" thick silicone layer yielded good results in the example system. Septa with different thickness layers may potentially also provide good performance, e.g., thicknesses that are ±10%, ±20% or ±30% of the values discussed above.

In implementations using needles, the needles may be selected to reduce the possibility of "coring" in some instances. Coring occurs when a hollow needle is inserted through a septum and "cores" out a plug of silicone from the septum, much like an ice corer or hole saw would. In the implementations discussed herein, such cores may, in many cases, be purged from the needle by moving fluids through them to push the cores out. However, certain needles may not be able to be purged in this manner, e.g., the needles used for siphoning out the activated adduct solutions from the mixing chambers for transfer to the optical measurement chamber. These needles are, at least in the depicted implementations, not connected with a pump system that acts on an incompressible fluid, and this makes it difficult to purge such cores from such needles. In such cases, side-port needles may be used instead of the more conventional bevel needles (a bevel needle is a hollow tube that has been cut at a shallow angle relative to the tube centerline so as to create a sharp point; such needles allow septum material to travel along the centerline of the needle and into the hollow interior of the needle, thereby presenting the possibility of coring). A side-port needle is a hollow needle that has been welded shut at the end (usually forming a duller point than a bevel needle) and that has a small hole in the side of the needle near the point that leads to the hollow interior—since the silicone can only be pushed into the hole from a direction perpendicular to the axis of insertion, there is little or no chance of coring occurring during insertion.

FIG. 38 depicts an example septum and needle configuration consistent with the implementations discussed above. Septum 3896 includes two PTFE layers 3897a/b sandwiching a silicone layer 3898 (all bonded together). A needle 3899 includes a side-located hole 3895. Such a configuration provides for non-coring penetration of the septum 3896 by the needle 3899 with reduced force as compared with traditional 2-layer septa.

FIG. 39 depicts an isometric exploded view of the example reagent cartridge receptacle assembly shown in FIGS. 35 through 37. The guide rails 3156, which may be attached to a support structure 3182, are more clearly visible in FIG. 39, and it may be seen that the guide rails 3156 generally constrain the elevator 3176 such that the elevator 3176 can only be moved vertically relative to the support structure 3182 and the fluidic interfaces 3140.

The cartridge loader 3128 may also have one or more sensors and/or safety interlocks to ensure proper loading the reagent cartridge 3102 and to prevent inadvertent or improper operation of the cartridge loader 3128. For example, the cartridge loader 3128, in this example, includes a cartridge lock solenoid 3172 and a cartridge load switch 3170. The cartridge lock solenoid 3172 may be activated so as to interlock with different holes or recesses on the elevator 3176 depending on whether the elevator 3176 is in the lowered state (in which the reagent cartridge 3102 may be inserted into it) or the raised state (in which the fluidic interfaces 3140 are interfaced with the reservoirs and mixing chambers of the reagent cartridge 3102). When the cartridge lock solenoid 3172 is engaged with one of these holes or recesses, it may prevent the elevator 3176 from being moved further, thereby preventing accidental interruption of the analysis or potential contamination of the system by external substances. The cartridge load switch 3170 may detect when a cartridge has been inserted into the elevator 3176; such an indication may cause the controller of the analysis unit 3100 to cause the cartridge lock solenoid 3172 to disengage to allow the elevator 31 76 to be moved up so that the reagent cartridge 3102 is fully interfaced with the fluidic interfaces 3140. Another cartridge load switch (or, in some cases, even the same cartridge load switch 3170), may provide another signal that indicates when the elevator 3176 has been moved up far enough that the fluidic interfaces 3140 are fully interfaced with the reagent cartridge 3102, in which case the controller may cause the cartridge lock solenoid 3172 to re-engage with the elevator 3176 to prevent further movement thereof until the analysis is complete.

The elevator 3176, in some implementations, may include a guard plate 3180 that forms the "roof" of the elevator 3176 and that walls off the area with the fluidic interfaces 3140 from accidental contact, e.g., with an operator's fingers. For example, in the lowered position, the fluidic interfaces 3140 will be located above the guard plate 3180 and the guard plate 3180 will thus prevent, for example, fingers that are placed within the elevator 3176 from being able to contact the needles or other probes of the fluidic interfaces 3140. When the elevator 3176 is in the raised position, the needles or probes of the fluidic interfaces 3140 may pass through the guard plate 3180 and into the elevator 3176 where they will pass into the reservoirs and mixing chambers of the reagent cartridge 3102. Since the cartridge lock solenoid 3172 may generally prevent such upward movement of the elevator 3176 unless the reagent cartridge 3102 is installed in the elevator 3176, this may foreclose the possibility that a user may accidentally stab themselves with one of the probes or needles of the fluidic interfaces 3140.

In some implementations, the elevator 3176 may also include an integrated mixing device or mixer 3158. In the depicted implementation, for example, the mixer 3158 is a magnetic stir-bar mixer in which a cluster of pulleys 3162 in the mixer 3158 are driven by a mixer motor 3160 by a belt 3168 so that the pulleys 3162 rotate in unison. Each pulley 3162 may have one or two magnets 3164 that are positioned such that the magnetic field that the magnets produce causes a stir-bar 3166 in a corresponding one of the mixing chambers to rotate in the same manner as the pulley 3162, thereby mixing the contents of that mixing chamber. The mixer 3158 may travel with the elevator 3176 and may be positioned such that the pulleys 3162 of the mixer 3158 are each located beneath a correspond one of the mixing chambers in the reagent cartridge 3102 when the reagent cartridge 3102 is inserted into the elevator 3176.

As can be seen, the reagent cartridge 3102, in this example, has a two-part housing that includes within it a plurality of small glass vials, each sealed with a septum. The vials may serve as the interior volumes of the reagent cartridge 3102, and may include, for example, an eluent reservoir 3120a, an organic solvent reservoir 3120b, a negative control mixing chamber 3120c, a positive control mixing chamber 3120d, a sample mixing chamber 3120e, an indicator solvent reservoir 3120f, an activator reservoir 3120g, an indicator mixing chamber 3120h, a sample reservoir 3120i, and a waste reservoir 3120j. It will be understood that the reagent cartridge 3102 may also include integrally-formed reservoirs and mixing chambers, e.g., not discrete bottles that are placed into the reagent cartridge 3102, or take any of a variety of other form factors.

Figure 41:
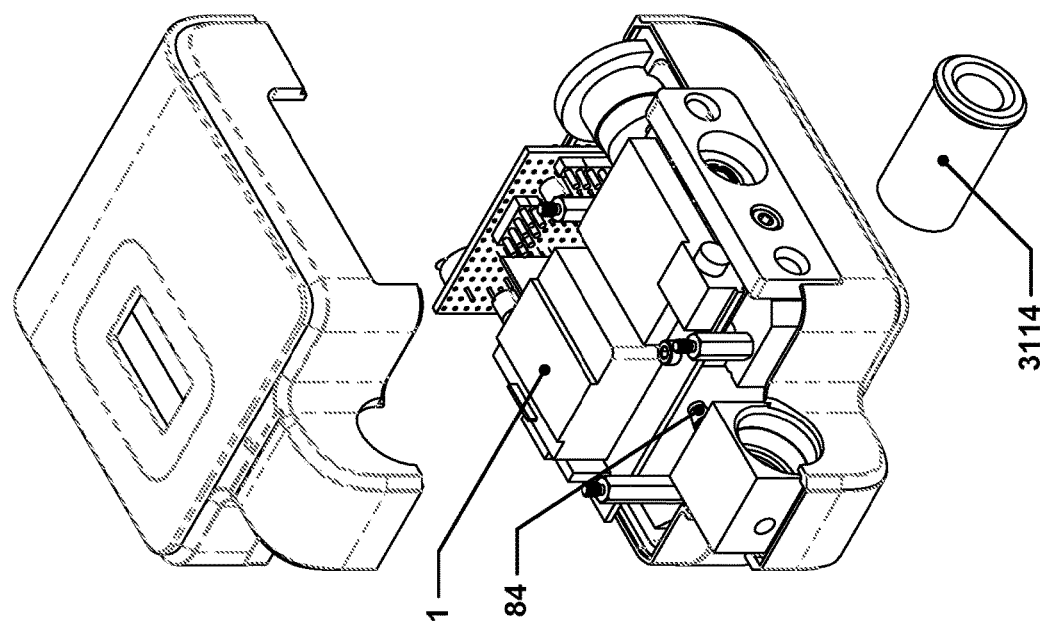
FIG. 41 depicts an isometric exploded view of the example handheld sample collection unit of FIG. 40.
Figure 40:
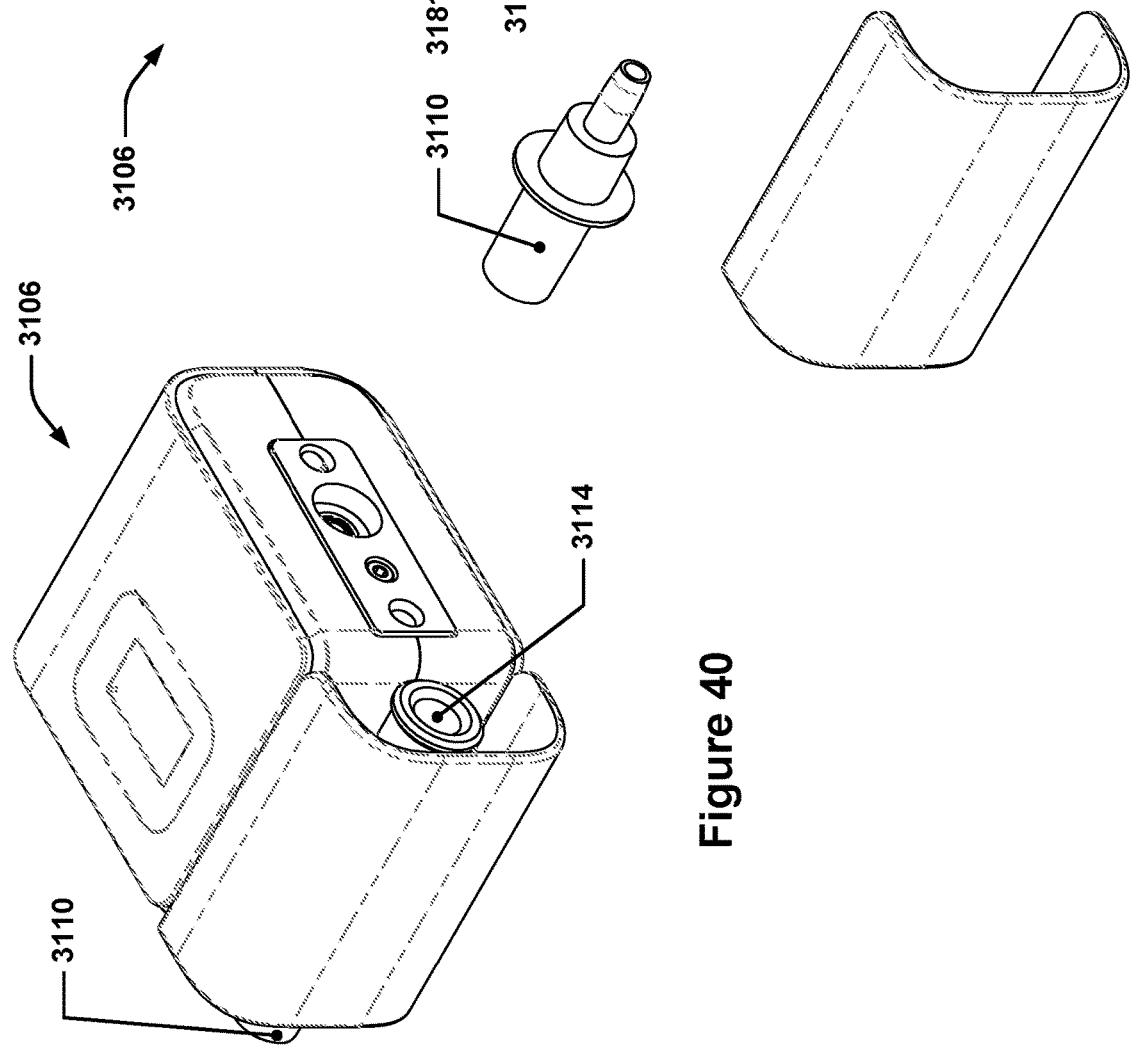
FIG. 40 depicts an isometric view of an example handheld sample collection unit for the example target substance detection system of FIG. 31.

FIG. 40 depicts an isometric view of an example handheld sample collection unit for the example target substance detection system of FIG. 31. FIG. 41 depicts an isometric exploded view of the example handheld sample collection unit of FIG. 40. The handheld sample collection unit 3106 may, for example, have a housing that protects a printed circuit board having a controller, e.g., one or more processors, a memory, a communications interface, etc., that may communicate with the base station 3104 and/or other equipment, e.g., a smartphone, laptop, or other device. The handheld sample collection unit 3106 may include some form of sensor that may be used to measure or estimate the amount of breath sample that is passed through the handheld sample collection unit 3106 during sample collection. In the example handheld sample collection unit 3106, such a sensor is a pressure sensor (not shown) that is connected with a pressure port 3184 by a short length of tubing or other conduit (not shown). The pressure port 3184 may allow for fluidic communication between the pressure sensor and the air flowing through the mouthpiece 3110 and the BCM 3114. By measuring the pressure at the pressure port 3184 throughout the sample collection process, a determination may be made as to the flow rate of the breath through the mouthpiece 3110 and the BCM 3114 over time. The flow rate time history that is obtained in this way may, in combination with other parameters, such as the cross-sectional area of the flow path where the pressure port 3184 is located, allow for the determination of volumetric flow rate, which may be integrated over time to determine the total volume of breath that was flowed through the mouthpiece 3110 and the BCM 3114 during sample collection. When the amount of exhaled breath that passes through the BCM 3114 exceeds a predetermined amount (as determined from the pressure sensor data, or from another sensor providing similar information), e.g., 3 liters, then the one or more processors may cause a signal to be provided that a sufficient sample has been collected, e.g., the handheld sample collection unit 3106 may be caused to emit a "beep" or provide some other sort of indication that a sufficient sample has been collected. After a breath constituent sample is collected in the BCM 3114 of the handheld sample collection unit 3106, the BCM 3114 may be connected to the base station 3104 to allow the breath constituent sample to be drawn out of the BCM 3114 and analyzed by the analysis unit 3100.

In some implementations, the handheld sample collection unit 3106 may also include a blood-alcohol concentration (BAC) sensor 3181 that may have an inlet that is fluidically connected with the BCM 3114 and the mouthpiece 3110 in a manner similar to the pressure port 3184 such that a portion of each breath that flows through the BCM 3114 and the mouthpiece 3110 is diverted to the BAC sensor 3181 to allow a BAC measurement to be obtained while the breath sample is being collected. Such a BAC sensor 3181 may, for example, be a fuel cell type BAC sensor or a semiconductor oxide type BAC sensor. Incorporation of a BAC sensor allows for the simultaneous collection of a breath sample for THC detection and a breath sample for alcohol detection. In contrast to the THC analysis, which would be done after docking the BCM 3114 to the base station, the BAC analysis may be performed concurrently with sample collection, e.g., while the subject is exhaling through the handheld sample collection unit 3106. The results/measurements from the BAC sensor 3181 may be stored, e.g., for later transmission to the base station (or other device), and then combined with whatever the results are from a THC analysis performed by the base station into a single result set later on. See, for example, the disclosures of U.S. patent application Ser. No. 14/997,405 and U.S. Provisional Patent Application Nos. 62/104,813; 62/107,331; and 62/277,854 for further details of such arrangements (all of which are previously incorporated by reference herein).

FIG. 42 depicts an isometric view of an example breath collector module that may be used with the example handheld sample collection unit of FIG. 41. FIG. 43 depicts an isometric cross-sectional view of the example breath collector module of FIG. 41. FIG. 44 depicts an isometric exploded view of the example breath collector module of FIG. 41. The BCM 3114 may, for example, a breath collector module similar to those described in U.S. Patent Application No. 62/337,286, which was mentioned earlier and incorporated herein by reference.

As shown in FIGS. 42 through 44, the BCM 3114 may, in some implementations, have a generally tubular aspect provided by a tubular housing 3192 and a tubular insert 3194 that may be inserted inside of the tubular housing 3192. The tubular housing 3192 may have a stepped internal diameter, with the smaller internal diameter being sized similarly to the internal diameter of the tubular insert 3194 and the larger internal diameter being sized to be slightly smaller than the outer diameter of the tubular insert 3194 so that the tubular insert 3194 may be press-fit into the tubular housing 3192.

The BCM 3114 may include a catch media within it, e.g., a frit, fibrous media such as plastic or glass wool, stacked mesh screens, etc. In the example depicted, the catch media is provided by way of 800 µm average diameter microspheres 3190, which are supported between two mesh screens 3188 and/or filter disks 3186 (shown as solid, but actually permeable, e.g., Technostat® 90 Plus, a meltblown synthetic fiber carried on a spunbond polypropylene backing material that is manufactured by Hollingsworth & Vose of East Walpole, Massachusetts, and distributed in the United States of America by Superior Felt & Filtration of McHenry, Illinois) that are sandwiched between the end of the tubular insert 3194 and the internal ledge of the tubular housing 3192 where the transition occurs between the smaller and larger internal diameters of the tubular housing 3192. During elution, the eluent may be pumped into the BCM 3114 such that the BCM 3114 is filled at least up to the point where the catch media is completely immersed in the eluent.

Figure 46:
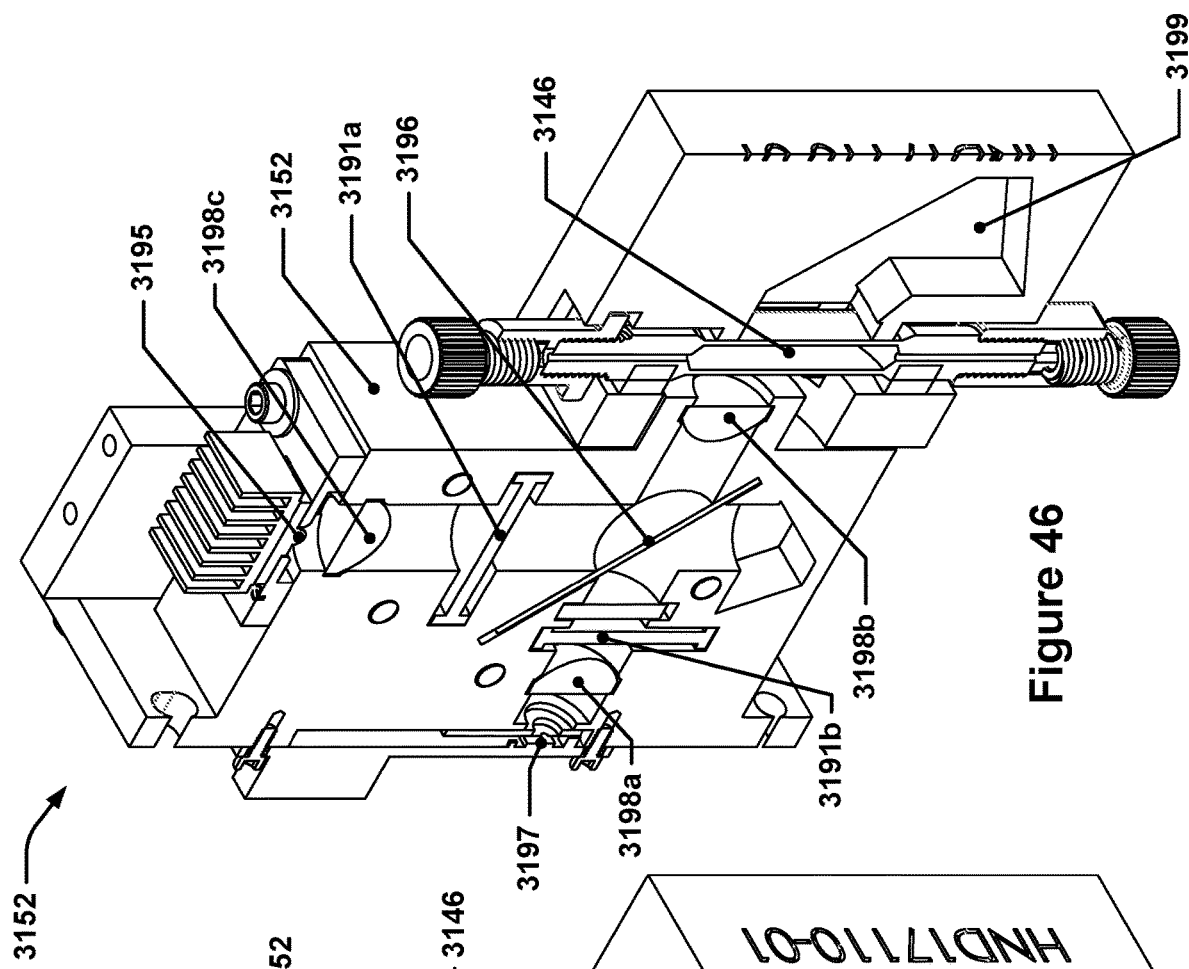
FIG. 46 depicts an isometric cross-sectional view of the example optical measurement device of FIG. 45.
Figure 45:
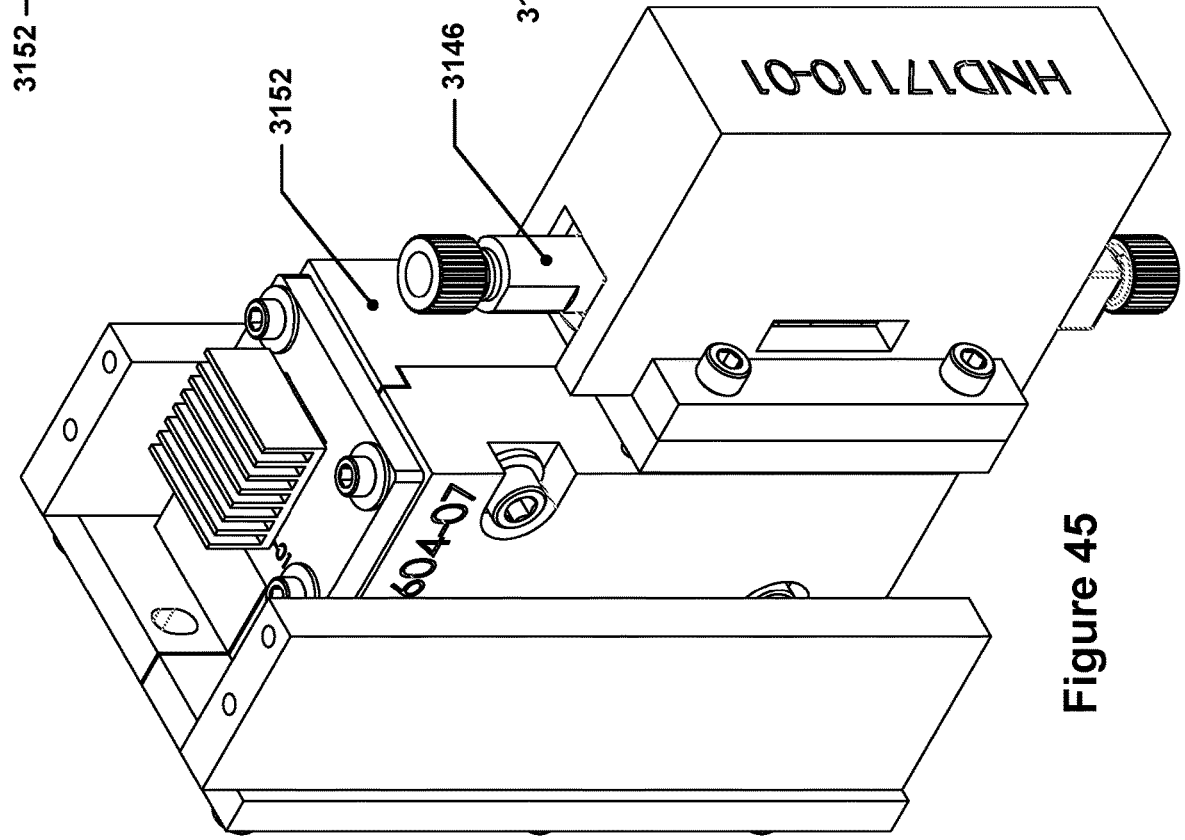
FIG. 45 depicts an isometric view of an example optical measurement device for the example target substance detection system of FIG. 31.

FIG. 45 depicts an isometric view of an example optical measurement device for the example target substance detection system of FIG. 31. FIG. 46 depicts an isometric cross-sectional view of the example optical measurement device of FIG. 45.

The optical measurement device 3152 may be attached to a housing that contains, for example, the optical measurement chamber 3146. The optical measurement device 3152 may include a photoemitter 3195, e.g., an LED or laser diode, and a photodetector 3197. The photoemitter 3195 may emit light of a particular wavelength range that may, for example, be focused by a lens 3198c before passing through an optical filter 3191a and then being reflected towards the optical measurement chamber 3146 by a dichroic mirror or beam splitter 3196. The reflected light may pass through another lens 3198b before reaching the optical measurement chamber, where it may cause any adduct that is in the optical measurement chamber to fluoresce before passing through the optical measurement chamber 3146 and being dissipated in a light trap 3199. The fluorescent emissions may pass back through the lens 3198b before passing through the dichroic mirror or beam splitter 3196, optical filter 3199b, and lens 3198a before reaching the photodetector 3197.

It is to be understood that this disclosure is not limited to the particular hardware layouts discussed in the examples herein. There are a multitude of different configurations of pumps, valves, cartridge layouts, and so forth that may be used to provide the features discussed herein. For example, instead of using four separate pumps 3118a-d, a single pump may be used in concert with a multiplexing valve having, for example, 12 ports that allow the pump to load/dispense fluids from/to any of the various reservoirs or mixing chambers discussed above. In some implementations, there may be multiple positive controls, each having a different amount of THC in it, in order to provide additional calibration information. It is also envisaged that the functionality discussed above may also be implemented in a microfluidic context, e.g., one or more of the reservoirs, mixing chambers, pumps, flow paths, etc. may be provided by microfluidic structures etched into a microfluidic platen, as opposed to being provided by discrete components connected together by tubing.

FIG. 47 depicts a flow chart showing an example technique for using an example target substance detection system. In FIG. 47, the technique may begin in block 4702 with the detection of the insertion of the reagent cartridge into the base station. In block 4704, the engagement of the cartridge load mechanism may be detected, which may then cause various other actions to be performed. For example, in block 4705, a lock mechanism that secures a handheld sample collection unit to the base station may be disengaged or released, allowing the handheld sample collection unit to be removed for sample collection, and in block 4706, the base station may start preparing the indicator by withdrawing the indicator solvent from the indicator solvent reservoir before dispensing the indicator solvent into the indicator reservoir in block 4708 and then mixing the indicator solvent with the indicator in block 4710. Once the indicator and indicator solvent have been mixed in block 4710, the liquid indicator may be loaded into the indicator pump in block 4712. While the indicator liquid is being prepared, the eluent may be loaded in the elution pump in block 4709, the activator may be loaded into the activator pump in block 4711, and the organic solvent may be loaded into the organic solvent pump in block 4713.

The base station may wait in block 4707 for a signal that the handheld sample collection unit has been docked, at which point a locking mechanism may be engaged. In block 4714, the base station may wait for an indication that the handheld sample collection unit has been secured to the base station. Once the handheld sample collection unit has been locked to the base station, the eluent may be dispensed to the BCM in the handled sample collection unit in block 4716. After the eluent has been allowed to reside in the BCM for a long enough period of time to elute any breath constituents that are in the BCM, the eluent and eluted breath constituents may be withdrawn from the BCM in block 4718 and transferred to the sample mixing chamber in block 4719.

The technique may then proceed to blocks 4720a-c, in which the indicator may be dispensed to the negative control mixing chamber, the sample mixing chamber, and the positive control mixing chamber. The technique may then proceed to blocks 4722a-c, in which the non-polar organic solvent may be dispensed to the negative control mixing chamber, the sample mixing chamber, and the positive control mixing chamber, after which the contents of the negative control mixing chamber, the sample mixing chamber, and the positive control mixing chamber may be mixed in blocks 4724a-c. After mixing, the technique may proceed to blocks 4726a-c, in which the polar and non-polar phases of the mixed contents of the mixing chambers may be allowed to separate before the activator is added to the separated solvents in blocks 4728a-c.

Once the sample and controls have been prepared for analysis, actual analysis of each may occur in blocks 4730a-c through blocks 4736a-c, respectively. For example, in block 4730a, the negative control may be pumped into the optical measurement chamber, followed in block 4734a by the obtaining of a measurement of the amount of fluorescence detected from the negative control (which, if there is no THC in the negative control, will generally be zero).

Once a fluorescence measurement has been made in block 4734a, the negative control may be pumped to the waste reservoir in block 4736a and the flow paths may be cleared out and/or dried before performing similar operations for the sample in blocks 4730b-4736b and for the positive control in blocks 4730c-4736c.

Figure 48:
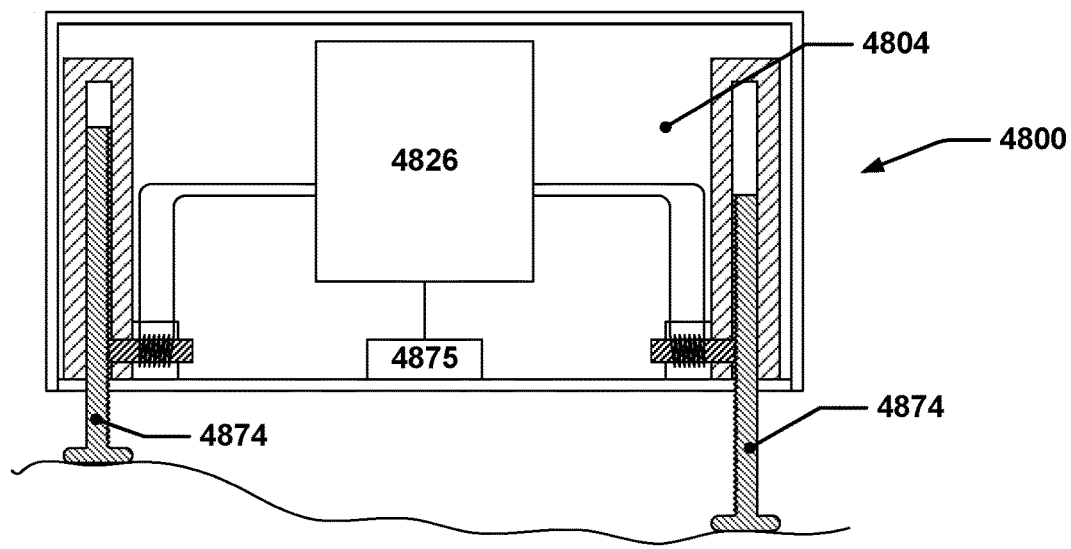
FIG. 48 depicts a schematic of a leveling system for a target substance detection system.

FIG. 48 depicts a schematic of a leveling system for a target substance detection system. As discussed earlier, some implementations of the analysis unit may include a level sensor or other mechanism to sense when the analysis unit is level. Such a sensor may, for example, be an inclinometer, accelerometer, or some other type of sensor that may provide output regarding whether the analysis unit is level (or that may provide an indication of the inclination of the analysis unit relative to the earth's gravitational field so that the degree to which the analysis unit is level or not level may be measured).

The analysis unit 4800 may have a base station 4804 that has a controller 4826 and a level sensor 4875, which may, for example, be an accelerometer. The controller 4826 may monitor the level sensor 4875 during use of the analysis unit 4800 and may take one or more actions in response to an indication that the base station 4804 is not level or is not within a predetermined range of level, e.g., ±10° of level (for the purposes of this disclosure, references to the base station 3104 being "level" refers not only to when the base station 3104 is completely level, but also to situations where the base station 3104 is within a predetermined range of being completely level). For example, in some implementations, the controller may cause an audible warning, e.g., a buzz, beep, chime, etc., or visible warning, e.g., a blinking or flashing light, to be activated when the base station 4804 is not level. In some additional or alternative implementations, the controller 4826 may cause the base station 4804 to halt or temporarily suspend one or more operations in the analysis routine in such situations. For example, if the controller 4826 determines that the base station 4804 is lying on its side or upside down, then the controller 4826 may suspend all mixing and fluid transfer operations until the base station 4804 is level again (in such scenarios, the controller may also require that the reagent cartridge be replaced since the contents of the reagent cartridge may have leaked out due to being upside down or sideways). In situations where the base station 4804 is not level but is not in an orientation that may have compromised the analysis even if later corrected (such as an orientation in which there may have been fluidic leakage), the controller 4826 may cause the base station 4804 to temporarily halt or delay certain operations until the non-level condition is corrected. For example, separation of the non-polar and polar layers after mixing of the organic non-polar solvent, the samples/controls, and subsequent transfer of a portion of the non-polar layers with the adduct (if present) to the optical measurement chamber may require that the mixing chambers (and thus the base station 4804) be level so that the non-polar layer is in the correct location relative to the end of the probe that will be used to obtain it (otherwise, the polar layer might be obtained instead, or perhaps air instead of fluid). Thus, the controller may be configured to cause the base station to ensure that the base station 3104, and thus the contents of the mixing chambers, have been level throughout the separation process and that they remain level until the analysis of the mixing chambers is complete. For example, if the base station 3104 is suddenly tilted out-of-level 20 seconds in to a 30 second window during which separation is allowed to occur, the controller 3126 may suspend or reset the 30 second window until the non-level condition is corrected and may then re-start the 30 second window once the base station 3104 is level again. Similarly, if the base station 3104 is tilted out-of-level in between measurements of the sample or controls, the controller 3126 may pause operations for another predetermined period of time to allow for the contents of the mixing chambers to separate again (if necessary) before performing any more transfers to the optical measurement chamber.

In some implementations, the base station 3104 may be equipped with mechanisms that may be used to counter or mitigate a non-level condition. For example, the base station 3104 may include a plurality of adjustable-height feet 3174 that may, for example, be independently extended to different lengths so as to allow the base station 3104 to rest on an uneven surface but still remain level. In some implementations, each foot 3174 may be individually and manually adjustable. However, in other implementations, the feet 3174 may be simultaneously released, e.g., solenoids that lock the feet 3174 into whatever position they are currently in may be simultaneously activated or de-activated in response to an input from a user, while the base station 3104 is held in a level condition by the user to release the feet 3174 and allow the feet 3174 to fall downwards until they each rest on the surface below the base station 3104. The feet 3174 may then be simultaneously locked in place to prevent the base station 3104 from tilting during use (such locking may be performed, for example, in response to another user input—for example, the base station 3104 may have a handle with a button on it that, when depressed, causes the feet to be released and, when undepressed, causes the feet to lock).

In some implementations, the feet 3174 may be connected with a drive system that allows the controller 3126 to actively control the degree of extension for each foot, e.g., the feet may each be connected to a linear drive or screw mechanism that allows each foot to be extended inwards or outwards in response to signals from the controller 3126. In such implementations, the controller may be configured to actively monitor the level condition of the base station 3104 and to control the extension/retraction of the feet 3174 such that the base station attains, and remains at, a level condition during use.

As noted earlier, the analysis systems and units discussed herein may include one or more processors, memory, and associated electronics to allow the one or more processors to control the valves, actuators, optical measurement sensor, air pump, and any other controllable elements of the analysis systems or units in order to carry out the operations discussed herein. The memory may store computer-executable instructions for controlling the one or more processors to cause such operations to occur. It is to be understood that the present disclosure relates not only to system and apparatus implementations of the analysis system discussed herein, but also to techniques, methods, and processes for using such analysis systems, as well as to embodiments in which computer-executable instructions for controlling a processor or processors to cause such techniques to be practiced are stored on some form of computer-readable media, e.g., non-transitory, computer-readable media such as a hard disk, solid state drive, or non-volatile flash memory.

In some instances, the one or more processors and memory may include at least one processor and memory that are part of the handheld sample collection unit 506 or 3106 and/or the reagent cartridge 502 or 3102 and/or the base station 504 or 3104. In such cases, there may be processors and memory distributed between two or more of such components, and the components may communicate with one another, either through a wireless communications interface or a wired connection. In some implementations, one or more of the above components may also have a wireless communications interface, e.g., a cellular interface, that allows the one or more processors to wirelessly communicate information to a remote device, e.g., a server. For example, the handheld sample collection unit 3106 may include a wireless interface that may transmit information relating to a sample, including, for example, metrics regarding the volume of exhaled breath, the time taken to obtain the sample, the time that the sample was obtained, the location where the sample was obtained (as either entered manually by a user or as obtained automatically, e.g., through use of a GPS receiver located in the handheld sample collection unit 3106 or in another nearby piece of equipment, such as a paired smartphone or police car), one or more fingerprints of a subject, and/or a picture of the subject providing the sample, e.g., as taken by a paired smartphone or by a camera that may be built in to the handheld sample collection unit 3106. The same wireless communications interface, or a different wireless communications interface, may also communicate test results from the analysis unit 3100 to the same remote device in association with such information or in association with a record identifier linking such further information to previously transmitted information, allowing test results to be associated with a particular subject and sampling time/location. In some implementations, the wireless interface that may allow for such long-range communications, e.g., a cellular interface, may be integrated into only one of the components of the analysis unit, e.g., the base station, and the other components may communicate wirelessly with the base station using shorter-range communications systems, e.g., Bluetooth, and the base station may then act as a relay and send data collected by the other components on to the remote device.

Figure 49:
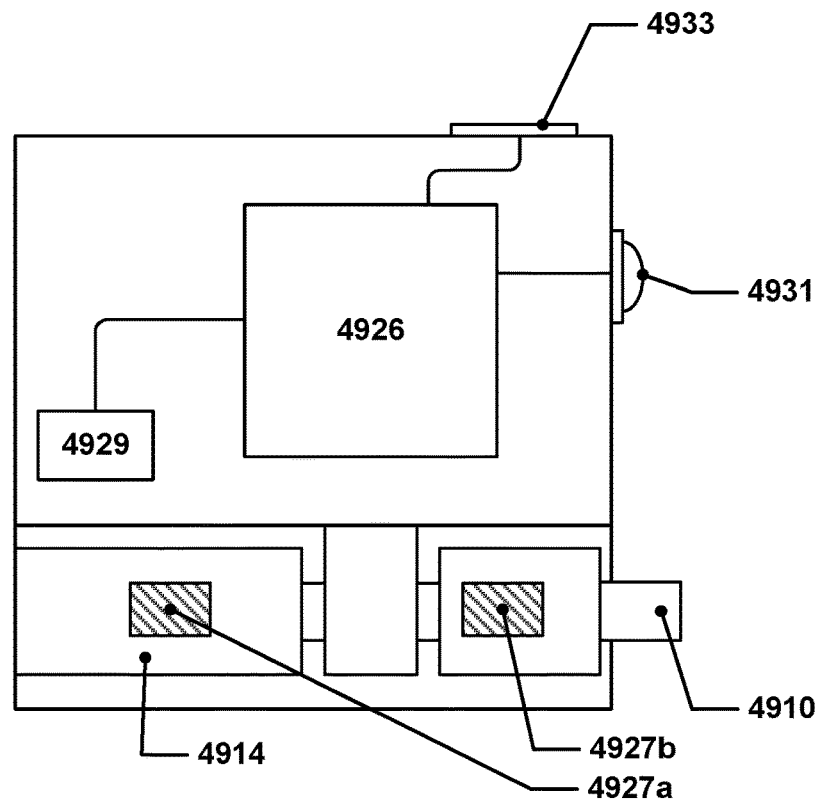
FIG. 49 depicts a schematic of a handheld sample collection unit.

FIG. 49 depicts a schematic of a handheld sample collection unit. In some implementations, the handheld sample collection unit 4906 may include various systems for establishing an evidentiary chain or ensuring the integrity and purity of a test sample. The handheld sample collection unit 4906 may include a controller 4926 as well as a mouthpiece 4910 and a BCM 4914 through which exhaled breath may be blown in order to collect a breath constituent sample. The mouthpiece 4910 and the BCM 4914 may be removable so that a clean, new instance of each may be used each time a sample is collected to avoid cross-contamination between samples. In some implementations, the mouthpiece 4910 may be configured to be inserted directly into the BCM 4914 so that virtually the entire flow path that the exhaled breath follows through these components is replaced each time the mouthpiece 4910 and the BCM 4914 are replaced (the exception to this may be the pressure port that may be included in the handheld sample collection unit 4906 and that may be used to monitor pressure within the BCM 4914 and/or the mouthpiece 4910).

As discussed earlier, in many implementations, the BCM 4914 may include a machine-readable code 4927*a*, e.g., a bar code, a QR code, an RFID tag, or an NFC tag, that uniquely identifies the BCM 4914, and the handheld sample collection unit 506 may be configured to read such a code, e.g., via a bar code scanner, QR scanner, RFID receiver, or NFC reader 4929. In some such implementations, the mouthpiece 4910 (and/or saliva trap) may also be equipped with a similar such machine-readable code 4927*b*. The handheld sample collection unit 4906 may thus be able to obtain a unique identifier for one or both of the BCM 4914 or the mouthpiece 4910 to allow that particular specific BCM 4914 and/or mouthpiece 4910 to be associated with the analysis results associated with a sample obtained using those identified components.

In addition to, or alternatively to, components for identifying a particular BCM 4914 or particular mouthpiece 4910 (or saliva trap), the handheld sample collection unit 4906 may also include one or more other sensors that may be used to associate a collected sample with a particular subject. For example, the handheld sample collection unit 4906 may include one or both of a camera 4931 and/or a fingerprint scanner 4933, which may be used to obtain imagery (still images or video) of a test subject immediately before or after a breath sample is obtained, or even during the collection of a breath sample, as well as to obtain a fingerprint of the subject. This imagery or fingerprint data may be transmitted to the base station and associated with any sample results that are obtained through analysis of the sample, thereby more definitely associating the results with a particular individual.

Figures 50, 51:
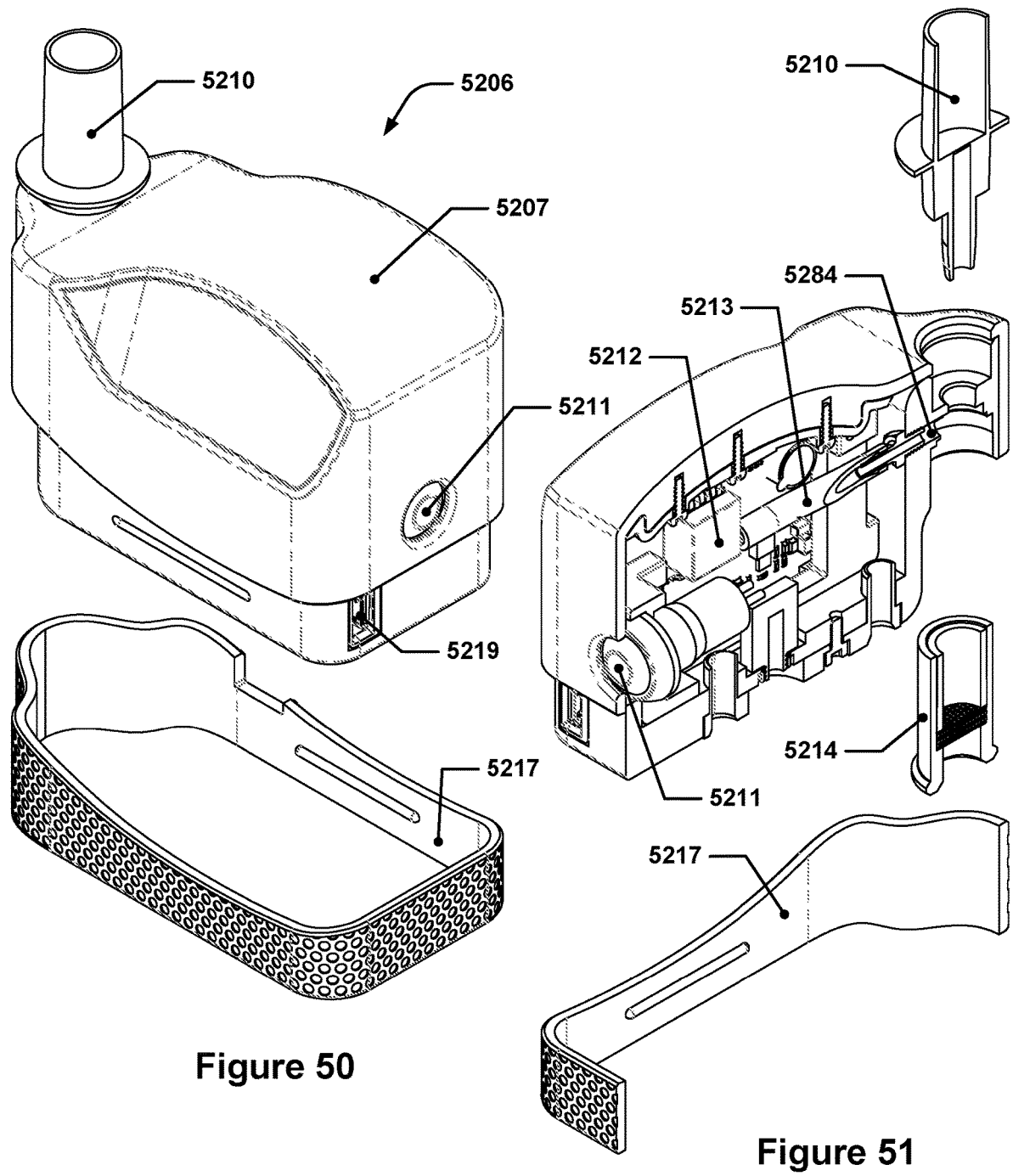
FIG. 50 depicts an isometric exploded view of another example handheld sample collection unit.
FIG. 51 depicts another isometric exploded section view of the example handheld collection unit of FIG. 50.
Figures 52, 53:
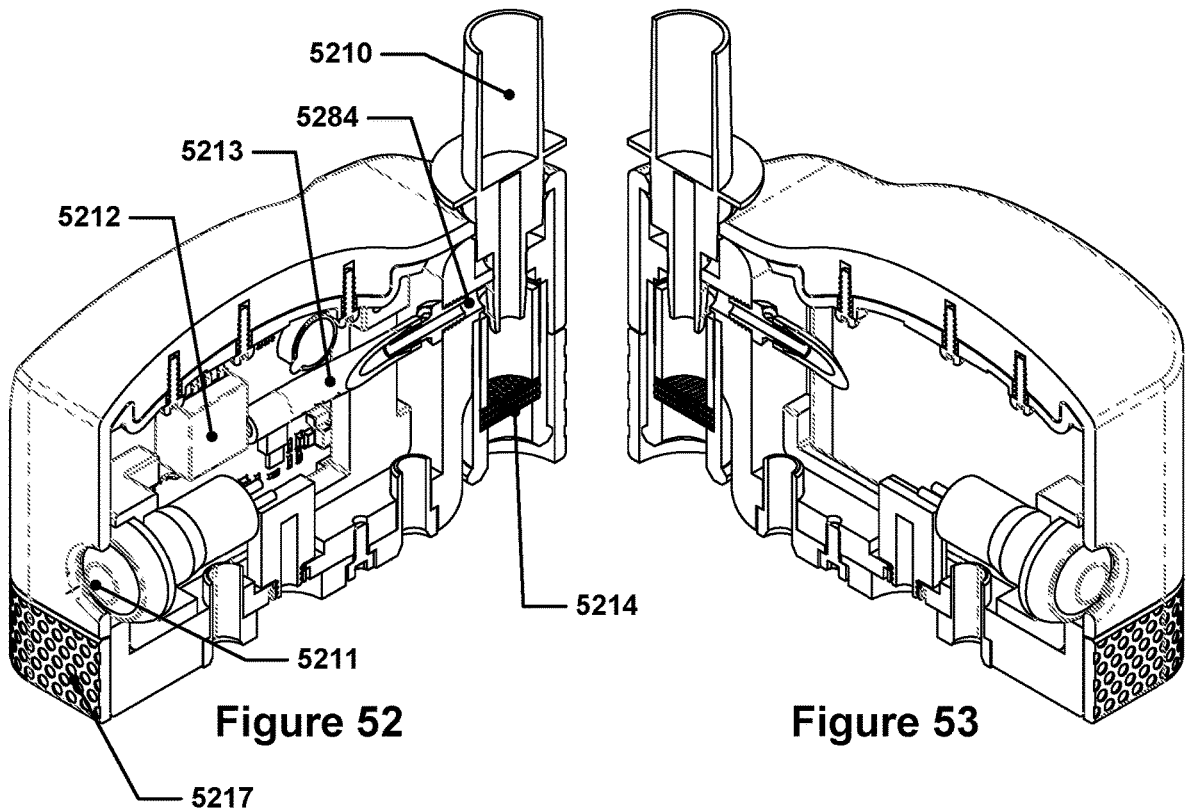
FIG. 52 depicts an isometric section view of the example handheld collection unit of FIG. 50.
FIG. 53 depicts another isometric section view of the example handheld collection unit of FIG. 50.
Figure 54:
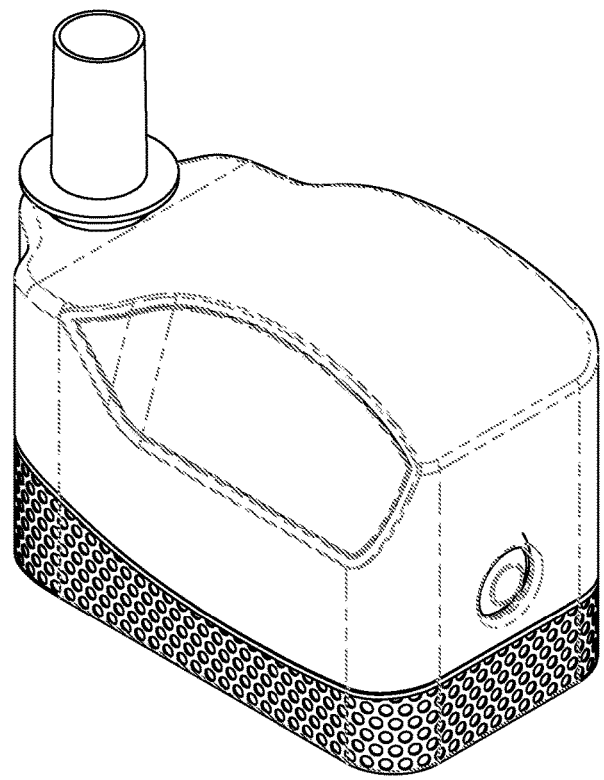
FIG. 54 depicts another isometric view of the example handheld collection unit of FIG. 50.
Figure 55:
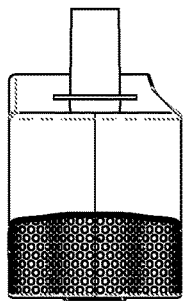
FIGS. 55 through 60 depict front, back, right, left, top, and bottom views of the example handheld collection unit of FIG. 50.
Figure 57:
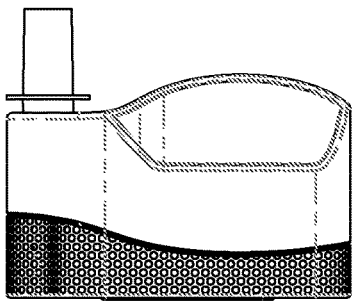
Figure 59:
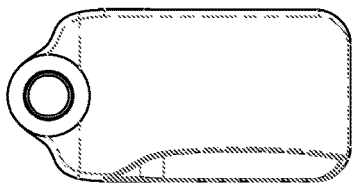
Figure 56:
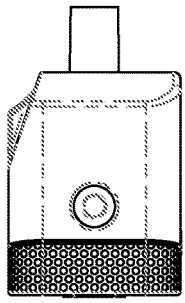
Figure 58:
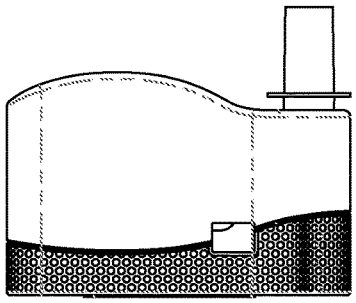
Figure 60:
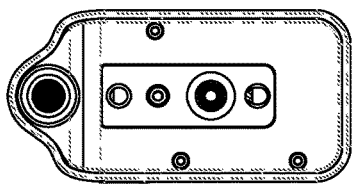
Figure 61:
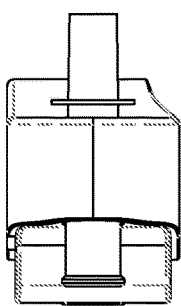
FIGS. 61 through 64 depict front, back, right, and left exploded views of the example handheld collection unit of FIG. 50.
Figure 62:
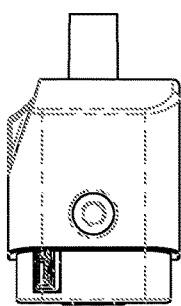
Figure 63:
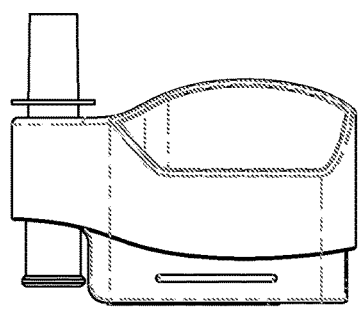
Figure 64:
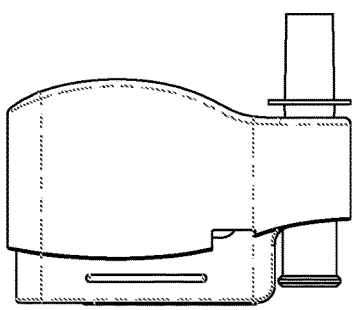

FIG. 50 depicts an isometric exploded view of another example handheld sample collection unit. FIG. 51 depicts another isometric exploded section view of the example handheld collection unit of FIG. 50. FIG. 52 depicts an isometric section view of the example handheld collection unit of FIG. 50. FIG. 53 depicts another isometric section view of the example handheld collection unit of FIG. 50. FIG. 54 depicts another isometric view of the example handheld collection unit of FIG. 50. FIGS. 55 through 60 depict front, back, right, left, top, and bottom views of the example handheld collection unit of FIG. 50. FIGS. 61 through 64 depict front, back, right, and left exploded views of the example handheld collection unit of FIG. 50.

As can be seen, the handheld sample collection unit 5206 may include a housing 5207 and a cover 5217 that may snap onto the housing 5207 to protect or cover a USB port 5219 and a BCM 5214. A saliva trap 5210 may be inserted into one end of a double-ended opening in the housing 5207 and the BCM 5214 may be inserted into the other end of the opening. A pressure port 5284 may fluidically connect the volume between the saliva trap 5210 and the BCM 5214 with a short length of tubing 5213 that may be connected with a pressure sensor 5212. A button 5211 may be used to allow the user to activate the handheld sample collection unit.

In one implementations consistent with the discussion provided above with respect to FIGS. 5 through 551, the following quantities and compositions of chemicals may be used (the table below is with reference to the quantities and compositions present prior to analysis):

| Mixing Chambers/Reservoirs | Composition | Amount, Notes |
| --- | --- | --- |
| Eluent | Ethanol (EtOH) | ≥750 µL (750 µL to be supplied to BCM for elution) |
| Negative Control Mixing Chamber | EtOH + Buffer | 750 µL (250 µL EtOH + 500 µL Buffer) |
| Positive Control Mixing Chamber | EtOH +THC + Buffer | 750 µL (~250 µL EtOH + ~500 µL Buffer + THC) (may adjust amounts of EtOH and/or Buffer down to equal 750 µL total with THC) |
| Sample Mixing Chamber | $NaHCO_3$ + $Na_2CO_3$ | 500 µL @ 20 mM $NaHCO_3$ and 13 mM $Na_2CO_3$ (250 µL of eluent + eluted breath constituent sample added to reach total volume of 750 µL prior to indicator addition) |
| Organic Solvent | Methyl tertiary butyl ether (MTBE) + Heptane | 3000 µL (2250 µL Heptane + 750 µL MTBE) (750 µL dispensed to each of positive control, negative control, and sample mixing chambers) |
| Indicator Solvent | Hydrochloric acid (HCl, 100 µM concentration) | 2000 µL delivered to indicator mixing chamber (250 µL of indicator + indicator solvent mixture then dispensed to each of positive control, negative control, and sample mixing chambers) |
| Indicator Chamber | Rhodamine + camphorsulfonic acid + sodium nitrite | 1 mg of powder |
| Activator | Poly(2-ethyl hexyl acrylate) | ≥600 µL (200 µL dispensed to each of positive control, negative control, and sample mixing chambers after mixing and separation) |

Example 3

Experiments were performed to evaluate the THC detection capabilities of instruments having systems and using methods in accordance with this disclosure.

Figure 65:
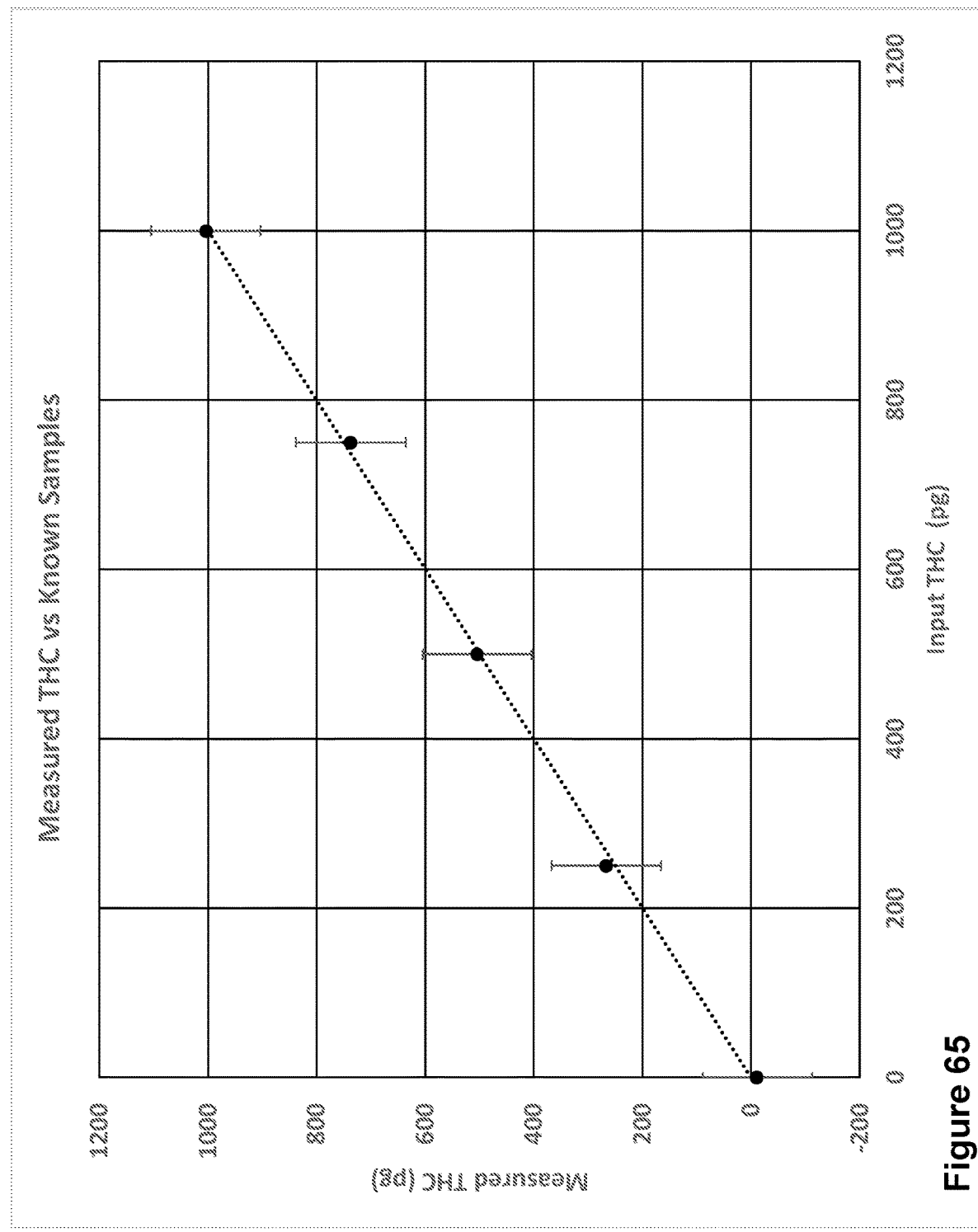
FIGS. 65 and 66 depict plots of data collected in experiments performed to evaluate the THC detection capabilities of instruments having systems and using methods in accordance with this disclosure.

Test samples of known amount were introduced into sample mixing chambers of reagent cartridge of multiple calibrated instruments similar to the examples discussed above, and THC amounts were detected for multiple runs on the multiple instruments. FIG. 65 is a plot showing the average measured THC levels from the multiple instruments against standard laboratory samples of the test samples. The data show the ability to reliably detect THC over a range of amounts, including low levels of THC in solution, across multiple instruments.

Figure 66:
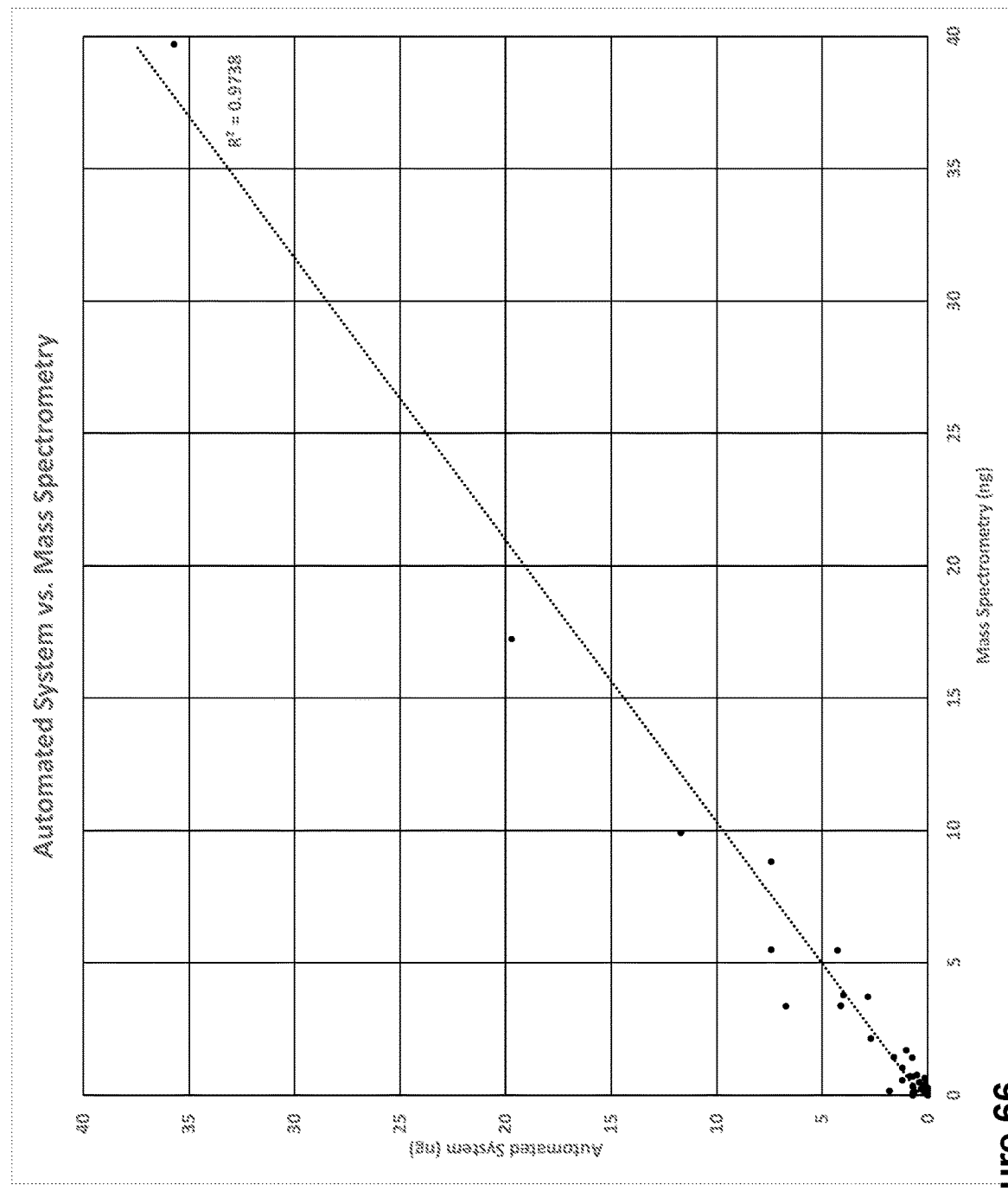

In another experiment, breath test samples were obtained from human subjects at various times following inhalation of THC. The test samples were processed in instruments having systems and using methods in accordance with this disclosure. THC amounts in the test samples were determined by the instruments and were also measured using mass spectrometry. FIG. 66 is a plot showing the correlation between calibrated instrument measurements and mass spectrometry measurements. The results show strong correlation between the instrument measurements and the mass spectrometry measurements, indicating that the instruments provide reliable quantitative detection of THC from breath samples.

Importantly, the present disclosure is neither limited to any single aspect nor implementation, nor to any combinations and/or permutations of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations are not discussed and/or illustrated separately herein.

While some specific embodiments have been described, it will be understood that it is not intended to limit the scope of the claims to such specific embodiments. On the contrary, it is intended to cover alternatives, modifications, and equivalents as may be included within the spirit and scope of this disclosure.

What is claimed:

1. A method of detecting THC in exhaled breath, comprising:
   receiving from a breath capture device an exhaled breath sample;
   processing the breath sample such that THC in the breath sample forms a fluorescent-labeled THC sample adduct dissolved in a nonpolar phase of an adduct solution;
   activating a fluorophore of the fluorescent-labeled THC sample adduct by adding a liquid phase chemical activator acryloyl species to the nonpolar phase; and
   detecting by determining an amount of THC in the breath sample based on the measured fluorescence of the activated fluorophore of the fluorescent-labeled THC sample adduct in the nonpolar phase isolated from aqueous media.

2. The method of claim 1, further comprising wherein the breath sample is also tested for ethanol, such that both THC and ethanol are measured from the same breath sample.

3. The method of claim 2, wherein a portion of the breath sample is routed through a blood alcohol sensor for ethanol measurement.

* * * * *